(12) United States Patent
Boulet et al.

(10) Patent No.: US 7,521,462 B2
(45) Date of Patent: *Apr. 21, 2009

(54) 4-AMINO-PIPERIDINE DERIVATIVES AS MONOAMINE UPTAKE INHIBITORS

(75) Inventors: Serge Louis Boulet, Fishers, IN (US); Barry Peter Clark, Basingstoke (GB); John Fairhurst, Basingstoke (GB); Peter Thaddeus Gallagher, Basingstoke (GB); Anette Margareta Johansson, Indianapolis, IN (US); Maria Ann Whatton, Basingstoke (GB); Virginia Ann Wood, Basingstoke (GB)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/597,795

(22) PCT Filed: Feb. 11, 2005

(86) PCT No.: PCT/US2005/004174

§ 371 (c)(1),
(2), (4) Date: Aug. 8, 2006

(87) PCT Pub. No.: WO2005/092885

PCT Pub. Date: Oct. 6, 2005

(65) Prior Publication Data

US 2007/0093526 A1    Apr. 26, 2007

Related U.S. Application Data

(60) Provisional application No. 60/548,679, filed on Feb. 27, 2004.

(51) Int. Cl.
*A61K 31/4468* (2006.01)
*A61K 31/4535* (2006.01)

(52) U.S. Cl. ............... 514/321; 514/324; 514/326; 546/209; 546/212

(58) Field of Classification Search ............ 546/194, 546/209, 212; 514/321, 324, 326
See application file for complete search history.

(56) References Cited

U.S. PATENT DOCUMENTS 4,064,255 A    12/1977   Champseix et al.
4,861,785 A *  8/1989   Stokbroekx et al. ......... 514/321
2007/0066663 A1* 3/2007 Beadle et al. ............... 514/359

FOREIGN PATENT DOCUMENTS

| EP | 0 965 587 A1 | 12/1999 |
|---|---|---|
| EP | 1 002 794 A1 | 5/2000 |
| WO | WO 94/13291 | 6/1994 |
| WO | WO 99/65487 | 12/1999 |
| WO | WO 00/59498 | 10/2000 |
| WO | WO 01/19817 A2 | 3/2001 |
| WO | WO 01/87839 A1 | 11/2001 |
| WO | WO 02/24649 A1 | 3/2002 |
| WO | WO 03/049736 A1 | 6/2003 |
| WO | WO 03/051842 A2 | 6/2003 |
| WO | WO 03/086397 A1 | 10/2003 |
| WO | WO 2004/052858 A2 | 6/2004 |
| WO | WO 2005/000305 A1 | 1/2005 |
| WO | WO 2005/000811 A1 | 1/2005 |

OTHER PUBLICATIONS

Thomas Ryckmans et al., First Dual NK1 Antagonists-Serotonin Reuptake Inhibitors: Synthesis and SAR of a New Class of Potential Antidepressants *Bioorganic & Medicinal Chemistry Letters*, 2002, 261-264 vol. 12.

* cited by examiner

*Primary Examiner*—Rita J Desai
*Assistant Examiner*—David K O'Dell
(74) *Attorney, Agent, or Firm*—Paul J. Gaylo; Arvie J. Anderson

(57) ABSTRACT

The present invention provides compounds of formula (I) where n, R1, R2, R3, R4, R5 and Heteroaryl are defined herein. The compounds are inhibitors of the uptake of one or more monoamines selected from serotonin, norepinephrine and dopamine and, as such, may be useful in the treatment of disorders of the central and/or peripheral nervous system.

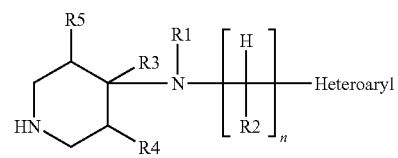

(I)

2 Claims, No Drawings

4-AMINO-PIPERIDINE DERIVATIVES AS MONOAMINE UPTAKE INHIBITORS

This is the national phase application, under 35 USC 371, for PCT/US2005/004174, filed 11 Feb. 2005, which claims the benefit, under 35 USC 119(e), of U.S. provisional application 60/548,679, filed 27 Feb. 2004.

The present invention is directed to compounds which inhibit the uptake of one or more physiologically active monoamines selected from serotonin (also called 5-hydroxytryptamine or 5-HT), norepinephrine (also called noradrenaline) and dopamine. There is a large body of scientific evidence pointing to the physiological role of these monoamines as neurotransmitters. Consequently, compounds which are capable of inhibiting the uptake of one or more of these monoamines find utility in the treatment of disorders of the central and/or peripheral nervous system.

Many compounds exhibiting this kind of pharmacology are known in the art. For example, it is known that the 3-aryloxy-3-substituted-1-aminopropane class of compounds have demonstrated particular diversity in their ability to inhibit the uptake of monoamines. Fluoxetine (N-methyl 3-((4-trifluoromethylphenyl)oxy)-3-phenyl-1-aminopropane hydrochloride), for example, is a selective serotonin uptake inhibitor that has found great market acceptance in the treatment of depression and has also been approved for the treatment of a number of other disorders. Atomoxetine ((−)-N-methyl 3-((2-methylphenyl)oxy)-3-phenyl-1-aminopropane hydrochloride), is a selective norepinephrine uptake inhibitor that is approved for the treatment of attention deficit/hyperactivity disorder. Duloxetine ((+)-N-methyl 3-(1-naphthalenyloxy)-3-(2-thienyl)-1-aminopropane hydrochloride), is a dual serotonin and norepinephrine uptake inhibitor that is in clinical development for the treatment of depression and stress urinary incontinence.

Despite the existence of such known compounds, it would be advantageous to provide further compounds which are capable of inhibiting the uptake of one or more monoamines selected from serotonin, norepinephrine and dopamine. Preferably, such compounds would exhibit one or more of the following characteristics when compared with known monoamine uptake inhibitors—(i) improved potency in their inhibition of one or more of these monoamines, (ii) improved selectivity in their inhibition of one or more of these monoamines, (iii) improved bioavailability, (iv) minimal interaction with metabolic enzymes such as CYP2D6 and (v) improved acid stability.

WO03/086397 discloses a class of compounds of the general formula (34) as intermediates in the synthesis of histone deacetylase inhibitors:

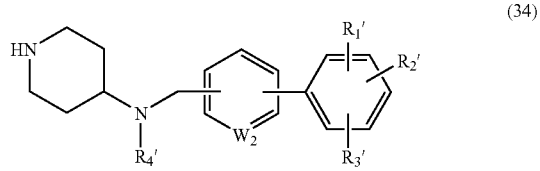

(34)

wherein $W_2$ is N or CH; $R_1'$, $R_2'$ and $R_3'$ each independently represent a hydrogen atom, a halogen atom, a hydroxy group, an alkyl group, a halogen-substituted alkyl group, an alkoxy group, an alkylthio group, a carboxy group, an alkoxycarbonyl group, or an alkanoyl group; and $R_4'$ denotes an alkyl, alkenyl, alkynyl, aralkyl, heteroaralkyl, aryl or heteroaryl group. In particular, it discloses the compound:

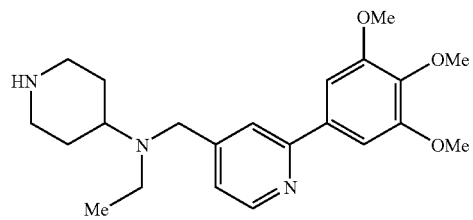

WO03/051842 discloses the compounds shown below as intermediates in the synthesis of carbamates as hormone sensitive lipase inhibitors:

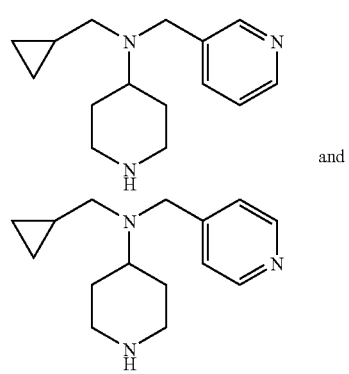

and

WO00/59498 discloses the compound shown below as an intermediate in the synthesis of modulators of chemokine receptor activity:

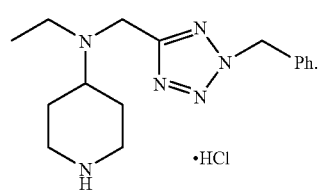

WO01/87839 discloses compounds of the general formula:

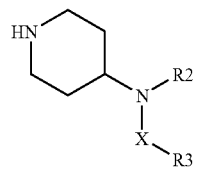

wherein R2 is inter alia C1-8alkyl, X is inter alia a direct bond and R3 is inter alia heteroaryl($C_{1-4}$alkyl), as intermediates in the synthesis of certain piperidine derivatives which are modulators of chemokine receptor activity.

WO03/049736 discloses certain 4-substituted piperidines as ligands for various mammalian cellular receptors, including dopamine, serotonin or norepinephrine transporters.

WO02/24649 discloses certain substituted amino-aza-cycloalkane derivatives as inhibitors of the plasmodium falciparum protease plasmepsin II or related aspartic proteases.

WO01/19817 discloses a group of aza ring derivatives as modulators of nicotinic acetylcholine receptors.

WO94/13291 discloses a class of cyclic secondary amine derivatives as calcium channel antagonists.

EP1002794 discloses certain 4-substituted piperidines as inhibitors of serotonin and/or noradrenaline reuptake.

WO99/65487 discloses certain 4-substituted piperidines as inhibitors of serotonin reuptake.

U.S. Pat. No. 4,064,255 discloses certain 4-substituted piperidines, including indalpine, as inhibitors of serotonin reuptake.

Bioorganic & Medicinal Chemistry Letters 12 (2002) 261-264 (Thomas Ryckmnans et.al.) discloses inter alia the following compound as a dual NK1 antagonist and serotonin reuptake inhibitor.

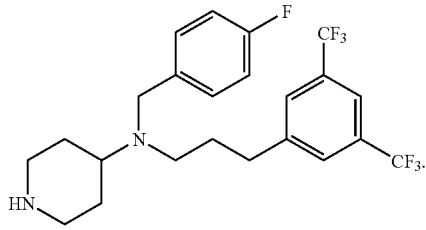

WO2004/052858 discloses N,N-disubstituted 4-amino-piperidines as inhibitors of monoamine uptake.

WO2005/000305 discloses N,N-disubstituted 3-aminopiperidines and N,N-disubstituted 3-aminoquinuclidines as inhibitors of monoamine uptake.

WO2005/000811 discloses N,N-disubstituted 3-aminopyrrolidines as inhibitors of monoamine uptake.

The present invention provides a compound of formula (I)

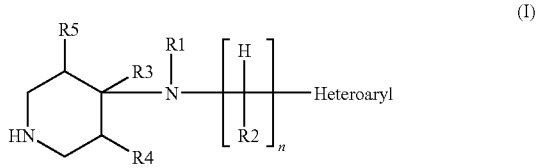

wherein n is 1, 2 or 3;

R1 is $C_2$-$C_{10}$alkyl, $C_2$-$C_{10}$alkenyl, $C_3$-$C_8$cycloalkyl, $C_3$-$C_8$cycloalkenyl, $C_4$-$C_{10}$cycloalkylalkyl or $C_4$-$C_{10}$cycloalkenylalkyl wherein one —$CH_2$— within any cycloalkyl moiety is optionally substituted by —O— or —S— and wherein each group is optionally substituted with from 1 to 7 halogen substituents and/or with from 1 to 3 substituents each independently selected from hydroxy, cyano, $C_1$-$C_4$alkyl, $C_1$-$C_4$alkylthio (optionally substituted with from 1 to 3 halogen atoms) and $C_1$-$C_4$alkoxy (optionally substituted with from 1 to 3 halogen atoms);

R2 is independently at each occurrence selected from H and $C_1$-$C_4$alkyl;

R3 is H or $C_1$-$C_4$alkyl;

R4 is H, halogen, hydroxy, cyano, $C_1$-$C_4$alkyl or $C_1$-$C_4$alkoxy;

R5 is H, halogen, hydroxy, cyano, $C_1$-$C_4$alkyl or $C_1$-$C_4$alkoxy; and

Heteroaryl is (i) a 5- or 6-membered monocyclic heteroaromatic group optionally substituted with 1, 2, 3 or 4 substituents (depending on the number of available substitution positions) each independently selected from halo, cyano, $C_1$-$C_4$alkyl (optionally substituted with 1, 2 or 3 F atoms), $C_1$-$C_4$alkoxy (optionally substituted with 1, 2 or 3 F atoms) and $C_1$-$C_4$alkylthio (optionally substituted with 1, 2 or 3 F atoms) and/or with 1 substituent selected from pyridinyl, pyrazolyl, phenyl (optionally substituted with 1, 2 or 3 halo substituents), benzyl (optionally substituted with 1, 2 or 3 halo substituents) and phenoxy (optionally substituted with 1, 2 or 3 halo substituents) with the proviso that only $C_1$-$C_4$alkyl may be a substituent for the H of any —NH— moiety present within the group, or (ii) an 8-, 9- or 10-membered bicyclic heteroaromatic group optionally substituted with 1, 2, 3, 4, 5 or 6 substituents (depending on the number of available substitution positions) each independently selected from halo, cyano, $C_1$-$C_4$alkyl (optionally substituted with 1, 2 or 3 F atoms), $C_1$-$C_4$alkoxy (optionally substituted with 1, 2 or 3 F atoms) and $C_1$-$C_4$alkylthio (optionally substituted with 1, 2 or 3 F atoms) with the proviso that only $C_1$-$C_4$alkyl may be a substituent for the H of any —NH— moiety present within the group;

or a pharmaceutically acceptable salt thereof, for use in a method for treatment of the human or animal body by therapy.

In another embodiment, the present invention provides a pharmaceutical composition comprising a compound of formula (I) as defined above, or a pharmaceutically acceptable salt thereof, together with a pharmaceutically acceptable diluent, excipient or carrier.

In another embodiment, the present invention provides a method of inhibiting the uptake of one or more monoamines selected from serotonin, dopamine and norepinephrine in a mammal, comprising administering to a mammal in need of such inhibition an effective amount of a compound of formula (I) as defined above, or a pharmaceutically acceptable salt thereof.

In another embodiment, the present invention provides for the use of a compound of formula (I) as defined above, or a pharmaceutically acceptable salt thereof, for the manufacture of a medicament for inhibiting the uptake of one or more monoamines selected from serotonin, dopamine and norepinephrine.

In another embodiment, the present invention provides novel compounds of formula (I) as defined above, or pharmaceutically acceptable salts thereof, with the proviso that the compounds

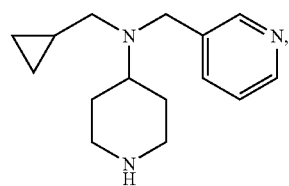

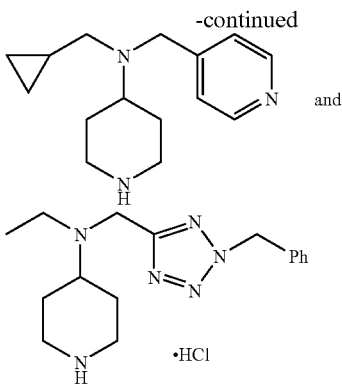

and are excluded.

In the present specification the term "$C_2$-$C_{10}$alkyl" means a monovalent unsubstituted saturated straight-chain or branched-chain hydrocarbon radical having from 2 to 10 carbon atoms.

In the present specification the term "$C_2$-$C_{10}$alkenyl" means a monovalent unsubstituted unsaturated straight-chain or branched-chain hydrocarbon radical having from 2 to 10 carbon atoms and containing at least one (and preferably only one) carbon-carbon double bond.

In the present specification the term "$C_3$-$C_8$cycloalkyl" means a monovalent unsubstituted saturated monocyclic or bicyclic hydrocarbon radical having from 3 to 8 carbon atoms.

In the present specification the term "$C_3$-$C_8$cycloalkenyl" means a monovalent unsubstituted unsaturated monocyclic or bicyclic hydrocarbon radical having from 3 to 8 carbon atoms and containing one carbon-carbon double bond.

In the present specification the term "$C_4$-$C_{10}$cycloalkylalkyl" means a monovalent unsubstituted saturated monocyclic or bicyclic hydrocarbon radical having from 3 to 9 carbon atoms, linked to the point of substitution via a divalent unsubstituted saturated straight-chain or branched-chain hydrocarbon radical having at least 1 carbon atom.

In the present specification the term "$C_4$-$C_{10}$cycloalkenylalkyl" means a monovalent unsubstituted unsaturated monocyclic or bicyclic hydrocarbon radical having from 3 to 9 carbon atoms and containing one carbon-carbon double bond, linked to the point of substitution via a divalent unsubstituted saturated straight-chain or branched-chain hydrocarbon radical having at least 1 carbon atom.

In the present specification the term "halo" or "halogen" means F, Cl, Br or I.

In the present specification the term "$C_1$-$C_4$alkylthio" means a monovalent unsubstituted saturated straight-chain or branched-chain hydrocarbon radical having from 1 to 4 carbon atoms linked to the point of substitution by a S atom.

In the present specification the term "$C_1$-$C_4$alkoxy" means a monovalent unsubstituted saturated straight-chain or branched-chain hydrocarbon radical having from 1 to 4 carbon atoms linked to the point of substitution by an O atom.

In the present specification the term "5- or 6-membered monocyclic heteroaromatic group" means a monocyclic aromatic group with a total of 5 or 6 atoms in the ring wherein from 1 to 4 of those atoms are each independently selected from N, O and S. Preferred groups have 1 or 2 atoms in the ring which are each independently selected from N, O and S. Suitable 5-membered monocyclic heteroaromatic groups include pyrrolyl (also called azolyl), furanyl, thienyl, pyrazolyl (also called 1H-pyrazolyl and 1,2-diazolyl), imidazolyl, oxazolyl (also called 1,3-oxazolyl), isoxazolyl (also called 1,2-oxazolyl), thiazolyl (also called 1,3-thiazolyl), isothiazolyl (also called 1,2-thiazolyl), triazolyl, oxadiazolyl, thiadiazolyl, tetrazolyl, oxatriazolyl and thiatriazolyl. Suitable 6-membered monocyclic heteroaromatic groups include pyridinyl, pyrimidyl, pyrazinyl, pyridazinyl and triazinyl.

"Pyrrolyl" as used herein includes pyrrol-2-yl and pyrrol-3-yl.

"Furanyl" as used herein includes furan-2-yl and furan-3-yl.

"Thienyl" as used herein includes thien-2-yl and thien-3-yl.

"Pyrazolyl" as used herein includes pyrazol-3-yl, pyrazol-4-yl and pyrazol-5-yl.

"Imidazolyl" as used herein includes imidazol-2-yl, imidazol-4-yl and imidazol-5-yl.

"Oxazolyl" as used herein includes oxazol-2-yl, oxazol-4-yl and oxazol-5-yl.

"Isoxazolyl" as used herein includes isoxazol-3-yl, isoxazol-4-yl, and isoxazol-5-yl.

"Thiazolyl" as used herein includes thiazol-2-yl, thiazol-4-yl and thiazol-5-yl.

"Isothiazolyl" as used herein includes isothiazol-3-yl, isothiazol-4-yl, and isothiazol-5-yl.

"Triazolyl" as used herein includes 1,2,3-triazol-1-yl, 1,2,3-triazol-4-yl, 1,2,3-triazol-5-yl, 1,2,4-triazol-1-yl, 1,2,4-triazol-3-yl and 1,2,4-triazol-5-yl.

"Oxadiazolyl" as used herein includes 1,2,3-oxadiazol-4-yl, 1,2,3-oxadiazol-5-yl, 1,2,4-oxadiazol-3-yl, 1,2,4-oxadiazol-5-yl, 1,2,5-oxadiazol-3-yl and 1,3,4-oxadiazol-2-yl.

"Thiadiazolyl" as used herein includes 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl (also called furazan-3-yl) and 1,3,4-thiadiazol-2-yl.

"Tetrazolyl" as used herein includes tetrazol-1-yl and tetrazol-5-yl.

"Oxatriazolyl" as used herein includes 1,2,3,4-oxatriazol-5-yl and 1,2,3,5-oxatriazol-4-yl.

"Thiatriazolyl" as used herein includes 1,2,3,4-thiatriazol-5-yl and 1,2,3,5-thiatriazol-4-yl.

"Pyridinyl" as used herein includes pyridin-2-yl, pyridin-3-yl and pyridin-4-yl.

"Pyrimidyl" as used herein includes pyrimid-2-yl, pyrimid-4-yl, pyrimid-5-yl and pyrimid-6-yl.

"Pyridazinyl" as used herein includes pyridazin,-3-yl and pyridazin-4-yl.

"Pyrazinyl" as used herein includes pyrazin-2-yl and pyrazin-3-yl.

"Triazinyl" as used herein includes 1,3,5-triazin-2-yl, 1,2,4-triazin-3-yl, 1,2,4-triazin-5-yl, 1,2,4-triazin-6-yl, 1,2,3-triazin-4-yl and 1,2,3-triazin-5-yl.

In the present specification the term "8-, 9- or 10-membered bicyclic heteroaromatic group" means a fused bicyclic aromatic group with a total of 8, 9 or 10 atoms in the ring system wherein from 1 to 4 of those atoms are each independently selected from N, O and S. Preferred groups have from 1 to 3 atoms in the ring system which are each independently selected from N, O and S. Suitable 8-membered bicyclic heteroaromatic groups include imidazo[2,1-b][1,3]thiazolyl, thieno[3,2-b]thienyl, thieno[2,3-d][1,3]thiazolyl and thieno[2,3-d]imidazolyl. Suitable 9-membered bicyclic heteroaromatic groups include indolyl, isoindolyl, benzofuranyl (also called benzo[b]furanyl), isobenzofuranyl (also called benzo[c]furanyl), benzothienyl (also called benzo[b]thienyl), isobenzothienyl (also called benzo[c]thienyl), indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl and imidazo[1,2-a]pyridine. Suitable 10-membered bicyclic heteroaromatic groups include quinolinyl, isoquinolinyl, cinnolinyl, quinazolinyl, quinoxalinyl, 1,5-naphthyridyl, 1,6-naphthyridyl, 1,7-naphthyridyl and 1,8-naphthyridyl.

"Imidazo[2,1-b][1,3]thiazolyl" as used herein includes imidazo[2,1-b][1,3]thiazol-2-yl, imidazo[2,1-b][1,3]thiazol-3-yl, imidazo[2,1-b][1,3]thiazol-5-yl and imidazo[2,1-b][1,3]thiazol-6-yl.

"Thieno[3,2-b]thienyl" as used herein includes thieno[3,2-b]thien-2-yl, thieno[3,2-b]thien-3-yl, thieno[3,2-b]thien-5-yl and thieno[3,2-b]thien-6-yl.

"Thieno[2,3-d][1,3]thiazolyl" as used herein includes thieno[2,3-d][1,3]thiazol-2-yl, thieno[2,3-d][1,3]thiazol-5-yl and thieno[2,3-d][1,3]thiazol-6-yl.

"Thieno[2,3-d]imidazolyl" as used herein includes thieno[2,3-d]imidazol-2-yl, thieno[2,3-d]imidazol-4-yl and thieno[2,3-d]imidazol-5-yl.

"Indolyl" as used herein includes indol-1-yl, indol-2-yl, indol-3-yl, indol-4-yl, indol-5-yl, indol-6-yl and indol-7-yl.

"Isoindolyl" as used herein includes isoindol-1-yl, isoindol-2-yl, isoindol-3-yl, isoindol-4-yl, isoindol-5-yl, isoindol-6-yl and isoindol-7-yl.

"Benzofuranyl" as used herein includes benzofuran-2-yl, benzofuran-3-yl, benzofuran-4-yl, benzofuran-5-yl, benzofuran-6-yl and benzofuran-7-yl.

"Isobenzofuranyl" as used herein includes isobenzofuran-1-yl, isobenzofuran-3-yl, isobenzofuran-4-yl, isobenzofuran-5-yl, isobenzofuran-6-yl and isobenzofuran-7-yl.

"Benzothienyl" as used herein includes benzothien-2-yl, benzothien-3-yl, benzothien-4-yl, benzothien-5-yl, benzothien-6-yl and benzothien-7-yl.

"Isobenzothienyl" as used herein includes isobenzothien-1-yl, isobenzothien-3-yl, isobenzothien-4-yl, isobenzothien-5-yl, isobenzothien-6-yl and isobenzothien-7-yl.

"Indazolyl" as used herein includes indazol-1-yl, indazol-3-yl, indazol-4-yl, indazol-5-yl, indazol-6-yl and indazol-7-yl.

"Benzimidazolyl" as used herein includes benzimidazol-1-yl, benzimidazol-2-yl, benzimidazol-4-yl, benzimidazol-5-yl, benzimidazol-6-yl and benzimidazol-7-yl.

"1,3-Benzoxazolyl" as used herein includes 1,3-benzoxazol-2-yl, 1,3-benzoxazol-4-yl, 1,3-benzoxazol-5-yl, 1,3-benzoxazol-6-yl and 1,3-benzoxazol-7-yl.

"1,2-Benzisoxazolyl" as used herein includes 1,2-benzisoxazol-3-yl, 1,2-benzisoxazol-4-yl, 1,2-benzisoxazol-5-yl, 1,2-benzisoxazol-6-yl and 1,2-benzisoxazol-7-yl.

"2,1-Benzisoxazolyl" as used herein includes 2,1-benzisoxazol-3-yl, 2,1-benzisoxazol-4-yl, 2,1-benzisoxazol-5-yl, 2,1-benzisoxazol-6-yl and 2,1-benzisoxazol-7-yl.

"1,3-Benzothiazolyl" as used herein includes 1,3-benzothiazol-2-yl, 1,3-benzothiazol-4-yl, 1,3-benzothiazol-5-yl, 1,3-benzothiazol-6-yl and 1,3-benzothiazol-7-yl.

"1,2-Benzoisothiazolyl" as used herein includes 1,2-benzisothiazol-3-yl, 1,2-benzisothiazol-4-yl, 1,2-benzisothiazol-5-yl, 1,2-benzisothiazol-6-yl and 1,2-benzisothiazol-7-yl.

"2,1-Benzoisothiazolyl" as used herein includes 2,1-benzisothiazol-3-yl, 2,1-benzisothiazol-4-yl, 2,1-benzisothiazol-5-yl, 2,1-benzisothiazol-6-yl and 2,1-benzisothiazol-7-yl.

"Benzotriazolyl" as used herein includes benzotriazol-1-yl, benzotriazol-4-yl, benzotriazol-5-yl, benzotriazol-6-yl and benzotriazol-7-yl.

"1,2,3-Benzoxadiazolyl" as used herein includes 1,2,3-benzoxadiazol-4-yl, 1,2,3-benzoxadiazol-5-yl, 1,2,3-benzoxadiazol-6-yl and 1,2,3-benzoxadiazol-7-yl.

"2,1,3-Benzoxadiazolyl" as used herein includes 2,1,3-benzoxadiazol-4-yl, 2,1,3-benzoxadiazol-5-yl, 2,1,3-benzoxadiazol-6-yl and 2,1,3-benzoxadiazol-7-yl.

"1,2,3-Benzothiadiazolyl" as used herein includes 1,2,3-benzothiadiazol-4-yl, 1,2,3-benzothiadiazol-5-yl, 1,2,3-benzothiadiazol-6-yl and 1,2,3-benzothiadiazol-7-yl.

"2,1,3-Benzothiadiazolyl" as used herein includes 2,1,3-benzothiadiazol-4-yl, 2,1,3-benzothiadiazol-5-yl, 2,1,3-benzothiadiazol-6-yl and 2,1,3-benzothiadiazol-7-yl.

"Thienopyridinyl" as used herein includes thieno[2,3-b]pyridinyl, thieno[2,3-c]pyridinyl, thieno[3,2-c]pyridinyl and thieno[3,2-b]pyridinyl.

"Purinyl" as used herein includes purin-2-yl, purin-6-yl, purin-7-yl and purin-8-yl.

"Imidazo[1,2-a]pyridinyl" as used herein includes imidazo[1,2-a]pyridin-2-yl, imidazo[1,2-a]pyridin-3-yl, imidazo[1,2-a]pyridin-4-yl, imidazo[1,2-a]pyridin-5-yl, imidazo[1,2-a]pyridin-6-yl and imidazo[1,2-a]pyridin-7-yl.

"Quinolinyl" as used herein includes quinolin-2-yl, quinolin-3-yl, quinolin-4-yl, quinolin-5-yl, quinolin-6-yl, quinolin-7-yl and quinolin-8-yl.

"Isoquinolinyl" as used herein includes isoquinolin-1-yl, isoquinolin-3-yl, isoquinolin-4-yl, isoquinolin-5-yl, isoquinolin-6-yl, isoquinolin-7-yl and isoquinolin-8-yl.

"Cinnolinyl" as used herein includes cinnolin-3-yl, cinnolin-4-yl, cinnolin-5-yl, cinnolin-6-yl, cinnolin-7-yl and cinnolin-8-yl.

"Quinazolinyl" as used herein includes quinazolin-2-yl, quinazolin-4-yl, quinazolin-5-yl, quinazolin-6-yl, quinazolin-7-yl and quinazolin-8-yl.

"1,4-Naphthyridyl" as used herein includes 1,4-naphthyrid-2-yl, 1,4-naphthyrid-3-yl, 1,4-naphthyrid-5-yl, 1,4-naphthyrid-6-yl, 1,4-naphthyrid-7-yl and 1,4-naphthyrid-8-yl.

"1,5-Naphthyridyl" as used herein includes 1,5-naphthyrid-2-yl, 1,5-naphthyrid-3-yl, 1,5-naphthyrid-4-yl, 1,5-naphthyrid-6-yl, 1,5-naphthyrid-7-yl and 1,5-naphthyrid-8-yl.

"1,6-Naphthyridyl" as used herein includes 1,6-naphthyrid-2-yl, 1,6-naphthyrid-3-yl, 1,6-naphthyrid-4-yl, 1,6-naphthyrid-5-yl, 1,6-naphthyrid-7-yl and 1,6-naphthyrid-8-yl.

"1,7-Naphthyridyl" as used herein includes 1,7-naphthyrid-2-yl, 1,7-naphthyrid-3-yl, 1,7-naphthyrid-4-yl, 1,7-naphthyrid-5-yl, 1,7-naphthyrid-6-yl and 1,7-naphthyrid-8-yl.

"1,8-Naphthyridyl" as used herein includes 1,8-naphthyrid-2-yl, 1,8-naphthyrid-3-yl, 1,8-naphthyrid-4-yl, 1,8-naphthyrid-5-yl, 1,8-naphthyrid-6-yl and 1,8-naphthyrid-7-yl.

In the present specification the term "pharmaceutically acceptable salt" of a compound of formula (I) takes its ordinary meaning and includes any acid addition salt of a compound of formula (I), including salts formed with inorganic acids (for example hydrochloric, hydrobromic, nitric, sulphuric or phosphoric acid) or with organic acids, such as organic carboxylic acids (for example fumaric, pyruvic, lactobionic, glycolic, oxalic, maleic, hydroxymaleic, malic, citric, succinic, salicylic, o-acetoxybenzoic or tartaric acid), or organic sulphonic acids (for example toluene-p-sulphonic, bisethanesulphonic or methanesulphonic acid). The dihydrochloride, fumarate, succinate and tartrate salts are preferred. The L-tartrate salt is most preferred.

In the present specification the term "treatment of the human or animal body by therapy" includes both curative and prophylactic therapeutic treatment.

In the above definitions, similar terms specifying different numbers of C atoms take an analogous meaning.

In all embodiments of the present invention, it is preferred that n is 1.

When n is 2 or 3, each of the two or three occurrences of R2 is independently selected from H and $C_1$-$C_4$alkyl. In all embodiments of the present invention, it is preferred that R2 is H.

In all embodiments of the present invention, it is preferred that R3 is H.

In all embodiments of the present invention, it is preferred that R4 is H.

In all embodiments of the present invention, it is preferred that R5 is H.

In all embodiments of the present invention, it is preferred that R1 is $C_2$-$C_6$alkyl, $C_2$-$C_6$alkenyl, $C_3$-$C_6$cycloalkyl or $C_4$-$C_8$cycloalkylalkyl, wherein one —$CH_2$— within any cycloalkyl moiety is optionally substituted by —O— and wherein each group is optionally substituted with from 1 to 3 halogen atoms or a hydroxy, cyano, $C_1$-$C_4$alkylthio (optionally substituted with from 1 to 3 halogen atoms) or $C_1$-$C_4$alkoxy (optionally substituted with from 1 to 3 halogen atoms) radical. More preferably, R1 is $C_2$-$C_6$alkyl, $C_2$-$C_6$alkenyl, $C_3$-$C_6$cycloalkyl or $C_4$-$C_8$cycloalkylalkyl, wherein one —$CH_2$— within any cycloalkyl moiety is optionally substituted by —O— and wherein each group is optionally substituted with from 1 to 3 halogen atoms or a hydroxy, cyano, methylthio, methoxy, trifluoromethoxy, ethoxy, or isopropoxy radical. More preferably, R1 is $C_2$-$C_6$alkyl (optionally substituted with from 1 to 3 halogen atoms or a hydroxy, cyano, methylthio, methoxy, trifluoromethoxy, ethoxy, or isopropoxy radical), $C_2$-$C_6$alkenyl, $C_3$-$C_6$cycloalkyl or $C_4$-$C_8$cycloalkylalkyl (optionally substituted with a halogen atom or hydroxy radical), wherein one —$CH_2$— within any cycloalkyl moiety is optionally substituted by —O—. Suitable $C_2$-$C_6$alkyl groups (optionally substituted with from 1 to 3 halogen atoms or a hydroxy, cyano, methylthio, methoxy, trifluoromethoxy, ethoxy, or isopropoxy radical) include, for example, ethyl, 2-cyanoethyl, 2-hydroxyethyl, 2-methoxyethyl, 2-trifluoromethoxyethyl, 2-methylthioethyl, 2-ethoxyethyl, 2-isopropoxyethyl, 2,2,2-trifluoroethyl, n-propyl, isopropyl, 3-methoxypropyl, 3-hydroxypropyl, 3-cyanopropyl, 3,3,3-trifluoropropyl, n-butyl, isobutyl, 4-methoxybutyl, 4,4,4-trifluorobutyl, 2-methoxy-2-methylpropyl, 2-hydroxy-2-methylpropyl, 2-cyano-2-methylpropyl, n-pentyl, 3-methylbutyl, 3-cyano-3-methylbutyl, 3-hydroxy-3-methylbutyl, 1,2-dimethylpropyl, 2,2-dimethylpropyl, 2,2-dimethyl-3-hydroxypropyl,1-ethylpropyl, 3,3-dimethylbutyl, 2-ethylbutyl and 2-methylpentyl. Suitable $C_2$-$C_6$alkenyl groups include, for example, 2-methyl-2-propenyl. Suitable $C_3$-$C_6$cycloalkyl groups wherein one —$CH_2$— within the cycloalkyl moiety is optionally substituted by —O— include, for example, cyclopentyl and tetrahydro-2H-pyran-4-yl. Suitable $C_4$-$C_8$cycloalkylalkyl groups (optionally substituted with a halogen atom or hydroxy radical) wherein one —$CH_2$— within the cycloalkyl moiety is optionally substituted by —O— include, for example, cycloheptylmethyl, cyclohexylmethyl, tetrahydro-2H-pyran-4-ylmethyl, cyclopentylmethyl, hydroxycyclopentylmethyl, cyclobutylmethyl, cyclopropylmethyl and fluorocyclopropylmethyl.

Alternatively, in all embodiments of the present invention, it is preferred that R1 is a $C_2$-$C_{10}$alkyl group optionally substituted with from 1 to 7 halogen substituents and/or with from 1 to 3 substituents each independently selected from hydroxy, cyano, $C_1$-$C_4$alkyl, $C_1$-$C_4$alkylthio (optionally substituted with from 1 to 3 halogen atoms) and $C_1$-$C_4$alkoxy (optionally substituted with from 1 to 3 halogen atoms). More preferably, R1 is a $C_2$-$C_{10}$alkyl group optionally substituted with from 1 to 7 halogen substituents and/or with from 1 to 3 substituents each independently selected from hydroxy, cyano, $C_1$-$C_4$alkylthio (optionally substituted with from 1 to 3 halogen atoms) and $C_1$-$C_4$alkoxy (optionally substituted with from 1 to 3 halogen atoms). More preferably, R1 is a $C_2$-$C_{10}$alkyl group optionally substituted with from 1 to 3 substituents each independently selected from halogen, hydroxy, cyano, $C_1$-$C_4$alkylthio and $C_1$-$C_4$alkoxy (optionally substituted with from 1 to 3 fluorine atoms). More preferably, R1 is $C_2$-$C_6$alkyl optionally substituted with from 1 to 3 halogen atoms or a hydroxy, cyano, methylthio, methoxy, trifluoromethoxy, ethoxy, or isopropoxy radical. Still more preferably, R1 is $C_2$-$C_6$alkyl optionally substituted with from 1 to 3 fluorine atoms or a hydroxy, cyano, methylthio, methoxy, trifluoromethoxy, ethoxy, or isopropoxy radical. Still more preferably, R1 is selected from ethyl, 2-cyanoethyl, 2-hydroxyethyl, 2-methoxyethyl, 2-trifluoromethoxyethyl, 2-methylthioethyl, 2-ethoxyethyl, 2-isopropoxyethyl, 2,2,2-trifluoroethyl, n-propyl, isopropyl, 3-methoxypropyl, 3-hydroxypropyl, 3-cyanopropyl, 3,3,3-trifluoropropyl, n-butyl, isobutyl, 1-methylpropyl, 4-methoxybutyl, 4,4,4-trifluorobutyl, 2-methoxy-2-methylpropyl, 2-hydroxy-2-methylpropyl, 2-cyano-2-methylpropyl, n-pentyl, 3-methylbutyl, 3-cyano-3-methylbutyl, 3-hydroxy-3-methylbutyl, 1,2-dimethylpropyl, 2,2-dimethylpropyl, 2,2-dimethyl-3-hydroxypropyl,1-ethylpropyl, 3,3-dimethylbutyl, 2-ethylbutyl and 2-methylpentyl. Still more preferably, R1 is selected from n-propyl, n-butyl, isobutyl, 1-methylpropyl, 3-methylbutyl, 3-methoxypropyl, 3-hydroxypropyl, 3-cyanopropyl, 4-methoxybutyl, 2-hydroxy-2-methylpropyl, 2-cyano-2-methylpropyl, 2,2-dimethyl-3-hydroxypropyl and 3-cyano-3-methylbutyl. Most preferably, R1 is selected from n-propyl, n-butyl, isobutyl, 1-methylpropyl, 2-hydroxy-2-methylpropyl and 3-methylbutyl.

Alternatively, in all embodiments of the present invention, it is preferred that R1 is a $C_2$-$C_{10}$alkenyl group optionally substituted with from 1 to 7 halogen substituents and/or with from 1 to 3 substituents each independently selected from hydroxy, cyano, $C_1$-$C_4$alkyl, $C_1$-$C_4$alkylthio (optionally substituted with from 1 to 3 halogen atoms) and $C_1$-$C_4$alkoxy (optionally substituted with from 1 to 3 halogen atoms). More preferably, R1 is a $C_2$-$C_{10}$alkenyl group optionally substituted with from 1 to 7 halogen substituents and/or with from 1 to 3 substituents each independently selected from hydroxy, cyano, $C_1$-$C_4$alkylthio (optionally substituted with from 1 to 3 halogen atoms) and $C_1$-$C_4$alkoxy (optionally substituted with from 1 to 3 halogen atoms). More preferably, R1 is a $C_2$-$C_{10}$alkenyl group optionally substituted with from 1 to 3 substituents each independently selected from halogen, hydroxy, cyano, $C_1$-$C_4$alkylthio and $C_1$-$C_4$alkoxy (optionally substituted with from 1 to 3 fluorine atoms). More preferably R1 is $C_2$-$C_6$alkenyl optionally substituted with from 1 to 3 halogen atoms or a hydroxy, cyano, methylthio, methoxy, trifluoromethoxy, ethoxy, or isopropoxy radical. Still more preferably R1 is $C_2$-$C_6$alkenyl. Still more preferably, R1 is 2-methyl-2-propenyl.

Alternatively, in all embodiments of the present invention, it is preferred that R1 is a $C_3$-$C_8$cycloalkyl group, wherein one —$CH_2$— within the cycloalkyl moiety is optionally substituted by —O— or —S— and wherein the group is optionally substituted with from 1 to 7 halogen substituents and/or with from 1 to 3 substituents each independently selected from hydroxy, cyano, $C_1$-$C_4$alkyl, $C_1$-$C_4$alkylthio (optionally substituted with from 1 to 3 halogen atoms) and $C_1$-$C_4$alkoxy (optionally substituted with from 1 to 3 halogen atoms). More preferably, R1 is a $C_3$-$C_8$cycloalkyl group, wherein one —$CH_2$— within the cycloalkyl moiety is optionally substituted by —O— or —S—. More preferably, R1 is a $C_4$-$C_6$cycloalkyl group, wherein one —$CH_2$— within the cycloalkyl moiety is optionally substituted by —O— or —S—. Still more preferably, R1 is cyclopentyl or tetrahydro-2H-pyran-4-yl Alternatively, in all embodiments of the present invention, it is preferred that R1 is a $C_3$-$C_8$cycloalkenyl group optionally substituted with from 1 to 7 halogen substituents and/or with from 1 to 3 substituents each independently selected from hydroxy, cyano, $C_1$-$C_4$alkyl, $C_1$-$C_4$alkylthio (optionally substituted with from 1 to 3 halogen atoms) and $C_1$-$C_4$alkoxy (optionally substituted with from 1 to 3 halogen atoms).

Alternatively, in all embodiments of the present invention, it is preferred that R1 is a $C_4$-$C_{10}$cycloalkylalkyl group, wherein one —$CH_2$— within the cycloalkyl moiety is optionally substituted by —O— or —S— and wherein the group is optionally substituted with from 1 to 7 halogen substituents and/or with from 1 to 3 substituents each independently selected from hydroxy, cyano, $C_1$-$C_4$alkyl, $C_1$-$C_4$alkylthio (optionally substituted with from 1 to 3 halogen atoms) and $C_1$-$C_4$alkoxy (optionally substituted with from 1 to 3 halogen atoms). More preferably, R1 is a $C_4$-$C_{10}$cycloalkylalkyl group, wherein one —$CH_2$— within the cycloalkyl moiety is optionally substituted by —O— or —S— and wherein the group is optionally substituted with from 1 to 3 substituents each independently selected from halogen, hydroxy, cyano, $C_1$-$C_2$alkyl, $C_1$-$C_2$alkylthio (optionally substituted with from 1 to 3 halogen atoms) and $C_1$-$C_2$alkoxy (optionally substituted with from 1 to 3 halogen atoms). More preferably, R1 is a $C_4$-$C_8$cycloalkylalkyl group (optionally substituted with a halogen atom or hydroxy radical) wherein one —$CH_2$— within the cycloalkyl moiety is optionally substituted by —O—. Still more preferably, R1 is cycloheptylmethyl, cyclohexylmethyl, tetrahydro-2H-pyran-4-ylmethyl, cyclopentylmethyl, hydroxycyclopentylmethyl, cyclobutylmethyl, cyclopropylmethyl or fluorocyclopropylmethyl. Most preferably, R1 is cyclopropylmethyl.

Alternatively, in all embodiments of the present invention, it is preferred that R1 is a $C_4$-$C_{10}$cycloalkenylalkyl group optionally substituted with from 1 to 7 halogen substituents and/or with from 1 to 3 substituents each independently selected from hydroxy, cyano, $C_1$-$C_4$alkyl, $C_1$-$C_4$alkylthio (optionally substituted with from 1 to 3 halogen atoms) and $C_1$-$C_4$alkoxy (optionally substituted with from 1 to 3 halogen atoms).

In all embodiments of the present invention, it is preferred that Heteroaryl is a 5- or 6-membered monocyclic heteroaromatic group optionally substituted with 1, 2, 3 or 4 substituents (depending on the number of available substitution positions) each independently selected from halo, cyano, $C_1$-$C_4$ alkyl (optionally substituted with 1, 2 or 3 F atoms), $C_1$-$C_4$alkoxy (optionally substituted with 1, 2 or 3 F atoms) and $C_1$-$C_4$alkylthio (optionally substituted with 1, 2 or 3 F atoms) and/or with 1 substituent selected from pyridinyl, pyrazolyl, phenyl (optionally substituted with 1, 2 or 3 halo substituents), benzyl (optionally substituted with 1, 2 or 3 halo substituents) and phenoxy (optionally substituted with 1, 2 or 3 halo substituents) with the proviso that only $C_1$-$C_4$alkyl may be a substituent for the H of any —NH— moiety present within the group. More preferably, Heteroaryl is a 5- or 6-membered monocyclic heteroaromatic group optionally substituted with 1 or 2 substituents (depending on the number of available substitution positions) each independently selected from halo, $C_1$-$C_4$ alkyl (optionally substituted with 1, 2 or 3 F atoms) and $C_1$-$C_4$alkoxy (optionally substituted with 1, 2 or 3 F atoms) with the proviso that only $C_1$-$C_4$alkyl may be a substituent for the H of any —NH— moiety present within the group. Still more preferably, Heteroaryl is a pyrrolyl, furanyl, thienyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl or triazinyl group each of which is optionally substituted with 1 or 2 substituents each independently selected from halo, $C_1$-$C_4$ alkyl (optionally substituted with 1, 2 or 3 F atoms) and $C_1$-$C_4$alkoxy (optionally substituted with 1, 2 or 3 F atoms) with the proviso that only $C_1$-$C_4$alkyl may be a substituent for the H of any —NH— moiety present within the group. Still more preferably, Heteroaryl is a furanyl, thienyl, pyrazolyl, thiazolyl or pyridinyl group each of which is optionally substituted with 1 or 2 substituents each independently selected from halo, $C_1$-$C_2$alkyl (optionally substituted with 1, 2 or 3 F atoms) and $C_1$-$C_2$alkoxy (optionally substituted with 1, 2 or 3 F atoms) with the proviso that only $C_1$-$C_2$alkyl may be a substituent for the H of any —NH— moiety present within the group. Most preferably, Heteroaryl is selected from furan-2-yl, 2-methylfuran-3-yl, thien-2-yl, thien-3-yl, 3-methylthien-2-yl, 2,5-dichlorothien-3-yl, 1,3-dimethyl-1H-pyrazol-4-yl, 1,3-dimethyl-1H-pyrazol-5-yl, 1-methyl-3-trifluoromethyl-1H-pyrazol-4-yl, 1,3-thiazol-2-yl, 1,3-thiazol-4-yl, 4-chloro-1,3-thiazol-5-yl, 2,4-dimethyl-1,3-thiazol-5-yl, 2,4-dichloro-1,3-thiazol-5-yl, 2-methyl-4-chloro-1,3-thiazol-5-yl, 2-methoxy-4-chloro-1,3-thiazol-5-yl and 6-methylpyridin-2-yl.

Alternatively, in all embodiments of the present invention, it is preferred that Heteroaryl is an 8-, 9- or 10-membered bicyclic heteroaromatic group optionally substituted with 1, 2, 3, 4, 5 or 6 substituents (depending on the number of available substitution positions) each independently selected from halo, cyano, $C_1$-$C_4$ alkyl (optionally substituted with 1, 2 or 3 F atoms), $C_1$-$C_4$alkoxy (optionally substituted with 1, 2 or 3 F atoms) and $C_1$-$C_4$alkylthio (optionally substituted with 1, 2 or 3 F atoms) with the proviso that only $C_1$-$C_4$alkyl may be a substituent for the H of any —NH— moiety present within the group. More preferably, Heteroaryl is an 8-, 9- or 10-membered bicyclic heteroaromatic group optionally substituted with 1 or 2 substituents (depending on the number of available substitution positions) each independently selected from halo, $C_1$-$C_4$ alkyl (optionally substituted with 1, 2 or 3 F atoms) and $C_1$-$C_4$alkoxy (optionally substituted with 1, 2 or 3 F atoms) with the proviso that only $C_1$-$C_4$alkyl may be a substituent for the H of any —NH— moiety present within the group. Still more preferably, Heteroaryl is an imidazo[2,1-b][1,3]thiazolyl, indolyl, isoindolyl, benzofuranyl (also called benzo[b]furanyl), isobenzofuranyl (also called benzo[c]furanyl), benzothienyl (also called benzo[b]thienyl), isobenzothienyl (also called benzo[c]thienyl), indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridyl, purinyl, quinolinyl, isoquinolinyl, cinnolinyl, quinazolinyl, 1,4-naphthyridyl, 1,5-naphthyridyl, 1,6-naphthyridyl, 1,7-naphthyridyl or 1,8-naphthyridyl group each of which is optionally substituted with 1 or 2 substituents each independently selected from halo, $C_1$-$C_4$ alkyl (optionally substituted with 1, 2 or 3 F atoms) and $C_1$-$C_4$alkoxy (optionally substituted with 1, 2 or 3 F atoms) with the proviso that only $C_1$-$C_4$alkyl may be a substituent for the H of any —NH— moiety present within the group. Still more preferably, Heteroaryl is an imidazo[2,1-b][1,3]thiazolyl, indolyl, benzofuranyl (also called benzo

[b]furanyl), benzothienyl (also called benzo[b]thienyl), 1,3-benzothiazolyl, 2,1,3-benzothiadiazolyl, quinolinyl or isoquinolinyl group each of which is optionally substituted with 1 or 2 substituents each independently selected from halo, $C_1$-$C_4$ alkyl (optionally substituted with 1, 2 or 3 F atoms) and $C_1$-$C_4$alkoxy (optionally substituted with 1, 2 or 3 F atoms) with the proviso that only $C_1$-$C_4$alkyl may be a substituent for the H of any —NH— moiety present within the group. Most preferably, Heteroaryl is selected from 6-chloroimidazo[2,1-b][1,3]thiazol-5-yl, 1-methyl-1H-indol-2-yl, benzofuran-2-yl, benzothien-3-yl, benzothien-5-yl, benzothien-7-yl, 3-methylbenzothien-2-yl, 3-chlorobenzothien-2-yl, 1,3-benzothiazol-2-yl, 2,1,3-benzothiadiazol-4-yl, quinolin-2-yl, quinolin-3-yl, quinolin-4-yl, quinolin-8-yl, isoquinolin-1-yl, isoquinolin-3-yl or isoquinolin-4-yl.

A preferred sub-group (Group A) of novel compounds of the present invention are represented by formula (Ia)

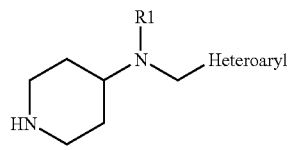

(Ia)

wherein

R1 is $C_2$-$C_{10}$alkyl, $C_2$-$C_{10}$alkenyl, $C_3$-$C_8$cycloalkyl, $C_3$-$C_8$cycloalkenyl, $C_4$-$C_{10}$cycloalkylalkyl or $C_4$-$C_{10}$cycloalkenylalkyl wherein one —$CH_2$— within any cycloalkyl moiety is optionally substituted by —O— or —S— and wherein each group is optionally substituted with from 1 to 7 halogen substituents and/or with from 1 to 3 substituents each independently selected from hydroxy, cyano, $C_1$-$C_4$alkyl, $C_1$-$C_4$alkylthio (optionally substituted with from 1 to 3 halogen atoms) and $C_1$-$C_4$alkoxy (optionally substituted with from 1 to 3 halogen atoms); and Heteroaryl is
(i) a 5- or 6-membered monocyclic heteroaromatic group optionally substituted with 1, 2, 3 or 4 substituents (depending on the number of available substitution positions) each independently selected from halo, cyano, $C_1$-$C_4$alkyl (optionally substituted with 1, 2 or 3 F atoms), $C_1$-$C_4$alkoxy (optionally substituted with 1, 2 or 3 F atoms) and $C_1$-$C_4$alkylthio (optionally substituted with 1, 2 or 3 F atoms) and/or with 1 substituent selected from pyridinyl, pyrazolyl, phenyl (optionally substituted with 1, 2 or 3 halo substituents), benzyl (optionally substituted with 1, 2 or 3 halo substituents) and phenoxy (optionally substituted with 1, 2 or 3 halo substituents) with the proviso that only $C_1$-$C_4$alkyl may be a substituent for the H of any —NH— moiety present within the group, or
(ii) an 8-, 9- or 10-membered bicyclic heteroaromatic group optionally substituted with 1, 2, 3, 4, 5 or 6 substituents (depending on the number of available substitution positions) each independently selected from halo, cyano, $C_1$-$C_4$alkyl (optionally substituted with 1, 2 or 3 F atoms), $C_1$-$C_4$alkoxy (optionally substituted with 1, 2 or 3 F atoms) and $C_1$-$C_4$alkylthio (optionally substituted with 1, 2 or 3 F atoms) with the proviso that only $C_1$-$C_4$alkyl may be a substituent for the H of any —NH— moiety present within the group;

or a pharmaceutically acceptable salt thereof, with the proviso that the compounds

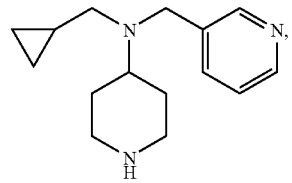

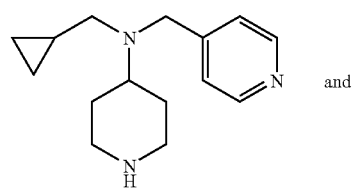

and

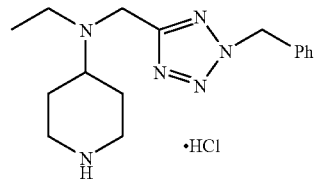

are excluded.

A more preferred sub-group (Group B) of novel compounds of the present invention are those of formula (Ia) above wherein:

R1 is $C_2$-$C_6$alkyl, $C_2$-$C_6$alkenyl, $C_3$-$C_6$cycloalkyl or $C_4$-$C_8$cycloalkylalkyl, wherein one —$CH_2$— within any cycloalkyl moiety is optionally substituted by —O— and wherein each group is optionally substituted with from 1 to 3 halogen atoms or a hydroxy, cyano, $C_1$-$C_4$alkylthio (optionally substituted with from 1 to 3 halogen atoms) or $C_1$-$C_4$alkoxy (optionally substituted with from 1 to 3 halogen atoms) radical; and Heteroaryl is
(i) a 5- or 6-membered monocyclic heteroaromatic group optionally substituted with 1 or 2 substituents (depending on the number of available substitution positions) each independently selected from halo, $C_1$-$C_4$ alkyl (optionally substituted with 1, 2 or 3 F atoms) and $C_1$-$C_4$alkoxy (optionally substituted with 1, 2 or 3 F atoms) with the proviso that only $C_1$-$C_4$alkyl may be a substituent for the H of any —NH— moiety present within the group; or
(ii) an 8-, 9- or 10-membered bicyclic heteroaromatic group optionally substituted with 1 or 2 substituents (depending on the number of available substitution positions) each independently selected from halo, $C_1$-$C_4$ alkyl (optionally substituted with 1, 2 or 3 F atoms) and $C_1$-$C_4$alkoxy (optionally substituted with 1, 2 or 3 F atoms) with the proviso that only $C_1$-$C_4$alkyl may be a substituent for the H of any —NH— moiety present within the group;

or a pharmaceutically acceptable salt thereof, with the proviso that the compounds

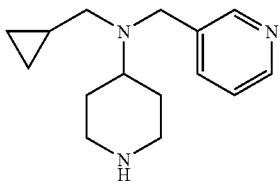

and

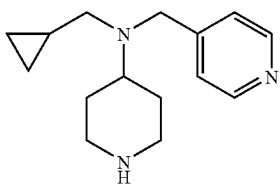

are excluded.

A still more preferred sub-group (Group C) of novel compounds of the present invention are those of formula (Ia) above wherein:

R1 is $C_2$-$C_6$alkyl, $C_2$-$C_6$alkenyl, $C_3$-$C_6$cycloalkyl or $C_4$-$C_7$cycloalkylalkyl, wherein one —$CH_2$— within any cycloalkyl moiety is optionally substituted by —O— and wherein each group is optionally substituted with from 1 to 3 halogen atoms or a hydroxy, cyano, methylthio, methoxy, trifluoromethoxy, ethoxy, or isopropoxy radical; and Heteroaryl is (i) a pyrrolyl, furanyl, thienyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl or triazinyl group optionally substituted with 1 or 2 substituents each independently selected from halo, $C_1$-$C_4$alkyl (optionally substituted with 1, 2 or 3 F atoms) and $C_1$-$C_4$alkoxy (optionally substituted with 1, 2 or 3 F atoms) with the proviso that only $C_1$-$C_4$alkyl may be a substituent for the H of any —NH— moiety present within the group; or (ii) an imidazo[2,1-b][1,3]thiazolyl, indolyl, isoindolyl, benzofuranyl (also called benzo[b]furanyl), isobenzofuranyl (also called benzo[c]furanyl), benzothienyl (also called benzo[b]thienyl), isobenzothienyl (also called benzo[c]thienyl), indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzisoxazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, quinolinyl, isoquinolinyl, cinnolinyl, quinazolinyl, 1,4-naphthyridyl, 1,5-naphthyridyl, 1,6-naphthyridyl, 1,7-naphthyridyl or 1,8-naphthyridyl group optionally substituted with 1 or 2 substituents each independently selected from halo, $C_1$-$C_4$ alkyl (optionally substituted with 1, 2 or 3 F atoms) and $C_1$-$C_4$alkoxy (optionally substituted with 1, 2 or 3 F atoms) with the proviso that only $C_1$-$C_4$alkyl may be a substituent for the H of any —NH— moiety present within the group;

or a pharmaceutically acceptable salt thereof, with the proviso that the compounds

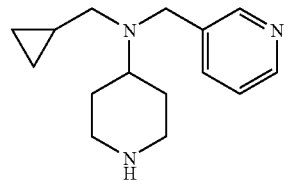

and

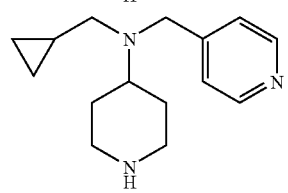

are excluded.

A still more preferred sub-group (Group D) of novel compounds of the present invention are those of formula (Ia) above wherein:

R1 is $C_2$-$C_6$alkyl (optionally substituted with from 1 to 3 halogen atoms or a hydroxy, cyano, methylthio, methoxy, trifluoromethoxy, ethoxy, or isopropoxy radical), $C_2$-$C_6$alkenyl, $C_3$-$C_6$cycloalkyl or $C_4$-$C_8$cycloalkylalkyl (optionally substituted with a halogen atom or hydroxy radical), wherein one —$CH_2$— within any cycloalkyl moiety is optionally substituted by —O—; and Heteroaryl is (i) a furanyl, thienyl, pyrazolyl, thiazolyl or pyridinyl group optionally substituted with 1 or 2 substituents each independently selected from halo, $C_1$-$C_2$alkyl (optionally substituted with 1, 2 or 3 F atoms) and $C_1$-$C_2$alkoxy (optionally substituted with 1, 2 or 3 F atoms) with the proviso that only $C_1$-$C_2$alkyl may be a substituent for the H of any —NH— moiety present within the group; or (ii) an imidazo[2,1-b][1,3]thiazolyl, indolyl, benzofuranyl (also called benzo[b]furanyl), benzothienyl (also called benzo[b]thienyl), 1,3-benzothiazolyl, 2,1,3-benzothiadiazolyl, quinolinyl or isoquinolinyl group optionally substituted with 1 or 2 substituents each independently selected from halo, $C_1$-$C_4$ alkyl (optionally substituted with 1, 2 or 3 F atoms) and $C_1$-$C_4$alkoxy (optionally substituted with 1, 2 or 3 F atoms) with the proviso that only $C_1$-$C_4$alkyl may be a substituent for the H of any —NH— moiety present within the group;

or a pharmaceutically acceptable salt thereof, with the proviso that the compounds

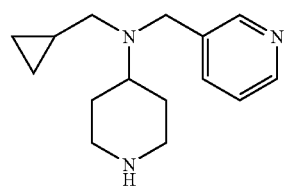

and

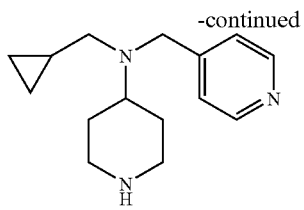
-continued are excluded.

A still more preferred sub-group (Group E) of novel compounds of the present invention are those of formula (Ia) above wherein:

R1 is ethyl, 2-cyanoethyl, 2-hydroxyethyl, 2-methoxyethyl, 2-trifluoromethoxyethyl, 2-methylthioethyl, 2-ethoxyethyl, 2-isopropoxyethyl, 2,2,2-trifluoroethyl, n-propyl, isopropyl, 3-methoxypropyl, 3-hydroxypropyl, 3-cyanopropyl, 3,3,3-trifluoropropyl, n-butyl, isobutyl, 4-methoxybutyl, 4,4,4-trifluorobutyl, 2-methoxy-2-methylpropyl, 2-hydroxy-2-methylpropyl, 2-cyano-2-methylpropyl, n-pentyl, 3-methylbutyl, 3-cyano-3-methylbutyl, 3-hydroxy-3-methylbutyl, 1,2-dimethylpropyl, 2,2-dimethylpropyl, 2,2-dimethyl-3-hydroxypropyl,1-ethylpropyl, 3,3-dimethylbutyl, 2-ethylbutyl, 2-methylpentyl, 2-methyl-2-propenyl, cyclopentyl, tetrahydro-2H-pyran-4-yl, cycloheptylmethyl, cyclohexylmethyl, tetrahydro-2H-pyran-4-ylmethyl, cyclopentylmethyl, hydroxycyclopentylmethyl, cyclobutylmethyl, cyclopropylmethyl or fluorocyclopropylmethyl; and Heteroaryl is (i) a furan-2-yl, 2-methylfuran-3-yl, thien-2-yl, thien-3-yl, 3-methylthien-2-yl, 2,5-dichlorothien-3-yl, 1,3-dimethyl-1H-pyrazol-4-yl, 1,3-dimethyl-1H-pyrazol-5-yl, 1-methyl-3-trifluoromethyl-1H-pyrazol-4-yl, 1,3-thiazol-2-yl, 1,3-thiazol-4-yl, 4-chloro-1,3-thiazol-5-yl, 2,4-dimethyl-1,3-thiazol-5-yl, 2,4-dichloro-1,3-thiazol-5-yl, 2-methyl-4-chloro-1,3-thiazol-5-yl, 2-methoxy-4-chloro-1,3-thiazol-5-yl or 6-methylpyridin-2-yl group; or (ii) a 6-chloroimidazo[2,1-b][1,3]thiazolyl, 1-methyl-1H-indol-2-yl, benzofuran-2-yl, benzothien-3-yl, benzothien-5-yl, benzothien-7-yl, 3-methylbenzothien-2-yl, 3-chlorobenzothien-2-yl, 1,3-benzothiazol-2-yl, 2,1,3-benzothiadiazol-4-yl, quinolin-2-yl, quinolin-3-yl, quinolin-4-yl, quinolin-8-yl, isoquinolin-1-yl, isoquinolin-3-yl or isoquinolin-4-yl group;

or a pharmaceutically acceptable salt thereof.

Particularly preferred compounds of the present invention include:

N-(2-Methylpropyl)-N-{[3-methylthien-2-yl]methyl}piperidin-4-amine,
N-(2-Methylpropyl)-N-{[3-methyl-1-benzothien-2-yl]methyl}piperidin-4-amine,
N-(2-Methylpropyl)-N-{[benzothien-3-yl]methyl}piperidin-4-amine,
N-(2-Methylpropyl)-N-{[thieny-2-yl]methyl}piperidin-4-amine,
N-(2-Methylpropyl)-N-{[thieny-3-yl]methyl}piperidin-4-amine,
N-(2-Methylpropyl)-N-{[furan-2-yl]methyl}piperidin-4-amine,
N-(2-Methylpropyl)-N-{[6-methylpyridin-2-yl]methyl}piperidin-4-amine,
N-(2-Methylpropyl)-N-{[(1-benzothien-7-yl]methyl}piperidin-4-amine,
N-(2-Methylpropyl)-N-{[(quinolin-3-yl)methyl}piperidin-4-amine,
N-(2-Methylpropyl)-N-{[(quinolin-4-yl)methyl}piperidin-4-amine,
N-(2-Methylpropyl)-N-{[(1,3-benzothiazol-2-yl)methyl}piperidin-4-amine,
N-(2-Methylpropyl)-N-{[(6-chloroimidazo[2,1-b][1,3]thiazol-5-yl)methyl}piperidin-4amine,
N-(2-Methylpropyl)-N-{[(1-benzothien-5-yl)methyl}piperidin-4-amine,
N-(2-Methylpropyl)-N-{[(1-methyl-1H-indol-2-yl)methyl}piperidin-4-amine,
N-(2-Methylpropyl)-N-{[(isoquinolin-4-yl)methyl}piperidin-4-amine,
N-(2-Methylpropyl)-N-{[(quinolin-8-yl)methyl}piperidin-4-amine,
N-(2-Methylpropyl)-N-{[(1,3-thiazol-4-yl)methyl}piperidin-4-amine,
N-(2-Methylpropyl)-N-{[(2,4-dichloro-1,3-thiazol-5-yl)methyl}piperidin-4-amine,
N-(2-Methylpropyl)-N-{[(2,1,3-benzothiadiazol-4-yl)methyl}piperidin-4-amine,
N-(2-Methylpropyl)-N-{[(quinolin-2-yl)methyl}piperidin-4-amine,
N-(2-Methylpropyl)-N-{[(2,5-dichlorothien-3-yl)methyl]}piperidin-4-amine,
N-(2-Methylpropyl)-N-{[(1,3-dimethyl-1H-pyrazol-5-yl)methyl]}piperidin-4-amine,
N-(2-Methylpropyl)-N-{[(3-chloro-1-benzothien-2-yl)methyl]}piperidin-4-amine,
N-(2-Methylpropyl)-N-{[(isoquinolin-1-yl)methyl]}piperidin-4-amine,
N-(2-Methylpropyl)-N-{[(isoquinolin-3-yl)methyl]}piperidin-4-amine,
N-(2-Methylpropyl)-N-{[(1,3-dimethyl-1H-pyrazol-4-yl)methyl]}piperidin-4-amine,
N-(2-Methylpropyl)-N-{[(1-methyl-3-(trifluoromethyl)-1-pyrazol-4-yl)methyl]}piperidin-4-amine,
N-(2-Methylpropyl)-N-{[(2-methylfuran-3-yl)methyl]}piperidin-4-amine,
N-(2-Methylpropyl)-N-{[(2,4-dimethyl-1,3-thiazol-5-yl)methyl}piperidin-4-amine,
N-(2-Methylpropyl)-N-{[(2-methoxy-4-chloro-1,3-thiazol-5-yl)methyl}piperidin-4-amine,
N-(2-Methylpropyl)-N-{[(2-methyl-4-chloro-1,3-thiazol-5-yl)methyl}piperidin-4-amine,
N-(Cyclopropylmethyl)-N-{[(2,4-dimethyl-1,3-thiazol-5-yl)methyl}piperidin-4-amine,
N-(Cyclopropylmethyl)-N-{[(4-chloro-2-methyl-1,3-thiazol-5-yl)methyl}piperidin-4-amine,
N-(Cyclopropylmethyl)-N-{[(4-chloro-2-methoxy-1,3-thiazol-5-yl)methyl}piperidin-4-amine,
N-(3-Methylbutyl)-N-{[(benzofuran-2-yl)methyl]}piperidin-4-amine,
N-(3-Methylbutyl)-N-{(1,3-thiazol-2-yl)methyl}piperidin-4-amine,
N-(2-Methylpropyl)-N-{[(4-chloro-1,3-thiazol-5-yl)methyl}piperidin-4-amine and
N-(2-Hydroxy-2-methylpropyl)-N-{[(2,4-dichloro-1,3-thiazol-5-yl)methyl}piperidin-4-amine.

It will be appreciated that certain compounds of formula I may possess one or more chiral centres. Where a structural formula does not specify the stereochemistry at one or more chiral centres, it encompasses all possible stereoisomers and all possible mixtures of stereoisomers (including, but not limited to, racemic mixtures) which may result from stereoisomerism at each of the one or more chiral centers.

As mentioned above, the compounds of the present invention and their pharmaceutically acceptable salts inhibit the uptake of one or more of the monoamine neurotransmitters serotonin, dopamine and norepinephrine.

In view of these properties, the compounds of the present invention and their pharmaceutically acceptable salts are indicated for use in treating disorders which are caused by or linked to decreased neurotransmission of one or more of these monoamines.

One preferred group of compounds of the present invention selectively inhibit the reuptake of serotonin and norepinephrine over dopamine. Preferably said group of compounds of the present invention selectively inhibit the serotonin and norepinephrine transporters relative to the dopamine transporter by a factor of at least five, and even more preferably by a factor of at least ten. Compounds of the present invention with this pharmacological profile are particularly useful for the treatment of depression, eating disorders (including bulimia and anorexia nervosa), inflammatory bowel disorders, functional bowel disorders, dyspepsia, Crohn's disease, iletis, ischemic bowel disease, ulcerative colitis, gastroesophageal reflux for functional bowel disorders, irritable bowel syndrome, obesity, insterstitial cystitis, urethral syndrome, gastric motility disorders, substance abuse (including alcoholism, tobacco abuse, symptoms caused by withdrawal or partial withdrawal from the use of tobacco or nicotine and drug addiction including cocaine abuse), pain (including inflammatory pain, neuropathic pain, non-neuropathic non-inflammatory pain, persistent pain, persistent pain of inflammatory and/or neuropathic origin, headache and migraine), incontinence (including stress urinary incontinence and urge incontinence), dementia of ageing, senile dementia, Alzheimer's, memory loss, Parkinsonism, attention-deficit disorder (including attention-deficit hyperactivity disorder), anxiety, social phobia, disruptive behavior disorders, impulsive control disorders, borderline personality disorder, chronic fatigue syndrome, panic disorders, obsessive compulsive disorder, post-traumatic stress disorder, schizophrenia, gastrointestinal disorders, cardiovascular disorders, hot flushes/flashes, emesis, sleep disorders, cognitive disorders, psychotic disorders, brain trauma, premenstrual syndrome or late luteal syndrome, sexual dysfunction (including premature ejaculation and erectile difficulty), autism, mutism and trichotilomania. They are more particularly useful for the treatment of depression, incontinence (particularly stress urinary incontinence) and pain (particularly persistent pain). They are most particularly useful for the treatment of persistent pain.

For clinical purposes, pain may be divided into two categories: acute pain and persistent pain. Acute pain is provoked by noxious stimulation produced by injury and/or disease of skin, deep somatic structures or viscera, or abnormal function of muscle or viscera that does not produce actual tissue damage. On the other hand, persistent pain can be defined as pain that persists beyond the usual course of an acute disease or a reasonable time for an injury to heal or that is associated with a chronic pathologic process that causes continuous pain or the pain recurs at intervals for months or years. If pain is still present after a cure should have been achieved, it is considered persistent pain. For the purpose of the present invention, persistent pain can be chronic non-remitting or recurrent. The difference in definition between acute and persistent pain is not merely semantic but has an important clinical relevance. For example, a simple fracture of the wrist usually remains painful for a week to 10 days. If the pain is still present beyond the typical course of treatment, it is likely that the patient is developing reflex sympathetic dystrophy, a persistent pain syndrome that requires immediate effective therapy. Early and effective intervention potentially prevents the undue disability and suffering, and avoids the potential development of a condition that becomes refractory to therapy.

Acute and persitant pain differ in etiology, mechanisms, pathophysiology, symptomatology, diagnosis, therapy, and physiological responses. In contrast to the transitory nature of acute pain, persistent pain is caused by chronic pathologic processes in somatic structures or viscera, by prolonged and sometimes permanent dysfunction of the peripheral or central nervous system, or both. Also, persistent pain can sometimes be attributed to psychologic mechanisms and/or environmental factors.

More specifically, persistent pain can be segmented into neuropathic pain (e.g. diabetic neuropathy, infectious neuropathic pain associated with AIDS, non-surgical carpal tunnel syndromes, post-herpetic neuralgia, cervical, thoracic and lumbosacral radiculopathies, stroke-related central pains, trigeminal neuralgia and complex regional pain syndromes I and II), inflammatory pain (e.g. polymyalgia, rheumatoid arthritis and osteoarthritis), and non-neuropathic non-inflammatory chronic pain (NNNICP) (e.g. chronic fatigue syndrome, chronic back pain without radiculopathy, fibromyalgia, chronic tension type headaches, inflammatory bowel disorders, irritable bowel syndrome, whiplash injuries, chronic pelvic pain, temporomandibular joint disorder (TMJD) and failed back).

Current therapies for persistent pain include opiates, barbiturate-like drugs such as thiopental sodium and surgical procedures such as neurectomy, rhizotomy, cordotomy, and cordectomy.

Another preferred group of compounds of the present invention selectively inhibit the reuptake of serotonin over norepinephrine and dopamine. Preferably said group of compounds of the present invention selectively inhibit the serotonin transporter relative to the norepinephrine and dopamine transporters by a factor of at least five, and even more preferably by a factor of at least ten. Compounds of the present invention with this pharmacological profile are particularly useful for the treatment of depression.

Another preferred group of compounds of the present invention selectively inhibit the reuptake of norepinephrine over serotonin and dopamine. Preferably said group of compounds of the present invention selectively inhibit the norepinephrine transporter relative to the serotonin and dopamine transporters by a factor of at least five, and even more preferably by a factor of at least ten. Compounds of the present invention with this pharmacological profile are particularly useful for the treatment of addictive disorder and withdrawal syndrome, an adjustment disorder (including depressed mood, anxiety, mixed anxiety and depressed mood, disturbance of conduct, and mixed disturbance of conduct and mood), an age-associated learning and mental disorder (including Alzheimer's disease), alcohol addiction, allergies (in particular allergic rhinitis), anorexia nervosa, apathy, asthma, an attention-deficit disorder (ADD) due to general medical conditions, attention-deficit hyperactivity disorder (ADHD) (optionally by combination therapy with stimulants (e.g. methylphenidate, amphetamine and dextroamphetamine)) including the predominantly inattentive type of ADHD and the predominantly hyperactive-impulsive type of ADHD, bipolar disorder, bulimia nervosa, chronic fatigue syndrome, chronic or acute stress, cognitive disorders (discussed in more detail below but including mild cognitive impairment (MCI)

and cognitive impairment associated with schizophrenia (CIAS)), communication disorders (including stuttering, expressive language disorder, mixed receptive-expressive language disorder, phonological disorder and communication disorder not otherwise specified), conduct disorder, cyclothymic disorder, dementia of the Alzheimers type (DAT), depression (including adolescent depression and minor depression), dysthymic disorder, emotional dysregulation (including emotional dysregulation associated with ADHD, borderline personality disorder, bipolar disorder, schizophrenia, schizoaffective disorder and intermittent explosive disorder), fibromyalgia and other somatoform disorders (including somatization disorder, conversion disorder, pain disorder, hypochondriasis, body dysmorphic disorder, undifferentiated somatoform disorder, and somatoform NOS), generalized anxiety disorder, hot flashes or vasomotor symptoms, hypotensive states including orthostatic hypotension, impulse control disorders (including intermittent explosive disorder, kleptomania, pyromania, pathological gambling, trichotillomania and impulse-control disorder not otherwise specified), incontinence (i.e., stress incontinence, genuine stress incontinence, mixed incontinence and bedwetting), an inhalation disorder, an intoxication disorder, learning disabilities (including developmental speech and language disorders (such as developmental articulation disorder, developmental expressive language disorder and developmental receptive language disorder), learning disorders (such as reading disorder, mathematics disorder, disorder of written expression and learning disorder not otherwise specified) and motor skills disorders (such as developmental coordination disorder)), mania, migraine headaches, neuropathic pain, nicotine addiction, obesity (i.e., reducing the weight of obese or overweight patients), obsessive compulsive disorders and related spectrum disorders, oppositional defiant disorder, pain including chronic pain, neuropathic pain and antinociceptive pain, panic disorder, Parkinson's disease (in particular to improve dyskinesia, oscilations, balance, coordination, depression, and motivation), peripheral neuropathy, post-traumatic stress disorder, personality change due to a general medical condition (including labile type, disinhibited type, aggressive type, apathetic type, paranoid type, combined type and unspecified type), pervasive developmental disorders (including autistic disorder, Asperger's disorder, Rett's disorder, childhood disintegrative disorder, and pervasive developmental disorder not otherwise specified), premenstrual dysphoric disorder (i.e., premenstrual syndrome and late luteal phase dysphoric disorder), psoriasis, psychoactive substance use disorders, a psychotic disorder (including schizophrenia, schizoaffective and schizophreniform disorders), seasonal affective disorder, a sleep disorder (such as narcolepsy and enuresis), sexual dysfunction (defined in more detail below), social phobia (including social anxiety disorder), a specific developmental disorder, selective serotonin reuptake inhibition (SSRI) "poop out" syndrome (i.e., wherein a patient who fails to maintain a satisfactory response to SSRI therapy after an initial period of satisfactory response), TIC disorders (e.g., Tourette's Disease), tobacco addiction and vascular dementia.

The term "cognitive disorders" (also variously referred to as "cognitive failure,""cognitive insufficiency," "cognitive deficit," "cognitive impairment," "cognitive dysfunction," and the like) refers to the dysfunction, diminution, or loss of one or more cognitive functions, the processes by which knowledge is acquired, retained, and used. Cognitive dysfunction includes cognitive changes associated with ageing ("age-associated memory impairment"), as well as changes due to other causes. Cognitive impairment is most commonly due to a delirium or dementia, but can also occur in association with a number of other medical or neuropsychiatric disorders. More focal cognitive deficits are diagnosed using the criteria disclosed in the *Diagnostic and Statistical Manual of Mental Disorders,* Fourth Edition, Text Revision (DSM-IV-TR™, 2000), American Psychiatric Association, Washington, D.C., as either amnestic disorders (affecting memory) or cognitive disorder not otherwise specified (NOS), which includes executive dysfunction, visuospatial/visuoconstructional impairment, attentional deficits, disorientation, etc. These more focal cognitive disorders also have a wide variety of causes, some of which are of unknown etiology.

Sexual dysfunctions in men and women treatable with compounds of the present invention include those described in the chapter entitled "Sexual and Gender Identity Disorders" in the *Diagnostic and Statistical Manual of Mental Disorders,* Fourth Edition (2000), Text Revision (DSM-IV-TR™), American Psychiatric Association, Washington, D.C. These sexual dysfunctions are characterized by disturbances in sexual desire and psychophysiological changes characteristic of the sexual response cycle, and can include pain associated with sexual intercourse. The sexual dysfunctions include Sexual Desire Disorders (i.e., Hypoactive Sexual Desire Disorder, Sexual Aversion Disorder), Sexual Arousal Disorders (i.e., Female Sexual Arousal Disorder, Male Erectile Disorder), Orgasmic Disorders (i.e., Female Orgasmic Disorder, Male Orgasmic Disorder, Premature Ejaculation), Sexual Pain Disorders (i.e., Dyspareunia, Vaginismus), Sexual Dysfunction Due to a General Medical Condition, Substance-Induced Sexual Dysfunction, and Sexual Dysfunction Not Otherwise Specified, which includes disorders of sexual functioning not classifiable in any of the specific categories.

Disorders of sexual response can occur at one or more of the phases of the sexual response cycle, which includes desire, excitement, orgasm, and resolution.

Subtypes indicating the onset, context, and etiological factors associated with the sexual dysfunctions include Lifelong Type, Acquired Type, Generalized Type, Situational Type, Due to Psychological Factors, and Due to Combined Factors, respectively.

Sexual dysfunction caused exclusively by the physiological effects of a specified general medical condition is diagnosed as Sexual Dysfunction Due to a General Medical Condition. Sexual Dysfunction caused exclusively by the physiological effects of a drug of abuse, a medication, or toxin exposure is diagnosed as Substance-Induced Sexual Dysfunction. Sexual dysfunction due to both a general medical condition and substance use is diagnosed as Sexual Dysfunction Due to a General Medical Condition and Substance-Induced Sexual Dysfunction. A primary Sexual Dysfunction diagnosis with the subtype Due to Combined Factors is made if a combination of psychological factors and either a general medical condition or a substance is judged to have an etiological role, but no one etiology is sufficient to account for the dysfunction. If the clinician cannot determine the etiological roles of psychological factors, a general medical condition, and substance use, Sexual Dysfunction Not Otherwise Specified is diagnosed.

Sexual Desire Disorders listed in the DSM-IV-TR™ include 302.71 Hypoactive Sexual Desire Disorder and 302.79 Sexual Aversion Disorder. Sexual Arousal Disorders listed in the DSM-IV-TR™ include 302.72 Female Sexual Arousal Disorder and 302.72 Male Erectile Disorder. Orgasmic Disorders listed in the DSM-IV-TR™include 302.73 Female Orgasmic Disorder (formerly Inhibited Female Orgasm), 302.74 Male Orgasmic Disorder (formerly Inhibited Male Orgasm), and 302.75 Premature Ejaculation. Sexual Pain Disorders listed in the DSM-IV-TR™ include 302.76 Dyspareunia (Not Due to a General Medical Condition) and 306.51 Vaginismus (Not Due to a General Medical Condition). Sexual Dysfunction Due to a General Medical Condition includes a number of subtypes. The diagnostic code and term for a Sexual Dysfunction Due to a General Medical Condition listed in the DSM-IV-TR™ is selected based on the predominant Sexual Dysfunction, and include:

- 625.8 Female Hypoactive Sexual Desire Disorder Due to . . . [Indicate the General Medical Condition]. This term is used if, in a female, deficient or absent sexual desire is the predominant feature;
- 608.89 Male Hypoactive Sexual Desire Disorder Due to . . . [Indicate the General Medical Condition]. This term is used if, in a male, deficient or absent sexual desire is the predominant feature;
- 607.84 Male Erectile Disorder Due to . . . [Indicate the General Medical Condition]. This term is used if male erectile dysfunction is the predominant feature;
- 625.0 Female Dyspareunia Due to . . . [Indicate the General Medical Condition]. This term is used if, in a female, pain associated with intercourse is the predominant feature;
- 608.89 Male Dyspareunia Due to . . . [Indicate the General Medical Condition]. This term is used if, in a male, pain associated with intercourse is the predominant feature;
- 625.8 Other Female Sexual Dysfunction Due to . . . [Indicate the General Medical Condition]. This term is used if, in a female, some other feature is predominant (e.g., Orgasmic Disorder) or no feature predominates;
- 608.89 Other Male Sexual Dysfunction Due to . . . [Indicate the General Medical Condition]. This term is used if, in a male, some other feature is predominant (e.g., Orgasmic Disorder) or no feature predominates.

Substance-Induced Sexual Dysfunction specifiers are selected based on the predominant sexual dysfunction, and include:

- With Impaired Desire. This specifier is used if deficient or absent sexual desire is the predominant feature;
- With Impaired Arousal. This specifier is used if impaired sexual arousal (e.g., erectile dysfunction, impaired lubrication) is the predominant feature;
- With Impaired Orgasm. This specifier is used if impaired orgasm is the predominant feature;
- With Sexual Pain. This specifier is used if pain associated with intercourse is the predominant feature.

Substance-Induced Sexual Dysfunctions usually have their onset during Substance Intoxication, and this is indicated by noting With Onset During Intoxication. Substance-Induced Sexual Dysfunction can occur in association with intoxication with the following classes of substances: alcohol; amphetamine and related substances; cocaine; opioids; sedatives, hypnotics, and anxiolytics; and other or unknown substances. Acute intoxication with or chronic Abuse of or Dependence on substances of abuse has been reported to decrease sexual interest and cause arousal problems in both sexes. A decrease in sexual interest, arousal disorders, and orgasmic disorders may also be caused by prescribed medications including antihypertensives, histamine H2 receptor antagonists, antidepressants (especially selective serotonin reuptake inhibitors), neuroleptics, anxiolytics, anabolic steroids, and antiepileptics. Painful orgasm has been reported with fluphenazine, thioridazine, and amoxapine. Priapism has been reported with use of chlorpromazine, trazodone, and clozapine and following penile injections of papaverine or prostaglandin. Medications such as antihypertensive agents or anabolic steroids may also promote depressed or irritable mood in addition to the sexual dysfunction, and an additional diagnosis of Substance-Induced Mood Disorder may be warranted. Current clinical experience strongly suggests that Substance-Induced Sexual Dysfunction is usually generalized (i.e., not limited to certain types of stimulation, situations, or partners).

A final category listed in the DSM-IV-TR™ is 302.70 Sexual Dysfunction Not Otherwise Specified. This category includes sexual dysfunctions that do not meet criteria for any specific Sexual Dysfunction;

Another preferred group of compounds of the present invention inhibit the reuptake of norepinephrine, serotonin and dopamine. Compounds of the present invention with this pharmacological profile are particularly useful for the treatment of a variety of conditions such as depression, obesity, compulsive disorders (including bulimia, obsessive compulsive disorder, drug addiction including cocaine abuse and alcohol addiction), hypertension, senile dementia, Alzheimer's, memory loss, attention-deficit hyperactivity disorder (ADHD), sexual dysfunction, Parkinsonism, anxiety, chronic fatigue syndrome, panic disorders, cognitive disorders, schizophrenia, gastrointestinal disorders, headache, cardiovascular disorders, epilepsy, smoking cessation, pain including chronic pain, urinary incontinence, emesis and sleep disorders. They are most particularly useful for the treatment of depression, chronic pain, smoking cessation and obesity.

Accordingly, as noted above, the present invention provides a compound of formula (I) or a pharmaceutically acceptable salt thereof for use in therapy. In particular, the present invention provides a compound of formula (I) or a pharmaceutically acceptable salt thereof for use as an inhibitor of the uptake of one or more of the monoamine neurotransmitters serotonin, dopamine and norepinephrine.

As noted above, in another embodiment, the present invention provides a method for inhibiting the uptake of one or more monoamines selected from serotonin, dopamine and norepinephrine in a mammal, comprising administering to a mammal in need of such inhibition an effective amount of a compound of formula (I) or a pharmaceutically acceptable salt thereof. In particular, the present invention provides a method for treating a disorder which is caused by or linked to decreased neurotransmission of one or more monoamines selected from serotonin, dopamine and norepinephrine in a mammal, comprising administering to a mammal in need of such treatment an effective amount of a compound of formula (I) or a pharmaceutically acceptable salt thereof. Such disorders include, for example, disorders of the central and/or peripheral nervous system.

In the context of the present specification the terms "treating" and "treatment" include prophylactic treatment as well as curative treatment.

As noted above, in another alternative embodiment, the present invention provides for the use of a compound of formula (I) or a pharmaceutically acceptable salt thereof for the manufacture of a medicament for inhibiting the uptake of one or more monoamines selected from serotonin, dopamine and norepinephrine. In particular, the present invention provides for the use of a compound of formula (I) or a pharmaceutically acceptable salt thereof for the manufacture of a medicament for the treatment of a disorder which is caused by or linked to decreased neurotransmission of one or more monoamines selected from serotonin, dopamine and norepinephrine. Such disorders include, for example, disorders of the central and/or peripheral nervous system.

The compounds may be administered by various routes and are usually employed in the form of a pharmaceutical composition. Accordingly, as noted above, in a further embodiment, the present invention provides a pharmaceutical composition comprising a compound of formula (I) or a pharmaceutically acceptable salt thereof together with a pharmaceutically acceptable diluent or carrier.

Such compositions may be prepared by methods well known in the pharmaceutical art and normally comprise at least one active compound in association with a pharmaceutically acceptable diluent or carrier. In making the compositions of the present invention, the active ingredient will usually be mixed with a carrier or diluted by a carrier, and/or enclosed within a carrier which may, for example, be in the form of a capsule, sachet, paper or other container.

The compositions indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds. Compositions of the invention may be formulated so as to provide, quick, sustained or delayed release of the active ingredient after administration to the patient by employing procedures well known in the art.

The compositions are preferably formulated in a unit dosage form, each dosage containing from about 5 to about 500 mg of the active ingredient.

In the context of the present specification, the term "unit dosage form" refers to physically discrete units suitable as unitary doses for human subjects and other mammals, each unit containing a predetermined quantity of one or more compounds of formula (I) or pharmaceutically acceptable salts thereof, calculated to produce the desired therapeutic effect, together with a pharmaceutically acceptable diluent or carrier.

Compounds of formula (I) may be prepared by conventional organic chemistry techniques. When R3 is H, two possible three-step conventional syntheses are outlined in Scheme 1. In the schemes that follow, n, R1, R2, R3, R4, R5 and Heteroaryl have the meanings ascribed to them above. Additional notation used is defined in the context of each scheme.

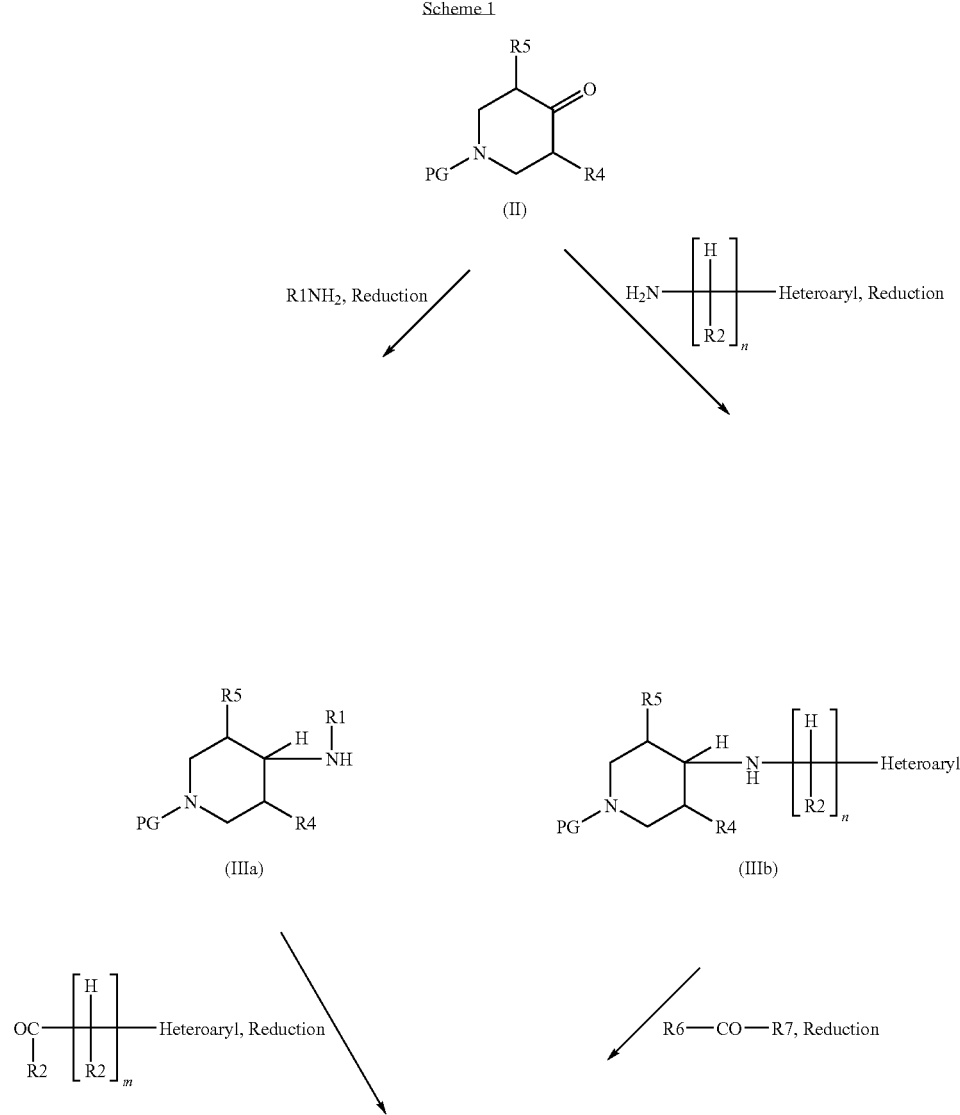

-continued

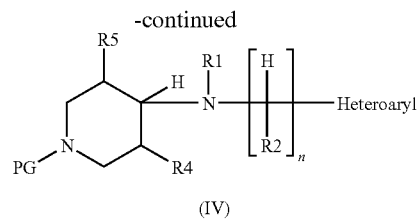

(IV)

↓ Deprotect

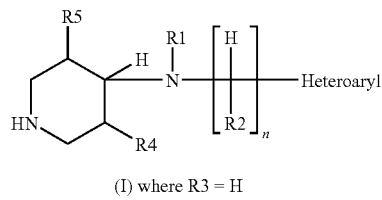

(I) where R3 = H

PG means a nitrogen protecting group, suitable examples of which will be well known to those of skill in the art as will methods for their removal. Further information on suitable N-protecting groups is contained in the well known text "Protective Groups in Organic Synthesis", Theodora W. Greene and Peter G. M. Wuts, John Wiley & Sons, Inc., New York, 1999, pp. 494-653. A preferred N-protecting group is the t-butyloxycarbonyl (BOC) group.

R6 and R7 are chosen such that R6-CH—R7=R1.

m=0, 1 or 2.

Thus, an N-protected 4-piperidone (II) undergoes reductive amination with an amine to provide a secondary 4-aminopiperidine (IIIa) or (IIIb). The secondary 4-amino-piperidine (IIIa) or (IIIb) then undergoes a second reductive amination with an aldehyde or ketone to provide a compound of formula (IV) which is an N-protected compound of formula (I). Conditions suitable for effecting reductive aminations will be known to those skilled in the art. For example, reductive conditions may be provided by hydrogenation under pressure in the presence of a Pd/C catalyst in a suitable solvent (e.g. ethanol). Alternatively, suitable reductive conditions may be provided by use of the reagent sodium triacetoxyborohydride, optionally in the presence of acetic acid, in a suitable solvent (e.g. 1,2-dichloroethane, tetrahydrofuran (THF), dichloromethane (DCM) or dimethylformamide (DMF)). The N-protecting group is then removed to provide a compound of formula (I) (where R3 is H). Where a BOC protecting group is used, this may be achieved by the use of a strong acid such as trifluoroacetic acid (TFA), optionally in the presence of anisole, or concentrated hydrochloric acid in a suitable solvent (e.g. DCM or THF). If desired, the compound of formula (I) may be converted into an acid addition salt by reaction with a suitable quantity of an acid (e.g. hydrochloric, tartaric or fumaric acid) in a suitable solvent (e.g. diethyl ether, acetonitrile, DCM, methanol, ethanol or isopropanol or mixtures thereof).

Suitable heteroaryl aldehydes for reaction with the intermediate (IIIa) may be commercially available or, alternatively, may be prepared from other commercially available reagents using standard functional group conversions. For example, aldehydes of the formula Heteroaryl-CHO may be prepared by reacting a compound of the formula Heteroaryl-Br with an organometallic reagent (e.g. butyllithium) in a suitable solvent (e.g. anhydrous THF) and then adding DMF. Alternatively, a compound of the formula Heteroaryl-$CO_2$H is reacted with 1,1'-carbonyldiimidazole in a suitable solvent (e.g. DCM) and then with N,O-dimethylhydroxylamine hydrochloride to provide an N-methyl N-methoxy heteroaryl-carboxamide which is then reacted with a reducing agent (e.g. diisobutylaluminumhydride) in a suitable solvent (e.g. toluene). Alternatively, a compound of the formula Heteroaryl-$CO_2$Me is reacted with a reducing agent (e.g. diisobutylaluminumhydride) in a suitable solvent (e.g. THF). Alternatively, tetrapropyl ammonium peruthenate is added to a mixture of a compound of the formula Heteroaryl-$CH_2$OH and N-methyl morpholine N-oxide in a suitable solvent (e.g. DCM).

It will be appreciated by those skilled in the art that the same double reductive amination approach could be used starting with a 1-N-protected 4-aminopiperidine and reacting this sequentially under reductive conditions with suitable R1 and Heteroaryl aldehyde or ketone derivatives.

As an alternative to the second reductive amination step, compound (IIIa) or (IIIb) may be subjected to an alkylation step as shown below in Scheme 2.

Scheme 2

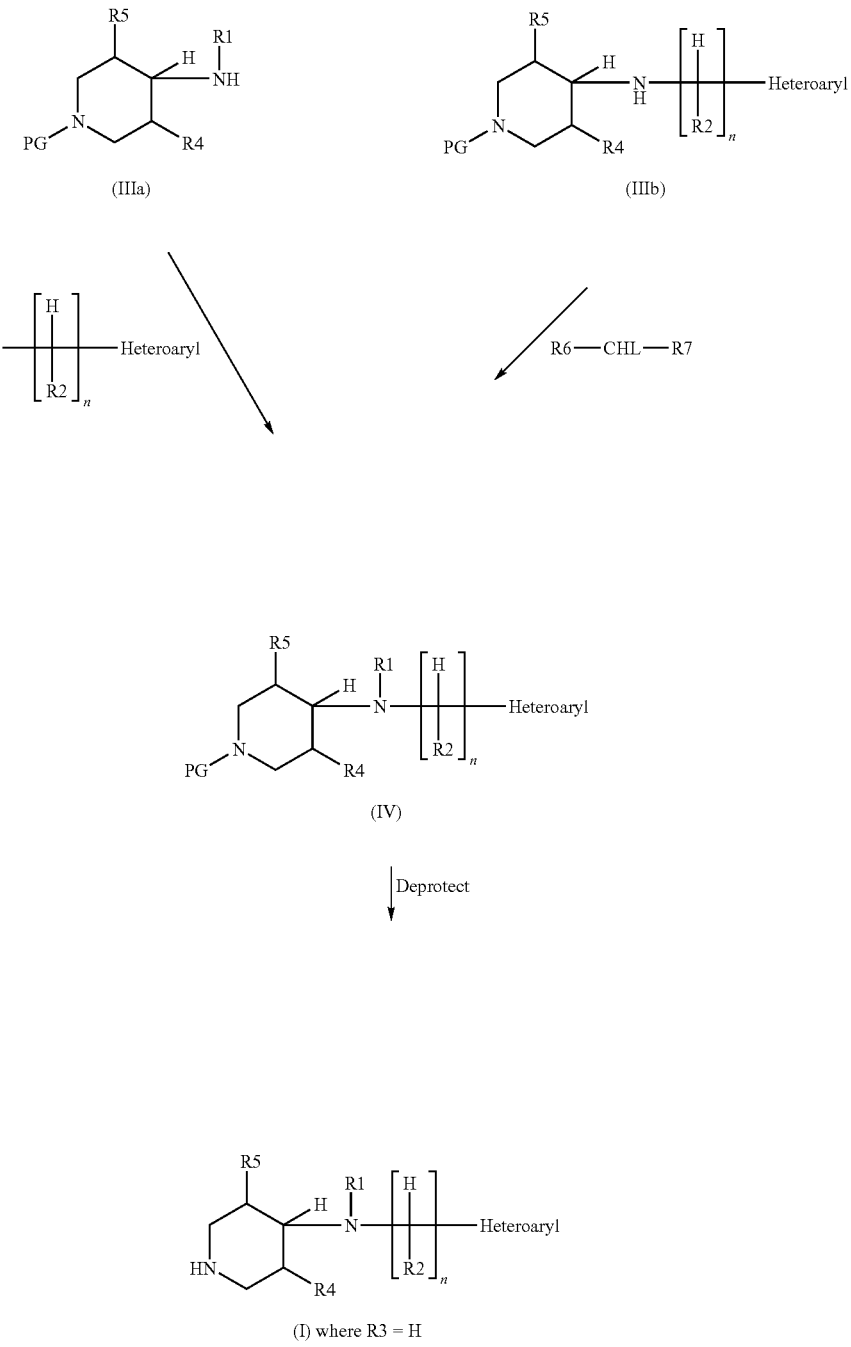

L represents a suitable leaving group—for example Cl, Br or tosyl.

The alkylation reaction preferably takes place in the presence of a base (e.g. potassium carbonate). Suitable solvents for the reaction include acetonitrile and DMF.

Suitable heteroaryl alkyl chlorides or bromides for reaction with the intermediate (IIIa) may be commercially available or, alternatively, may be prepared from other commercially available reagents using standard functional group conversions. For example, irradiation of a mixture of a Heteroaryl-alkyl, N-bromosuccinimide and 2,2'-azobisisobutyrnitrile in carbon tetrachloride provides a Heteroaryl-alkylbromide. Alternatively, addition of carbon tetrachloride to a solution of heteroaryl-alkanol and triphenylphosphine in a suitable solvent (e.g. anhydrous toluene) followed by heating provides a Heteroaryl-alkylchloride.

An alkylation reaction may also be used to obtain compounds of formula (I) having a beta-hydroxy motif within R1 as shown in Scheme 3.

Scheme 3

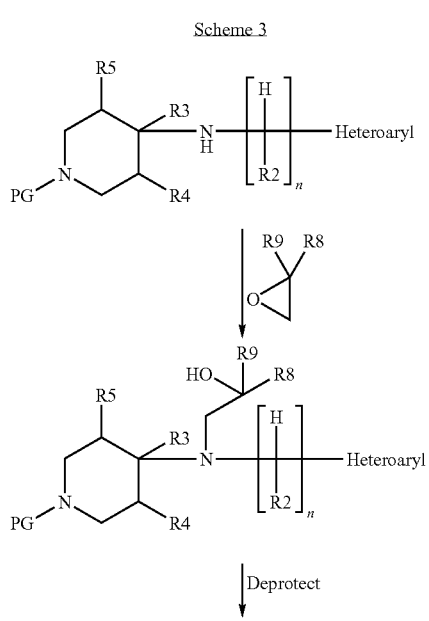

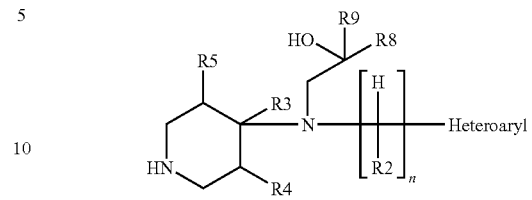

R8 and R9 being chosen in keeping with the definition of R1 above.

As another alternative to the second reductive amination step, compound (IIIa) may be reacted with an activated Heteroaryl-carboxylic acid (e.g. Heteroaryl-COCl) to provide an amide (V) which may be deprotected to give (VI) and subsequently reacted with a reducing agent (e.g. $BH_3 \cdot Me_2S$ or bis-(2-methoxyethoxy)aluminum hydride) in a suitable solvent (e.g. THF or toluene) to provide a compound of formula (I) as shown below in Scheme 4.

Scheme 4

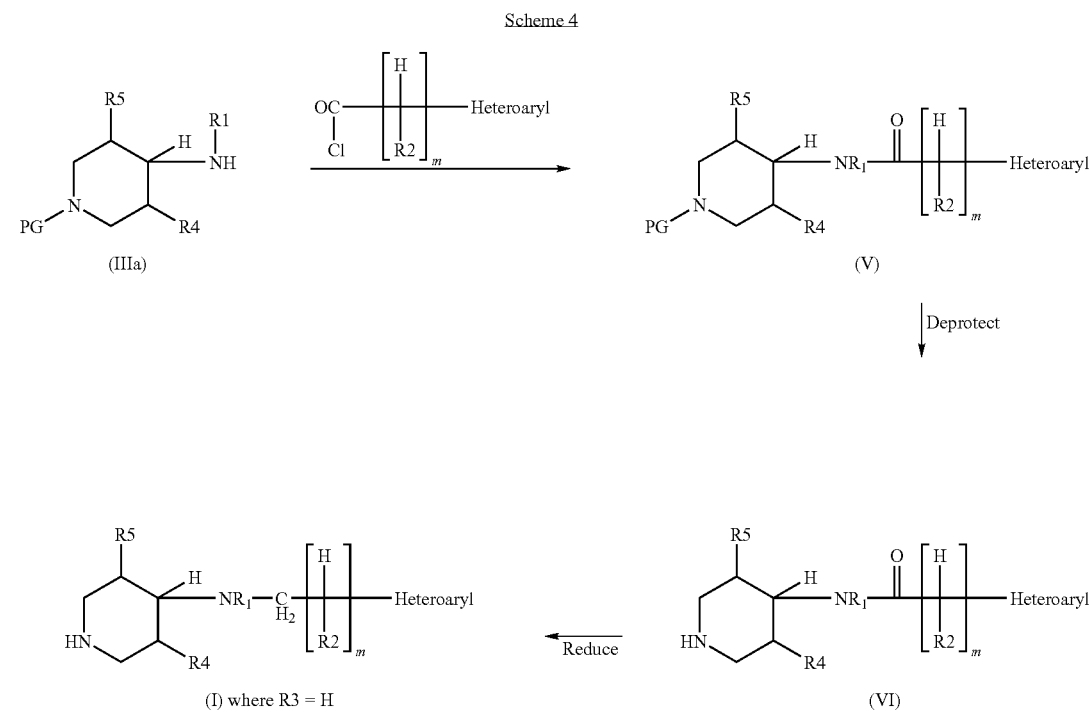

$m$ = 0, 1 or 2.

When R3 is $C_1$-$C_4$alkyl, a conventional synthetic route is outlined in the scheme shown below.

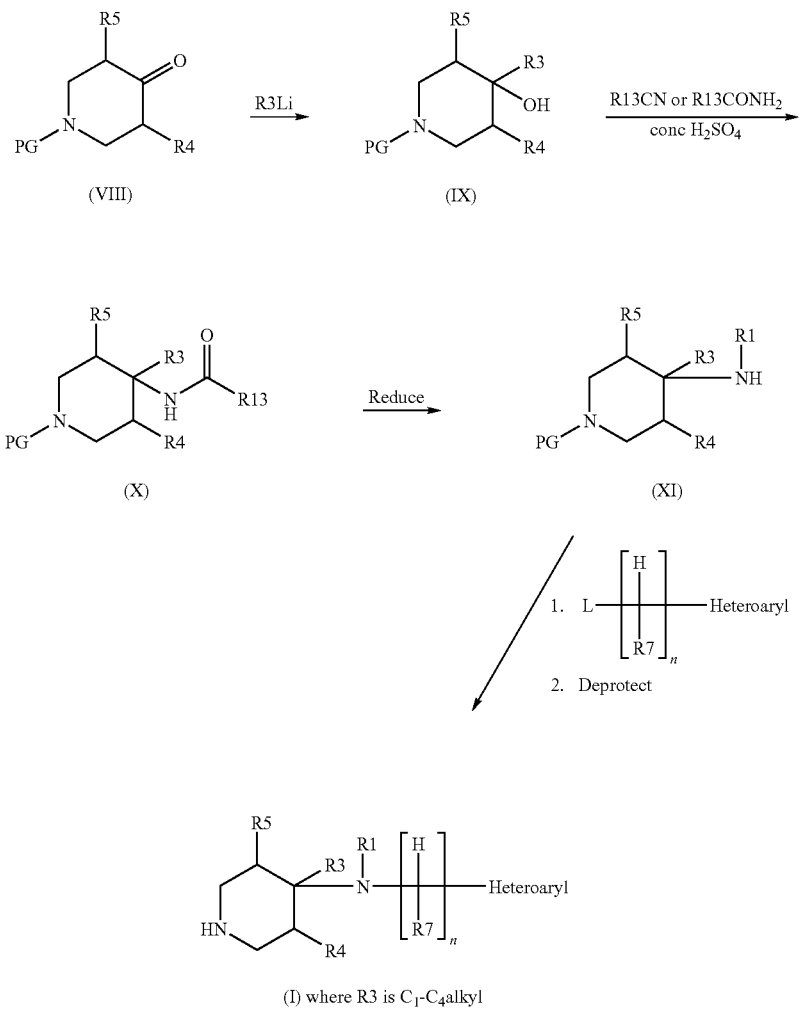

(I) where R3 is $C_1$-$C_4$alkyl

A N-protected 4-piperidone (VIII) is alkylated with an alkyllithium reagent to provide a 4-amino-piperidinol (IX). Treatment with an alkylnitrile or alkylamide under strongly acidic conditions provides a secondary amide (X) which may be reduced to provide a secondary amine (XI). Alkylation of the secondary amine (XI) followed by removal of the protecting group provides a compound of formula I (where R3 is $C_1$-$C_4$alkyl). In the scheme above L is a leaving group as previously defined and R13 is chosen such that R13-$CH_2$=R1.

If necessary, modifications to the substitutents on the Heteroaryl moiety may be carried out by standard functional group interconversions which will be well known to those of skill in the art. For example, a chloro substituent may be converted to a hydrogen or methyl substitutent by addition of an alkyllithium reagent (e.g. butyllithium or methyllithium) followed by quenching with water or methyl iodide respectively.

The present invention also provides a process for producing a compound of formula (I) above, or a pharmaceutically acceptable salt thereof, which comprises deprotection of a compound of the formula

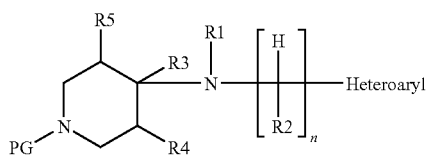

where PG is a N-protecting group and n, R1, R2, R3, R4, R5 and Heteroaryl are as defined for formula (I), optionally followed by formation of a pharmaceutically acceptable salt. Suitable N-protecting groups will be known to the person skilled in the art and include, for example, BOC, benzyl, benzyloxycarbonyl (CBZ) and acetyl.

EXAMPLE 1

N-(2-Methylpropyl)-N-{[3-methylthien-2-yl]methyl}piperidin-4-amine fumarate

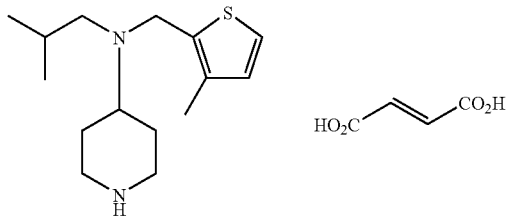

(i) To 10% Pd/C (3.0 g, 10% wt), under nitrogen, is added a solution of the 1-Boc-4-piperidone (30 g, 150.6 mmol, 1.0 eq.) and isobutylamine (11.2 g, 180.3 mmol, 1.2 eq) in ethanol (300 ml). This is hydrogenated for 1.5 h at 65 psi using a Parr hydrogenator. The catalyst is removed by filtration through Celite. Solvent is removed under vacuum to give 4-isobutylamino-piperidine-1-carboxylic acid tert-butyl ester as a colourless oil (31.2 g) with >98% purity. Mass spectrum (LCMS) Rt=2.79 (6 min gradient) ($M^+$+1) 257.2; $^1$H NMR (CDCl$_3$): δ=4.01 (2H, brs), 2.82-2.75 (2H, m), 2.61-2.54 (1H, m), 2.43 (2H, d), 1.85-1.81 (2H, m), 1.76-1.67 (1H, m), 1.56 (1H, br s), 1.45 (9H, s), 1.31-1.18 (2H, m), 0.91 (6H, d).

(ii) General method: To a solution of secondary amine (0.5 g, 1.0 eq) from (i) above in 1,2-dichloroethane (10 ml) is added the desired heterocyclic carboxaldehyde (1.5 eq.). To this is added a solution of sodium triacetoxyborohydride (1.5 eq.) in dimethylformamide (2 ml). This mixture is left to stir under nitrogen, at room temperature, for 3 days. Water (10 ml) is then added to the reaction mixture and the solution stirred vigorously for several minutes. The chlorinated organic layer is then run through a hydrophobic frit to remove water. The resulting organic solution is diluted with methanol (10 ml) and loaded onto an SCX-2 (10 g) column. The column is washed with methanol (50 ml) then basic material eluted with 2M ammonia in methanol. The ammonia/methanol solution is concentrated in vacuo to give the N-(2-methylpropyl)-N-butoxycarbonylpiperidin-4-amine intermediate.

(iii) General method: To a solution of the product from (ii) (1.0 eq) in dichloromethane (10 ml) is added trifluoroacetic acid (15 eq). The solution is stirred at room temperature for 4 h. The solvent and TFA are removed in vacuo. The resulting oil is taken up in methanol and loaded onto a prewashed SCX-2 (10 g) column. The column is washed with methanol (50 ml). Basic material is then eluted using 2M ammonia in methanol (50 ml). Removal of solvent from the ammonia/methanol mixture under vacuum, gives the desired compound as an oil. The oil is taken up in diethyl ether and a solution of fumaric acid (1 eq) in hot methanol is added. The mixture crystallises at room temperature or if necessary the solution is placed in the fridge for a few hours. The resulting precipitate is collected by filtration Specific Method: Following the general procedure above gives the title product as a white solid (0.44 g, 76%) with >98% purity: mass spectrum (LCMS): m/z=267.2 ($M^+$+1), Rt=2.58 (12 min gradient); $^1$H NMR (d6-DMSO): δ=7.25 (1H, d), 6.76 (1H, d), 6.42 (2H, s), 3.65 (2H, s), 3.25 (2H, brd), 2.78-2.60 (4H, m), 2.25-2.15 (2H, brd), 2.14-2.08 (3H, s), 1.81-1.55 (5H, m), 0.81 (6H, d).

EXAMPLE 2

N-(2-Methylpropyl)-N-{[3-methyl-1-benzothien-2-yl]methyl}piperidin-4-amine fumarate

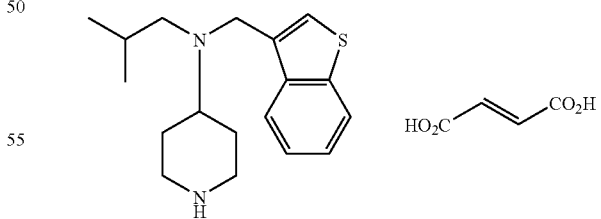

The title compound is prepared by the methods in example 1(ii) and 1(iii) using 3-methylbenzo[b]thiophene-2-carboxaldehyde: mass spectrum (LCMS): m/z=317.2 ($M^+$+1), Rt=5.26 (12 min gradient); $^1$H NMR (d6-DMSO): δ=7.85 (1H, d), 7.65 (1H, d), 7.37-7.25 (2H, m), 6.42 (2H, s), 3.86 (2H, s), 3.24 (2H, brd), 2.75-2.68 (3H, m), 2.30 (3H, s), 2.25 (2H, d), 1.84-1.66 (5H, m), 0.88 (6H, d).

EXAMPLE 3

N-(2-Methylpropyl)-N-{[1-benzothien-3-yl]methyl}piperidin-4-amine fumarate

The title compound is prepared by the methods in example 1(ii) and 1(iii) using benzo[b]thiophene-3-carboxaldehyde: mass spectrum (LCMS): m/z=303.2 ($M^+$+1), Rt=3.56 (12 min gradient); $^1$H NMR (d6-DMSO): δ=7.97-7.90 (2H, m), 7.57 (1H, s), 7.38-7.35 (2H, m), 6.52 (4H, s), 3.84 (2H, s), 3.28 (2H, brd), 2.78-2.70 (3H, m), 2.23 (2H, d), 1.84-1.60 (5H, m), 0.75 (6H, d).

EXAMPLE 4

N-(2-Methylpropyl)-N-{[thien-2-yl]methyl}piperidin-4-amine fumarate

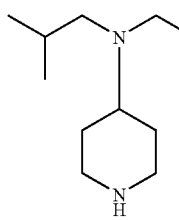 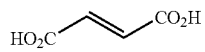

The general procedure in example 1(ii) for reductive amination is used with thiophene-2-carboxaldehyde. The deprotection procedure is as follows: The boc-amine (0.41 mg, 1.16 mmol) is dissolved in dichloromethane (10 ml), and trifluoroacetic acid (2 ml) and anisole (2 ml) are added in one portion, under an atmosphere of nitrogen. The reaction is monitored by thin layer chromatography (100% ethyl acetate; s.m. r.f. 0.4, prod r.f. 0.0). After 2 hours, the reaction is concentrated in vacuo, azeotroped with dichloromethane (c.a. 25 ml), taken up in methanol (c.a. 5 ml) and passed through an SCX-2 column. The resultant colourless oil is purified by chromatography. The resulting colourless oil is dissolved in aqueous acetonitrile (c.a. 20 ml), and fumaric acid (1 eq) added. After 5 minutes, this is freeze dried to give the title product as a white solid (0.27 g, 0.92 mmol): mass spectrum (LCMS): m/z=253.2 (M$^+$+1); Rt=1.37 (12 min gradient); $^1$H NMR (MeOD): $\delta_H$=7.25 (1H, d), 6.90 (2H, m), 6.65 (2H, s, fumarate), 3.86 (2H, s), 3.40 (2CH, m), 2.89 (3H, m), 2.30 (2H, d), 1.95 (2H, m), 1.73 (3H, m), 0.92 (6H, d).

EXAMPLE 5

N-(2-Methylpropyl)-N-{[thien-3-yl]methyl}piperidin-4-amine fumarate

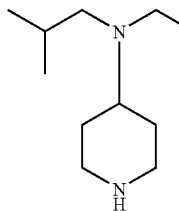 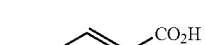

The compound is prepared similarly to the above example 4 using 4-isobutylamino-piperidine-1-carboxylic acid tert-butyl ester (0.40 g, 1.56 mmol) and thiophene-3-carboxaldehyde (0.52 g, 4.67 mmol) to give after deprotection the title product as a white solid (0.28 g, 0.93 mmol): mass spectrum (LCMS): m/z=253.2 (M$^+$+1); Rt=0.81 (12 min gradient); $^1$H NMR (MeOD): $\delta_H$ (300 MHz, CDCl$_3$) 7.32 (1H, m), 7.21 (1H, m), 7.06 (1H, m), 6.65 (2H, s, fumarate), 3.70 (2H, s), 3.49 (2H, m), 2.85 (3H, m), 2.30 (2H, d), 1.97 (2H, m), 1.73 (3H, m), 0.87 (6H, d).

EXAMPLE 6

N-(2-Methylpropyl)-N-{[furan-2-yl]methyl}piperidin-4-amine fumarate

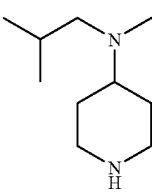 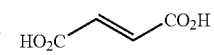

The compound is prepared similarly to the above example 4 using 4-isobutylamino-piperidine-1-carboxylic acid tert-butyl ester (0.40 g, 1.56 mmol) and furan-2-carboxaldehyde (0.52 g, 4.67 mmol) to give after deprotection the title product as a white solid (0.27 g, 0.92 mmol): mass spectrum (LCMS): m/z=237.2 (M$^+$+1); Rt=0.93 (12 min gradient); $^1$H NMR MeOD): $\delta$=7.32 (1H, m), 6.65 (2H, s, fumarate), 6.22 (1H, s), 6.13 (1H, s), 3.60 (2H, s), 3.32 (2H, m), 2.81 (2H, m), 2.70 (1H, m), 2.18 (2H, d), 1.85 (2H, m), 1.60 (3H, m), 0.73 (6H, d).

EXAMPLE 7

N-(2-Methylpropyl)-N-{[6-methylpyridin-2-yl]methyl}piperidin-4-amine fumarate

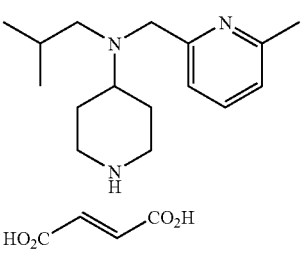 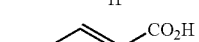

The title compound is prepared by the methods in example 1(ii) and 1(iii) using 6-methyl-2-pyridinecarboxaldehyde: mass spectrum (LCMS): m/z=262.2 (M$^+$+1), Rt=2.28 (12 min gradient); $^1$H NMR (d6-DMSO): $\delta$=7.70-7.60 (1H, m), 7.35-7.25 (1H, m), 7.12-7.05 (1H, m), 6.42 (2H, s), 3.68 (2H, s), 3.24 (2H, brd), 2.81-2.65 (3H, m), 2.41 (3H, s), 2.21 (2H, d), 1.89-1.51 (5H, m), 0.80 (6H, d).

EXAMPLE 8

N-(2-Methylpropyl)-N-[(benzothien-7-yl)methyl]piperidin-4-amine fumarate

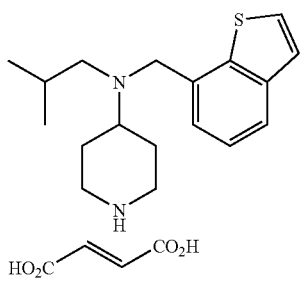

(i) To a solution of o-thiocresol (16.89 g, 136 mmol) in acetone (130 ml) is added potassium carbonate (20.5 g, 148 mmol) and a solution of bromoacetaldehyde dimethylacetal (19.93 g, 123 mmol) in acetone (20 ml) and the reaction mixture is stirred at ambient temperature overnight. The solids are filtered and washed with diethyl ether. The filtrate is concentrated and dissolved into ethyl acetate, washed successively with water, 0.5 N NaOH, and 2N NaOH. The combined aqueous fractions are extracted with dichloromethane. The combined organic fractions are dried over anhydrous $MgSO_4$, filtered and concentrated to afford 1-[(2,2-dimethoxyethyl)thio]-2-methyl-benzene as a brown oil (23.4 g, 90%) that is used without further purification. $^1$H NMR ($CDCl_3$): δ=7.33 (1H, brd), 7.19-7.08 (3H, m), 4.56 (1H, t), 3.38 (6H, s), 3.10 (2H, d), 2.42 (3H, s).

(ii) To a heated (130° C.) solution of polyphosphoric acid (59 g) in chlorobenzene (500 ml) is added a solution of 1-[(2,2-dimethoxyethyl)thio]-2-methyl-benzene (23.4 g, 110 mmol) in chlorobenzene (125 ml) slowly over several hours and when addition is complete the reaction mixture is heated for a further 8 hours. The reaction mixture is cooled to ambient temperature and stirred for an additional 24 hours. Water is added, the layers are separated, and the aqueous layer is extracted with dichloromethane. The combined organic extracts are dried over anhydrous $MgSO_4$, filtered, and concentrated. The crude material thus obtained is purified via flash chromatography on silica gel eluting with 100% pentane then 100% hexanes to afford 7-methyl-benzo[b]thiophene (12.65 g, 69%). $^1$H NMR ($CDCl_3$): δ=7.71 (1H, d), 7.45 (1H, d), 7.39 (1H, d), 7.33 (1H, dd), 7.17 (1H, d), 2.61 (3H, s).

(iii) A stirred, heated (110° C.) solution of 7-methyl-benzo[b]thiophene (4.98 g, 33.6 mmol), N-bromosuccinimide (4.97 g, 30.3 mmol), and 2,2'-azobisisobutyronitrile (0.500 g, 2.81 mmol) in carbon tetrachloride (150 ml) is irradiated with a sun lamp for 1 hour. The reaction is cooled to ambient temperature and methanol added until the solution is homogeneous. The solution is concentrated onto silica gel and purified via flash chromatography eluting with 100% hexanes to afford a solid (5.07 g) which is further purified by recrystallization from hexanes with cooling in the freezer to afford 7-bromomethyl-benzo[b]thiophene as a colourless solid (4.21 g, 61%). $^1$H NMR ($CDCl_3$): δ=7.81 (1H, dd), 7.50 (1H, d), 7.41-7.34 (3H, m), 4.79 (2H, s).

(iv) To a solution of 7-bromomethyl-benzo[b]thiophene (0.63 g, 2.8 mmol, 1 eq) and 1,1-dimethylethyl 4-[(2-methylpropyl)amino]piperidine-1-carboxylate (0.71 g, 2.8 mmol, 1 eq) in acetonitrile (25 ml) is added potassium carbonate (0.62 g, 4.4 mmol, 1.6 eq). The mixture is heated to reflux for 16 hours. The solution is filtered and the solvent removed in vacuo. The resulting oil is purified on a 40 g Redisep column using a gradient of 0-20% ethyl acetate/iso-hexane to give 1,1-dimethylethyl 4-{[(benzothien-7-yl)methyl]-(2-methylpropyl)amino}-piperidine-1-carboxylate as an oil (0.65 g, 40%); mass spectrum (LCMS): m/z=403.3 ($M^+$+1), Rt=4.40 (6 minute gradient); $^1$H NMR (300 MHz, $CDCl_3$): δ=7.79-7.65 (1 H, m), 7.46-7.40 (1 H, m), 7.37-7.30 (3 H, m), 4.18-4.06 (4H, m), 3.90 (2 H, s), 2.67-2.44 (3 H, m), 2.32-2.22 (2 H, m), 1.87-1.37 (8 H, m), 144 (4H, s) and 0.92-0.83 (6 H, m).

(v) To a solution of 1,1-dimethylethyl 4-{[(1-benzothien-7-yl)methyl]-(2-methylpropyl)amino}-piperidine-1-carboxylate (0.66 g, 1.6 mmol, 1 eq) in dichloromethane (10 ml) is added anisole (2 ml) and trifluoroacetic acid (2 ml). The solution is stirred at room temperature for 16 h. The solvent and trifluoroacetic acid are removed in vacuo. The resulting oil is taken up in methanol and loaded onto an SCX-2 (10 g) column. The column is washed with methanol (50 ml). Basic material is then eluted using 2M ammonia in methanol (50 ml). Removal of solvent from the ammonia/methanol mixture under vacuum, gave the desired compound (0.34 g, 75%) as an oil. This is taken up in diethyl ether (5 ml) and a solution of fumaric acid (0.13 g, 1 eq) in hot methanol (1 ml) is added. The mixture is left at room temperature for 1 hr. The resulting precipitate is collected by filtration to give a white solid, which is dried in a vacuum oven at 40° C. for 16 hours. This gives the title product as a white solid (0.24 g, 35%); mass spectrum (LCMS): m/z=303.1 ($M^+$30 1), Rt=4.72 (12 min gradient); $^1$H NMR (300 MHz, MeOD): δ=7.81-7.71 (1 H, m), 7.59-7.51 (1 H, m), 7.42-7.29 (3 H, m), 6.69 (2H, s), 3.97 (2 H, s), 3.46-3.38 (2 H, m), 2.96-2.75 (3 H, m), 2.35 (2 H, d), 2.18-2.01 (2 H, m), 1.95-1.65 (3 H, m) and 0.90 (6 H, d).

EXAMPLE 9

N-(2-Methylpropyl)-N-[(quinolin-3-yl)methyl]piperidin-4-amine fumarate

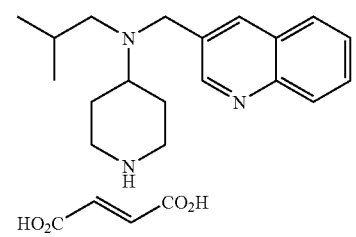

(i) Sodium triacetoxyborohydride (32.0 g, 151.0 mmol) is added to a stirred solution of tert-butyl 4-oxo-1-piperidine carboxylate (20.0 g, 100.4 mmol), isobutylamine (10.5 ml, 105.7 mmol), acetic acid (6.0 ml, 104.8 mmol) and 1,2-dichloroethane (300 ml). The reaction is stirred for 18 hours at room temperature under nitrogen. The reaction is poured into 2N NaOH (300 ml) and extracted with ethyl acetate (200 ml×3). The ethyl acetate is dried over sodium sulfate and then the sodium sulfate is filtered off. The crude product is concentrated on a rotary evaporator and purified by flash chromatography on silica gel eluting with 0.5% concentrated ammonium hydroxide/5% ethanol/chloroform to yield (24.5 g, 95%) of 4-isobutylamino-piperidine-1-carboxylic acid tert-butyl ester: mass spectrum (ion spray): m/z=257.1 (M+1); $^1$H NMR ($CDCl_3$): δ=4.01 (2H, br s), 2.78-2.75 (2H, m), 2.60-2.53 (1H, m), 2.42 (2H, d), 1.83-1.64 (3H, m), 1.56 (1H, br s), 1.44 (9H, s), 1.28-1.18 (2H, m), 0.90 (6H, d).

(ii) Sodium triacetoxyborohydride (1.29 g, 6.09 mmol) is added to a stirred solution of 4-isobutylamino-piperidine-1-carboxylic acid tert-butyl ester (1.09 g, 4.29 mmol), quinoline-3-carboxaldehyde (0.68 g, 4.3 mmol), acetic acid (0.25 ml, 4.37 mmol), and 1,2-dichloroethane (15 ml). The reaction is stirred for 18 h at room temperature under nitrogen. The reaction is poured into 2N NaOH (100 ml) and extracted with ethyl acetate (100 ml×3). The ethyl acetate is dried over sodium sulfate and then the sodium sulfate is filtered off. The crude product is concentrated on a rotary evaporator and purified by flash chromatography on silica gel eluting with 15% acetone/hexanes to yield (1.02 g, 60%) of 4-{isobutyl-[(quinolin-3-yl)methyl]-amino}-piperidine-1-carboxylic acid tert-butyl ester: mass spectrum (ion spray): m/z=398.2 (M+1); $^1$H NMR (CDCl$_3$): δ=8.93 (1H, d), 8.09 (1H, d), 8.02 (1H, s), 7.79 (1H, d), 7.70-7.66 (1H, m), 7.55-7.51 (1H, m), 4.16 (2H, br s), 3.79 (2H, s), 2.63-2.57 (3H, m), 2.27 (2H, d), 1.77-1.65 (3H, m), 1.52-1.48 (2H, m), 1.44 (9H, s), 0.85 (6H, d).

(iii) 4-{Isobutyl-[(quinolin-3-yl)methyl]-amino}-piperidine-1-carboxylic acid tert-butyl ester is added to a stirred solution of dichloromethane (5 ml) and anisole (9.0 ml, 82.8 mmol). The reaction is cooled to 0° C. Trifluoroacetic acid (6.0 ml, 72.9 mmol) is then added. The reaction is stirred for 1 h at 0° C. and then for 2 h at room temperature. The reaction is loaded onto a pre-washed SCX-2 (10 g) column and washed with methanol (200 ml). The product is then eluted with 2M ammonia in methanol (100 ml) and concentrated on a rotary evaporator to yield (0.74 g, 99%) of N-(2-methylpropyl)-N-[(quinolin-3-yl)methyl]piperidin-4-amine: mass spectrum (ion spray): m/z=298.2 (M+1); $^1$H NMR (CDCl$_3$): δ=8.93 (1H, d), 8.08 (1H, d), 8.02 (1H, d), 7.79-7.77 (1H, m), 7.68-7.64 (1H, m), 7.54-7.50 (1H, m), 3.79 (2H, s), 3.13-3.10 (2H, m), 2.59-2.46 (3H, m), 2.28 (2H, d), 2.06 (1H, br s), 1.80-1.77 (2H, m), 1.72-1.61 (1H, m), 1.55-1.44 (2H, m), 0.84 (6H, d).

(iv) N-(2-Methylpropyl)-N-[(quinolin-3-yl)methyl]piperidin-4-amine (0.74 g, 2.50 mmol) is dissolved in diethyl ether (35 ml) and methanol (6 ml). Fumaric acid (0.29 g, 2.50 mmol), in warm methanol (4 ml), is then added. Diethyl ether (100 ml) is added and the solution is heated. The solution is slowly cooled and then placed in the freezer. The solid is filtered and washed with diethyl ether to yield (0.79 g, 76%) of the title product: mass spectrum (ion spray): m/z=298.1 (M+1); $^1$H NMR (DMSO-d$_6$): δ=8.84 (d, 1H), 8.16 (d, 1H), 7.98-7.91 (m, 2H), 7.71-7.68 (m, 1H), 7.58-7.54 (m, 1H), 6.42 (s, 2H), 3.75 (s, 2H), 3.25-3.22 (m, 2H), 2.76-2.70 (m, 3H), 2.21 (d, 2H), 1.83-1.59 (m, 6H), 0.76 (d, 6H).

EXAMPLE 10

N-(2-Methylpropyl)-N-[(quinolin-4-yl)methyl]piperidin-4-amine fumarate

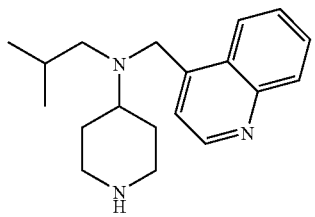

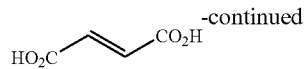
-continued

The title compound is prepared by the methods in example 9(ii), 9(iii), and 9(iv) using quinoline-4-carboxaldehyde: mass spectrum (ion spray): m/z=298.1 (M+1); $^1$H NMR (CD$_3$OD): δ=8.79 (1H, d), 8.31 (1H, d), 8.04 (1H, d), 7.79-7.74 (2H, m), 7.65-7.60 (1H, m), 6.70 (2H, s), 4.90 (3H, s), 4.23 (2H, s), 3.47-3.42 (2H, m), 2.95-2.82 (3H, m), 2.40 (2H, d), 2.11-2.08 (2H, m), 1.91-1.80 (2H, m), 1.69-1.59 (1H, m), 0.86 (6H, d).

EXAMPLE 11

N-(2-Methylpropyl)-N-[(1,3-benzothiazol-2-yl)methyl]piperidin-4-amine fumarate

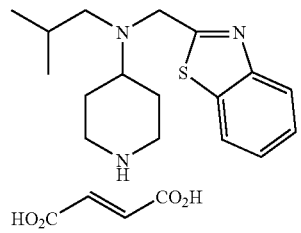

(i) Carbon tetrachloride (15.0 ml, 155 mmol) is added to a stirred solution of benzothiazolyl-2-methanol (2.50 g, 15.1 mmol), triphenylphosphine (4.89 g, 18.6 mmol), and anhydrous toluene (50 ml). The reaction is heated to reflux under nitrogen for 5 h. It is then concentrated on a rotary evaporator to give the crude product. The crude product is purified by flash chromatography on silica gel eluting with 100% dichloromethane to yield (2.36 g, 85%) of 2-chloromethyl-benzothiazole: mass spectrum (ion spray): m/z=183.9 (M+1); $^1$H NMR (CDCl$_3$): δ=8.04-8.01 (1H, m), 7.91-7.89 (1H, m), 7.53-7.49 (1H, m), 7.44-7.40 (1H, m), 4.95 (2H, s).

(ii) 4-{[(Benzothiazol-2-yl)methyl]-isobutyl-amino}-piperidine-1-carboxylic acid tert-butyl ester is made in 90% yield by the method of example 20(i), using 2-chloromethyl-benzothiazole: mass spectrum (ion spray): m/z=404.2 (M+1); $^1$H NMR (CDCl$_3$): δ=7.92 (1H, d), 7.85 (1H, d), 7.46-7.42 (1H, m), 7.36-7.32 (1H, m), 4.16 (2H, br s), 4.04 (2H, s), 2.69-2.57 (3H, m), 2.35 (2H, d), 1.82-1.68 (3H, m), 1.44 (11H, s), 0.96 (6H, d).

(iii) N-(2-Methylpropyl)-N-[(1,3-benzothiazol-2-yl)methyl]piperidin-4-amine is made in 99% yield by the method of example 9(iii), using 4-(benzothiazol-2-ylmethyl-isobutyl-amino)-piperidine-1-carboxylic acid tert-butyl ester: mass spectrum (ion spray): m/z=304.1 (M+1); $^1$H NMR (CDCl$_3$): δ=7.91 (1H, d), 7.84 (1H, d), 7.44-7.40 (1H, m), 7.34-7.31 (1H, m), 4.04 (2H, s), 3.12-3.09 (2H, m), 2.64-2.47 (3H, m), 2.37 (2H, d), 1.99-1.66 (4H, m), 1.50-1.40 (2H, m), 0.94 (6H, d).

(iv) The title product is made in 27% yield by the method of example 9(iv), using N-(2-methylpropyl)-N-[(1,3-benzothiazol-2-yl)methyl]piperidin-4-amine: mass spectrum (ion spray): m/z=304.1 (M+1); $^1$H NMR (CD$_3$OD): δ=7.94 (1H, d), 7.87 (1H, d), 7.50-7.46 (1H, m), 7.42-7.38 (1H, m), 6.70 (2H, s), 4.87 (3H, s), 4.11 (2H, s), 3.45-3.42 (2H, m), 2.98-2.87 (3H, m), 2.43 (2H, d), 2.10-2.07 (2H, m), 1.84-1.73 (3H, m), 0.98 (6H, d).

EXAMPLE 12

N-(2-Methylpropyl)-N-[(6-chloroimidazo[2,1-b][1,3]thiazol-5-yl)methyl]piperidin-4-amine fumarate

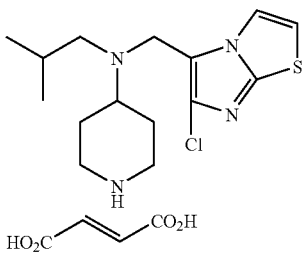

The title compound is prepared by the methods 9(ii), 9(iii), and 9(iv) using 6-chloroimidazo[2,1-b]thiazole-5-carboxaldehyde: mass spectrum (ion spray): m/z=327.1 (M+1); $^1$H NMR (CD$_3$OD): δ=7.67 (1H, d), 7.24 (1H, d), 6.68 (2H, s), 4.85 (3H, s), 3.89 (2H, s), 3.47-3.44 (2H, m), 2.99-2.91 (2H, m), 2.86-2.78 (1H, m), 2.26 (2H, d), 2.03-2.00 (2H, m), 1.85-1.75 (2H, m), 1.61-1.53 (1H, m), 0.77 (6H, d).

EXAMPLE 13

N-(2-Methylpropyl)-N-[(1-benzothien-5-yl)methyl]piperidin-4-amine fumarate

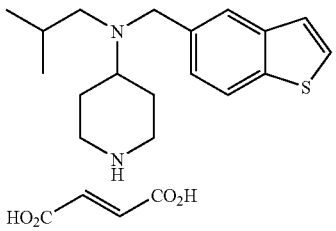

5-Methylbenzo(b)thiophene (0.37 g, 2.48 mmol) is dissolved in carbon tetrachloride (4 ml) and treated with N-bromosuccinimide (0.46 g, 2.58 mmol) and 2,2'-azobis-isobutyronitrile (10 mg). The mixture is stirred and warmed under reflux for 3 h and then left to cool to room temperature overnight. The mixture is filtered and the filtrate evaporated to dryness in vacuo at 40° C. The residual brown oil is treated with iso-hexane and warmed until it dissolves, before leaving to cool. The mixture is chilled and scratched until crystalline solid forms. The temperature is allowed to warm back up to room temperature and then the solid is isolated by filtration. The solid is then washed with more iso-hexane. The filtrate is concentrated to half the volume and then chilled again with scratching. Solid is re-formed and isolated by filtration, and air drying. The desired product is formed as a white solid, this material is used as 'seed' crystals.

The procedure is then repeated on a larger scale. Thus 5-methylbenzo(b)thiophene (51.3 g, 0.35 mol) is dissolved in carbon tetrachloride (540 ml), N-Bromosuccinimide (63.8 g, 0.36 mol, 1.04 eq), 2,2'-azobis-isobutyronitrile (0.4 g) are then added. The crude product is crystallised from iso-hexane (no heating) using 'seed' crystals. The material immediately formed and is isolated by filtration and dried. This material is dried further in vacuo at room temperature to give the desired product (69.62 g) which is recrystallised from hot iso-hexane and left to cool. The solid is isolated by filtration and dried in vacuo at room temperature to give the required product (59.6 g, 76%); $^1$H NMR (300 MHz, CDCl$_3$): δ=7.88-7.81 (2 H, m), 7.50-7.45 (1 H, m), 7.41-7.35 (1 H, m), 7.34-7.30 (1 H, m) and 4.65 (2 H, s).

(i) To a solution of 5-bromomethyl-benzo[b]thiophene (1.55 g, 6.8 mmol, 2.4 eq) and 1,1-dimethylethyl 4-[(2-methylpropyl)amino]piperidine-1-carboxylate (0.71 g, 2.8 mmol, 1 eq) in acetonitrile (25 ml) is added potassium carbonate (0.62 g, 4.4 mmol, 1.6 eq). The mixture is heated to reflux for 16 hours. The solution is filtered and the solvent removed in vacuo. The resulting oil is purified on a 40 g Redisep column using a gradient of 0-20% ethyl acetate/iso-hexane to give 1,1-dimethylethyl 4-{[(1-benzothienyl-5-yl)methyl]-(2-methylpropyl)amino}-piperidine-1-carboxylate as an oil (1.12 g, 100%). mass spectrum (LCMS): m/z=403.5 (M$^+$+1), Rt=3.38 (6 min gradient); $^1$H NMR (300 MHz, CDCl$_3$): δ=7.80-7.60 (2 H, m), 7.37-7.33 (1 H, m), 7.32-7.26 (1 H, m), 7.25-7.20 (1 H, m), 4.17-3.94 (2 H, m), 3.65 (2 H, s), 2.65-2.36 (3 H, m), 2.24-2.10 (2 H, d), 1.71-1.28 (5 H, m), 1.38 (9 H, s), 0.88-0.69 (6 H, d).

(ii) To a solution of 1,1-dimethylethyl 4-{[(1-benzothienyl-5-yl)methyl]-(2-methylpropyl)amino}-piperidine-1-carboxylate (1.12 g, 2.8 mmol, 1 eq) in dichloromethane (5 ml) is added trifluoroacetic acid (5.24 ml, 68 mmol, 24 eq). The solution is stirred at room temperature for 16 h. The solvent and trifluoroacetic acid are removed in vacuo. The resulting oil is taken up in methanol and loaded onto an SCX-2 (10 g and 5 g) column. The columns are washed with methanol (50 ml and 10 ml). Basic material is then eluted using 2M ammonia in methanol (50 ml and 10 ml). Removal of solvent from the ammonia/methanol mixture under vacuum, gives the desired compound (0.69 g, 82%) as an oil. This is further purified by mass guided preparative LCMS and loaded onto SCX-2 ion exchange cartridge (5 g). The column is washed with methanol (10 ml) and the product eluted with 2M ammonia in methanol solution (10 ml), the solvent is removed in vacuo to give a colourless oil (0.42 g, 1.4 mmol). This is taken up in diethyl ether (5 ml) and a solution of fumaric acid (0.16 g, 1 eq) in hot methanol (1 ml) is added. Solid precipitated on standing then the mixture is cooled to 0° C. for 1 hr. The precipitate is collected by filtration to give a white solid, which is dried, in a vacuum oven at 40° C. for 16 hours. This gives the title compound as a white solid (0.44 g, 38%), mass spectrum (LCMS): m/z=303.2 (M$^+$+1), Rt=3.19 (12 min gradient); $^1$H NMR (300 MHz, MeOD): δ=7.91-7.77 (2 H, m), 7.61-7.50 (1 H, m), 7.43-7.37 (1 H, m), 7.36-7.31 (1 H, m), 6.69 (2 H, s), 3.79 (2 H, s), 3.48-3.37 (2 H, m), 2.98-2.75 (3 H, m), 2.33 (2 H, d), 2.08-1.96 (2 H, m), 1.87-1.69 (3 H, m) and 0.91 (6 H, d).

EXAMPLE 14

N-(2-Methylpropyl)-N-[(1-benzothien-5-yl)methyl]piperidin-4-amine hemi-tartrate

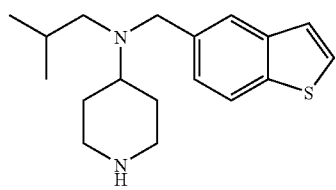

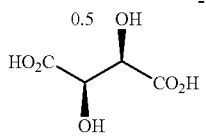
-continued (i) Add potassium carbonate (0.619 g, 4.4 mmol, 1.6 eq) followed by 5-bromomethyl-benzo[b]thiophene (17.7 g, 78 mmol, 1 eq) in one portion to a stirred solution of 1,1-dimethylethyl 4-[(2-methylpropyl)amino]piperidine-1-carboxylate (20 g, 78 mmol, 1 eq) in acetonitrile (400 ml). Cool, add water (250 ml) then filter. Wash the solid with ice cold acetonitrile and leave to dry on sinter for 1 hr. Purify on a 330 g Redisep column (20 g per column) using a gradient of 0-40% Ethyl acetate/iso-hexane to give 1,1-dimethylethyl 4-{[(1-benzothienyl-5-yl]methyl]-(2-methylpropyl)amino}-piperidine-1-carboxylate (7.64 g, 46%) as yellow solid. LCMS Rt=3.38 (6 min gradient) M$^+$+1: 403.5. 1H NMR (300 MHz, CDCl$_3$) δ ppm 7.80-7.60 (2 H, m), 7.37-7.33 (1 H, m), 7.32-7.26 (1 H, m), 7.25-7.20 (1 H, m), 4.17-3.94 (2 H, m), 3.65 (2 H, s), 2.65-2.36 (3 H, m), 2.24-2.10 (2 H, d), 1.71-1.28 (5 H, m), 1.38 (9 H, s), 0.88-0.69 (6 H, d).

(ii) Add trifluoroacetic acid (38.3 ml, 0.49 mol, 10 eq) to a solution of 1,1-dimethylethyl 4-{[(1-benzothienyl-5-yl)methyl]-(2-methylpropyl)amino}-piperidine-1-carboxylate (20 g, 49.4 mmol, 1 eq) in dichloromethane (80 ml). After 4 hours if not complete by tlc add an additional portion of trifluoroacetic acid (5 ml, 63 mmol, 1.3 eq). After 1 hr add water (200 ml) followed by iso-hexane (200 ml). Then take the acidic aqueous layer and basify with 2N NaOH (300 ml), extract with dichloromethane (2×200 ml). Combine the organic layers and dry over magnesium sulphate, filter and remove the solvent in vacuo. The resulting oil solidifies on standing then purify this solid by flash chromatography using a 120 g Redisep column and elute with 0-40% NH$_3$ methanol in dichloromethane. Dissolve the resulting product in methanol (60 ml) and add L-tartaric acid (1 eq). Heat the solution to dissolve, then cool and leave to stand in a fridge for 16 hrs. Filter and dry on a sinter for 1 hr to give the title product (3.04 g, 16%) as a white solid. LCMS Rt=3.19 (12 min gradient) M$^+$+1: 303.2. 1H NMR (300 MHz, MeOD) δ ppm 7.91-7.77 (2 H, m), 7.61-7.50 (1 H, m), 7.43-7.37 (1 H, m), 7.36-7.31 (1 H, m), 6.69 (2 H, s), 3.79 (2 H, s), 3.48-3.37 (2 H, m), 2.98-2.75 (3 H, m), 2.33 (2 H, d), 2.08-1.96 (2 H, m), 1.87-1.69(3 H, m) and 0.91 (6 H, d).

EXAMPLE 15

N-(2-Methylpropyl)-N-[(1-methyl-1H-indol-2-yl)methyl]piperidin-4-amine fumarate

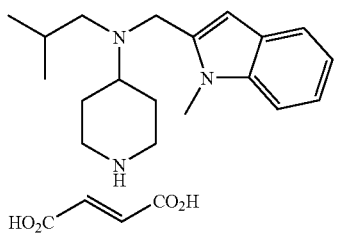

The title compound is prepared by the methods in example 9(ii), 9(iii), and 9(iv) using 1-methyl-1H-indole-2-carboxaldehyde: mass spectrum (ion spray): m/z=300 (M$^+$+1); $^1$H NMR (CD$_3$OD): δ=7.45 (1H, d), 7.30 (1H, d), 7.11 (1H, dd), 6.99 (1H, dd), 6.68 (2H, s), 6.37 (1H, s), 3.86 (2H, s), 3.81 (3H, s), 3.49 (2H, br d), 2.92-2.82 (3H, m), 2.31 (2H, d), 2.01 (2H, br d), 1.87-1.74 (2H, m), 1.69-1.59 (1H, m), 0.85 (6H, d).

EXAMPLE 16

N-(2-Methylpropyl)-N-[(isoquinolin-4-yl)methyl]piperidin-4-amine fumarate

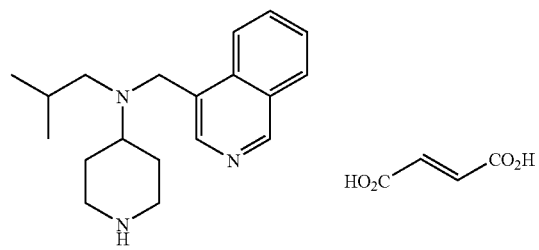

(i) n-Butyllithium (1.6 M in hexanes, 11.0 ml, 17.6 mmol) is added dropwise to a stirred solution of 4-bromoisoquinoline (3.02 g, 14.5 mmol) and anhydrous tetrahydrofuran (100 ml) at −78° C. under nitrogen. The reaction is stirred for 45 min at −78° C. and then dimethylformamide (6.0 ml, 77.5 mmol) is added. The reaction is then stirred for 3 h at −78° C. before it is quenched with water. The reaction is then poured into saturated sodium bicarbonate solution (200 ml) and extracted with ethyl acetate (100 ml×3). The ethyl acetate is washed with brine and dried over sodium sulfate. The sodium sulfate is filtered and the crude product is concentrated on a rotary evaporator. The crude product is purified by flash chromatography on silica gel eluting with 50% ethyl acetate/hexanes to yield (0.74 g, 33%) of isoquinoline-4-carboxaldehyde: mass spectrum (ion spray): m/z=158.1 (M+1).

(ii) 4-{Isobutyl-[(isoquinolin-4-yl)methyl]amino}-piperidine-1-carboxylic acid tert-butyl ester is prepared in 33% yield by the method of example 9(ii), using isoquinoline-4-carboxaldehyde: mass spectrum (ion spray): m/z=398.2 (M+1); $^1$H NMR (CDCl$_3$): δ=9.19 (1H, s), 8.52 (1H, s), 8.30 (1H, d), 8.01 (1H, d), 7.76-7.72 (1H, m), 7.65-7.62 (1H, m), 4.09 (2H, br s), 4.05 (2H, s), 2.62-2.55 (3H, m), 2.29 (2H, d), 1.80-1.77 (2H, m), 1.67-1.47 (3H, m), 1.45 (9H, s), 0.79 (6H, d).

(iii) N-(2-Methylpropyl)-N-[(isoquinolin-4-yl)methyl]piperidin-4-amine is made in 99% yield by the method of example 9(iii), using 4-{isobutyl-[(isoquinolin-4-yl)methyl]amino}-piperidine-1-carboxylic acid tert-butyl ester: mass spectrum (ion spray): m/z=298.2 (M+1); $^1$H NMR (CDCl$_3$): δ=9.16 (1H, s), 8.51 (1H, s), 8.30 (1H, d), 7.97 (1H, d), 7.71-7.67 (1H, m), 7.61-7.57 (1H, m), 4.04 (2H, s), 3.16-3.13 (2H, m), 2.62-2.47 (3H, m), 2.31 (2H, d), 2.09 (1H, br s), 1.84-1.81 (2H, m), 1.67-1.54 (3H, m), 0.77 (6H, d).

(iv) The title product is made in 49% yield by the method of example 9(iv), using N-(2-methylpropyl)-N-[(isoquinolin-4-yl)methyl]piperidin-4-amine: mass spectrum (ion spray): m/z=298.2 (M+1); $^1$H NMR (CD$_3$OD): δ=9.16 (1H, s), 8.46 (1H, s), 8.35 (1H, d), 8.12 (1H, d), 7.84-7.80 (1H, m), 7.72-7.68 (1H, m), 6.70 (2H, s), 4.85 (3H, s), 4.14 (2H, s), 3.46-

3.43 (2H, m), 2.95-2.84 (3H, m), 2.36 (2H, d), 2.10-2.06 (2H, m), 1.92-1.81 (2H, m), 1.66-1.59 (1H, m), 0.79 (6H, d).

EXAMPLE 17

N-(2-Methylpropyl)-N-[(quinolin-8-yl)methyl]piperidin-4-amine fumarate

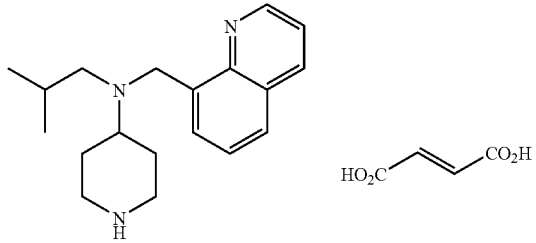

(i) sec-Butyllithium (1.4 M in cyclohexane, 5.0 ml, 7.0 mmol) is added dropwise to a stirred solution of 8-bromoquinoline (1.29 g, 6.22 mmol) and anhydrous tetrahydrofuran (22 ml) at −78° C. under nitrogen. The reaction is then stirred at −78° C. for 10 min and then dimethylformamide (2.5 ml, 32.3 mmol) is added. The reaction is then stirred for 10 min at −78° C. and then quenched with water. The reaction is poured into saturated sodium bicarbonate (100 ml) and extracted with ethyl acetate (100 ml×3). The ethyl acetate is dried over sodium sulfate and then the sodium sulfate is filtered. The crude product is concentrated on a rotary evaporator and purified by flash chromatography on silica gel eluting with 20% ethyl acetate/hexanes to yield (0.57 g, 58%) of quinoline-8-carboxaldehyde: mass spectrum (ion spray): m/z=158.0 (+1); $^1$H NMR (CDCl$_3$): δ=11.46 (1H, s), 9.06-9.04 (1H, m), 8.34-8.32 (1H, m), 8.26-8.23 (1H, m), 8.11-8.08 (1H, m), 7.70-7.66 (1H, m), 7.53-7.50 (1H, m).

(ii) 4-{Isobutyl-[(quinolin-8-yl)methyl]-amino}-piperidine-1-carboxylic acid tert-butyl ester is made in 65% yield by the method of example 9(ii), using quinoline-8-carboxaldehyde: mass spectrum (ion spray): m/z=398.2 (M+1); $^1$H NMR (CDCl$_3$): δ=8.91-8.89 (1H, m), 8.16-8.14 (1H, m), 8.05 (1H, d), 7.68 (1H, d), 7.57-7.53 (1H, m), 7.41-7.37 (1H, m), 4.40 (2H, s), 4.14 (2H, brs), 2.67-2.52 (3H, m), 2.39 (2H, d), 1.86-1.83 (2H, m), 1.72-1.46 (3H, m), 1.44 (9H, s), 0.89 (6H, d).

(iii) N-(2-Methylpropyl)-N-[(quinolin-8-yl)methyl]piperidin-4-amine is made in 99% yield by the method of 9(iii), using 4-{isobutyl-[(quinolin-8-yl)methyl]-amino}-piperidine-1-carboxylic acid tert-butyl ester: mass spectrum (ion spray): m/z=298.1 (M+1); $^1$H NMR (CDCl$_3$): δ=8.91-8.90 (1H, m), 8.16-8.14 (1H, m), 8.08-8.06 (1H, m), 7.68 (1H, d), 7.57-7.53 (1H, m), 7.40-7.37 (1H, m), 4.41 (2H, s), 3.12-3.09 (2H, m), 2.63-2.41 (5H, m), 1.90-1.87 (2H, m), 1.71-1.47 (4H, m), 0.89 (6H, d).

(iv) The title product is made in 86% yield by the method of example 9(iv), using N-(2-methylpropyl)-N-[(quinolin-8-yl)methyl]piperidin-4-amine: mass spectrum (ion spray): m/z=298.2 (M+1); $^1$H NMR (CD$_3$OD): δ=8.88-8.87 (1H, m), 8.36-8.34 (1H, m), 8.01-7.99 (1H, m), 7.87-7.85 (1H, m), 7.63-7.52 (2H, m), 6.66 (2H, s), 4.87 (3H, s), 4.49 (2H, s), 3.45-3.42 (2H, m), 3.08-3.01 (1H, m), 2.93-2.86 (2H, m), 2.56 (2H, d), 2.16-2.12 (2H, m), 1.96-1.78 (3H, m), 0.92 (6H, d).

EXAMPLE 18

N-(2-Methylpropyl)-N-[(1,3-thiazol-4-yl)methyl]piperidin-4-amine fumarate

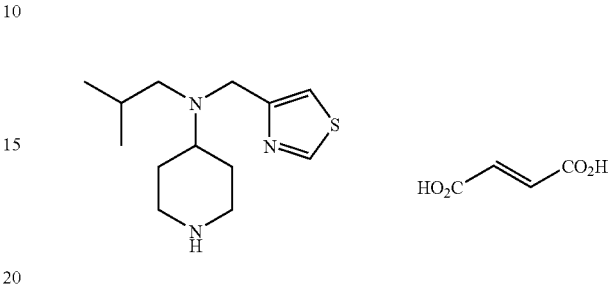

(i) To a solution of 4-isobutylamino-piperidine-1-carboxylic acid tert-butyl ester (537 mg, 2.1 mmol, 1 eq.) and 4-chloromethyl-thiazole (280 mg, 2.10 mmol, 1 eq.) in anhydrous dimethylformamide (6 mL) is added sodium iodide (66 mg, 0.44 mmol, 0.2 eq.) and potassium carbonate (354 mg, 2.5 mmol, 1.2 eq.), the reaction mixture is stirred at room temperature for 3 days, and then water and ethyl acetate are added. The layers are separated, and the aqueous layer is extracted with ethyl acetate. The combined organics are dried over anhydrous MgSO$_4$, filtered, and concentrated in vacuo. The crude material is purified using medium pressure liquid chromatography eluting from 0 to 25% THF in hexanes to afford 4-}isobutyl-[(thiazol-4-yl)methyl]-amino}-piperidine-1-carboxylic acid tert-butyl ester (559 mg, 75%). m/z=354 (M+1); $^1$H NMR (CDCl$_3$): δ=8.68 (1H, brs), 7.16 (1H, brs), 4.11 (2H, brs), 3.80 (2H, brs), 2.58 (3H, brs), 2.25-2.22 (2H, m), 1.71-1.57 (3H, m), 1.46-1.32 (11H, m), 0.82 (6H, d).

(ii) To a cooled (0° C.) solution of 4-{isobutyl-[(thiazol-4-yl)methyl]-amino}-piperidine-1-carboxylic acid tert-butyl ester (540 mg, 1.53 mmol, 1 eq.) in anhydrous dichloromethane (3 ml), is added anisole (2.5 g, 23 mmol, 15 eq.) and trifluoroacetic acid (2.6 g, 23 mmol, 15 eq.). The reaction is allowed to warm to room temperature and stirred for 4-5 hours. The reaction mixture is loaded on a SCX-2 column. The column is first washed with methanol and then the base eluted with 20% 2N NH$_3$ in methanol in dichloromethane. The solvents are removed in vacuo to afford isobutyl-(piperidin-4-yl)-[(thiazol-4-yl)methyl]-amine (387 mg). m/z=254 (M+1); $^1$H NMR (CDCl$_3$): δ=8.27 (1H, d), 7.22-7.21 (1H, m), 3.86 (2H, d), 3.15 (2H, brd), 2.62-2.49 (3H, m), 2.30 (2H, d), 2.03 (1H, brs), 1.78 (2H, d), 1.66-1.59 (1H, m), 1.50-1.40 (2H, m), 0.86 (6H, d).

(iii) Isobutyl-(piperidin-4-yl)-[(thiazol-4-yl)methyl]-amine (380 mg, 1.50 mmol, 1 eq.) is dissolved in a 1:1 mixture of diethyl ether and dichloromethane. Fumaric acid (191.5 mg, 1.65 mmol, 1.1 eq.) is dissolved in hot anhydrous methanol (1 ml) and then added to the solution of free base. Precipitation occurred upon cooling at 0° C. for 3 days. The precipitate is filtered, rinsed with ether, and dried in a vacuum oven (40° C.) overnight to give the title compound (416 mg, 75%). m/z=254 (M+1); $^1$H NMR (CD$_3$OD): δ=8.94 (1H, d), 7.44-7.43 (1H, m), 6.68 (2H, s), 3.88 (2H, s), 3.43 (2H, brd), 2.99-2.85 (3H, m) 2.33 (2H, d), 2.04 (2H, brd), 1.83-1.63 (3H, m), 0.87 (6H, d).

EXAMPLE 19

N-(2-Methylpropyl)-N-[(2,4-dichloro-1,3-thiazol-5-yl)methyl]piperidin-4-amine fumarate

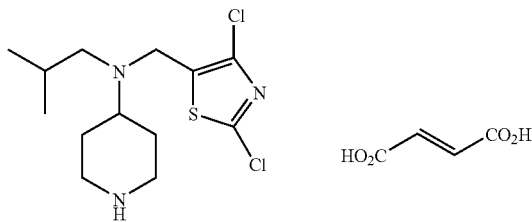
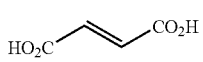

(i) To a solution of 4-(isobutylamino)-piperidine-1-carboxylic acid tert-butyl ester (797 mg, 2.28 mmol, 1 eq.) and 2,4-dichloro-5-thiazolecarboxaldehyde (500 mg, 2.75 mmol, 1.2 eq) in anhydrous dimethylformamide (10 ml), is added glacial acetic acid (130 uL, 2.28 mmol, 1 eq.) and NaBH(OAc)$_3$ (677 mg, 3.19 mmol, 1.4 eq.). The reaction mixture is stirred at room temperature for 3 days and then water and ethyl acetate are added. The layers are separated and the aqueous layer is extracted with ethyl acetate. The combined organics are washed with water, then dried over anhydrous Na$_2$SO$_4$, filtered, and concentrated in vacuo. The residue is purified on silica gel with 0 to 25% THF in hexanes to give 4-{[(2,4-dichloro-thiazol-5-yl)methyl]-isobutyl-amino}-piperidine-1-carboxylic acid t-butyl ester (303 mg, 31%): m/z=422 (M+1); $^1$H NMR (250 MHz, CDCl$_3$): δ=4.35 (2H, brd), 3.87 (2H, s), 2.80 (3H, m), 2.42 (2H,d), 1.86 (3H, m), 1.61 (11H, m), 1.06 (6H, d).

The title compound is prepared using the compound obtained in 19(i), and carrying out the reactions described 18(ii) and 18(iii): m/z=322 (M+1); $^1$H NMR (CD$_3$OD): δ=6.69 (2H, s), 3.81 (2H, s), 3.44 (2H, brd), 3.01-2.94 (2H, m), 2.89-2.82 (2H, m), 2.33 (2H, d), 2.00 (2H, brd), 1.79-1.68 (3H, m), 0.92 (6H, d).

EXAMPLE 20

N-(2-Methylpropyl)-N-[(2,1,3-benzothiadiazol-4-yl)methyl]piperidin-4-amine fumarate

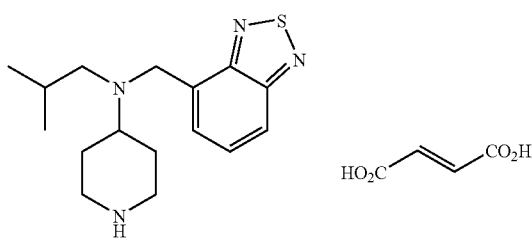
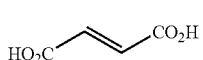

(i) 4-Bromomethyl-benzo[2,1,3]thiadiazole (0.94 g, 4.12 mmol) is added to a stirred solution of 4-isobutylamino-piperidine-1-carboxylic acid tert-butyl ester (1.01 g, 3.95 mmol), potassium carbonate (0.66 g, 4.76 mmol), sodium iodide (0.18 g, 1.21 mmol), and anhydrous dimethylformamide (15 ml). The reaction is heated to 85° C. under nitrogen for 3 h. The reaction is poured into saturated sodium bicarbonate (100 ml) and extracted with ethyl acetate (100 ml×3). The ethyl acetate is dried over sodium sulfate and then the sodium sulfate is filtered off. The crude product is concentrated on a rotary evaporator and purified by flash chromatography on silica gel eluting with 10% ethyl acetate/hexanes to yield (1.46 g, 91%) of 4-{[(benzo[2,1,3]thiadiazol-4-yl)methyl]-isobutyl-amino}-piperidine-1-carboxylic acid tert-butyl ester: mass spectrum (ion spray): m/z=405.2 (M+1): $^1$H NMR (CDCl$_3$): δ=7.86 (1H, d), 7.76-7.74 (1H, m), 7.60-7.56 (1H, m), 4.19 (2H, s), 4.12 (2H, br s), 2.68-2.54 (3H, m), 2.35 (2H, d), 1.83-1.79 (2H, m), 1.71-1.61 (1H, m), 1.54-1.46 (2H, m), 1.44 (9H, s), 0.87 (6H, d).

(ii) N-(2-Methylpropyl)-N-[(2,1,3-benzothiadiazol-4-yl)methyl]piperidin-4-amine is made in 91% yield by the method of example 9(iii), using 4-{[(benzo[2,1,3]thiadiazol-4-yl)methyl]-isobutyl-amino}-piperidine-1-carboxylic acid tert-butyl ester: mass spectrum (ion spray): m/z=305.1 (M+1); $^1$H NMR (CDCl$_3$): δ=7.86-7.84 (1H, m), 7.78-7.76 (1H, m), 7.60-7.56 (1H, m), 4.21 (2H, s), 3.13-3.10 (2H, m), 2.63-2.47 (3H, m), 2.38 (2H, d), 1.86-1.82 (2H, m), 1.70-1.45 (4H, m), 0.87 (6H, d).

(iii) The title product is made in 80% yield by the method of example 9(iv), using N-(2-methylpropyl)-N-[(2,1,3-benzothiadiazol-4-yl)methyl]piperidin-4-amine: mass spectrum (ion spray): m/z=305.1 (M+1); $^1$H NMR (CD$_3$OD): δ=7.89 (1H, d), 7.75-7.73 (1H, m), 7.66-7.63 (1H, m), 6.67 (2H, s), 4.85 (3H, s), 4.22 (2H, s), 3.46-3.42 (2H, m), 2.95-2.87 (3H, m), 2.40 (2H, d), 2.11-2.07 (2H, m), 1.89-1.65 (3H, m), 0.84 (6H, d).

EXAMPLE 21

N-(2-Methylpropyl)-N-[(quinolin-2-yl)methyl]piperidin-4-amine fumarate

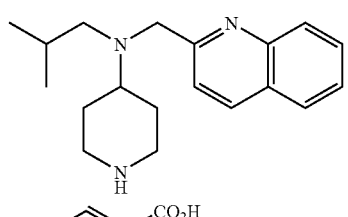
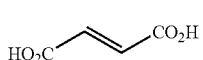

The title compound is prepared by the methods 19(i), 18(ii) and 18(iii), respectively, using quinoline-2-carboxaldehyde: m/z=298 (M+1); $^1$H NMR (CD$_3$OD): δ=8.31 (1H, d), 7.98 (1H, d), 7.91 (1H, d), 7.78-7.73 (2H, m), 7.60-7.56 (1H, m), 6.68 (2H, s), 3.97 (2H, s), 3.43 (2H, brd), 2.97-2.28 (3H, m), 2.40 (2H, d), 2.08 (2H, brd), 1.86-1.67 (3H, m), 0.89 (6H, d).

EXAMPLE 22

N-(2-Methylpropyl)-N-[(2,5-dichlorothien-3-yl)methyl]]piperidin-4-amine fumarate

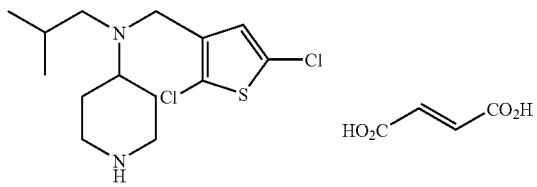

(i) To a cooled (0° C.) solution of 4-isobutylamino-piperidine-1-carboxylic acid tert-butyl ester (1.6 g, 6.1 mmol) in dry dichloromethane is added diisopropylethylamine (1.1 ml, 6.1 mmol) and 2,5-dichloro-thiophenecarbonyl chloride (1.1 g, 5.1 mmol). The reaction mixture is stirred for 3 hours at 0° C., then quenched with saturated aqueous NaHCO$_3$. The layers are separated and the aqueous layer is extracted with ethyl acetate. The combined organic extracts are washed with an aqueous saturated brine solution, dried over anhydrous Na$_2$SO$_4$, filtered, and concentrated in vacuo. The crude mixture is purified on silica gel 0-15% ethyl acetate/hexanes to give N-(2-methylpropyl)-N-[(2,5-dichlorothiophen-3-yl)-carbonyl]piperidin-1-carboxylic acid tert-butyl ester (1.73 g, 79%). The $^1$H NMR spectrum acquired in CDCl$_3$ showed evidence of rotamers. $^1$H NMR (CDCl$_3$): δ=6.75 (2H, s), 4.29-4.10 (5H, m), 3.63-3.57 (1H, m), 3.17 (2H, d), 3.08 (2H, d), 2.82-2.76 (2H, m), 2.59 (2H, brs), 2.16-2.13 (1H, m), 1.90-1.79 (3H, m), 1.69-1.62 (3H, m), 1.47-1.46 (18H, d), 1.32-1.25 (3H, m), 0.96 (6H, d), 0.79 (6H, d).

(ii) The material is deprotected to give N-(2-methylpropyl)-N-[(2,5-dichlorothiophen-3-yl)-carbonyl]piperidin-4-amine in a similar manner to 18(ii). m/z=335 (M+1).

(iii) To a solution of N-(2-methylpropyl)-N-[(2,5-dichlorothiophen-3-yl)-carbonyl]piperidin-4-amine (0.72 g, 2.14 mmol) in anhydrous tetrahydrofuran (5 ml) is added BF$_3$.Et$_2$O (0.73 g, 5.14 mmol) and the reaction mixture is heated to reflux. While refluxing, BH$_3$.Me$_2$S (1.6 ml, 3.2 mmol) is added and the reaction vented to remove Me$_2$S for 10 minutes. After an additional 2 hrs at reflux, TMEDA (0.75 g, 6.42 mmol) is added and the reaction mixture heated at reflux for 1 hr. The reaction mixture is cooled, and the precipitate is filtered and washed with dichloromethane. The filtrate is concentrated in vacuo. Aliquots of methanol (5 ml) are added to the residue and concentrated. This process is repeated until no more gas evolution is observed. The resulting residue is purified on silica gel (0-100%) 5% 2N NH$_3$ in methanol in dichloromethane to give N-(2-methylpropyl)-N-[(2,5-dichlorothien-3-yl)methyl]piperidin-4-amine (0.19 g, 28%). m/z=321 (M+1); 1H NMR (CD$_3$OD): δ=6.87 (1H, s), 3.65 (2H, s), 3.34-3.30 (2H, m), 2.86-2.78 (2H, m), 2.74-2.63 (1H, m), 2.26 (2H, d), 1.95-1.89 (2H, m), 1.72-1.58 (4H, m), 0.86 (6H, d).

(iv) The fumarate salt is formed following 18(iii): m/z=321 (M+1); $^1$H NMR (CD$_3$OD): δ=6.89 (1H, s), 6.68 (2H, s), 3.56 (2H, s), 3.43 (2H, brd), 3.00-2.92 (2H, m), 2.81-2.74 (1H, m), 2.26 (2H, d), 2.02 (2H, brd), 1.79-1.65 (3H, m), 0.88 (6H, d).

EXAMPLE 23

N-(2-Methylpropyl)-N-[(1,3-dimethyl-1H-pyrazol-5-yl)methyl]piperidin-4-amine fumarate

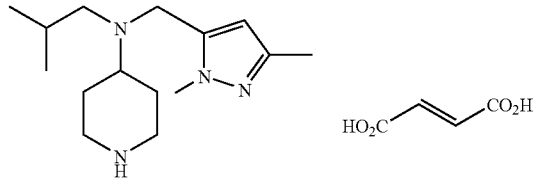

(i) Thionyl chloride (1.04 ml, 14.4 mmol) is added to a stirred solution of 1,3-dimethyl-1H-pyrazole-5-carboxylic acid (0.5 g, 3.6 mmol) and dimethylformamide (3 drops). The reaction is stirred for 2 hours at room temperature and then for 2 hours at 80° C. The reaction is concentrated. The residue is dissolved in dichloromethane and then the solvent is evaporated to yield 1,3-dimethyl-1H-pyrazole-5-carbonyl chloride.

(ii) Triethylamine (1.8 ml, 12.8 mmol) and 1,3-dimethyl-1H-pyrazole-5-carbonyl chloride (0.5 g, 3.2 mmol) is added to a stirred solution of 4-isobutylamino-piperidine-1-carboxylic acid tert-butyl ester (0.82 g, 3.2 mmol), and diethyl ether (30 ml). The reaction is stirred for 5 minutes at room temperature. The reaction is poured into 5% citric acid and extracted with ethyl acetate. The ethyl acetate is washed with sodium bicarbonate and brine and dried over sodium sulfate. The sodium sulfate is filtered off and the crude product is concentrated on a rotary evaporator to yield (1.15 g, 96% crude) of 4-{[(1,3-dimethyl-1H-pyrazol-5-yl)-carbonyl]-isobutyl-amino}-piperidine-1-carboxylic acid tert-butyl ester: mass spectrum (ion spray): m/z=379 (M$^+$+1); $^1$H NMR (CD$_3$OD) (broad peaks due to rotamers) δ=6.29-6.17 (1H, br m), 4.23-4.10 (2H, br m), 3.98-3.90 (1H, br m), 3.78 (3H, br s), 3.25 (2H, d), 2.89-2.57 (2H, br m), 2.25 (3H, s), 2.20-2.04 (1H, br m), 1.86-1.70 (3H, br m), 1.46 (9H, s), 1.00-0.74 (6H, br m).

(iii) 4-{[(1,3-dimethyl-1H-pyrazol-5-yl)-carbonyl]-isobutyl-amino}-piperidine-1-carboxylic acid tert-butyl ester (1.15 g, 3 mmol) is added to a stirred solution of dichloromethane (30 ml) and anisole (8.2 ml, 76 mmol). The reaction is cooled to 0° C. Trifluoroacetic acid (4.7 ml, 60 mmol) is then added and the reaction is stirred for 1 hour at 0° C. and then for 6 hours at room temperature. The reaction is loaded directly onto a 10 g prepacked SCX-2 cartridge and washed with methanol (200 ml). The product is then eluted off with 2M ammonia in methanol (100 ml) and concentrated on a rotary evaporator to yield (0.81 g, 96%) of [(1,3-dimethyl-1H-pyrazol-5-yl)-carbonyl]isobutyl-piperidin-4-amine: mass spectrum (ion spray): m/z=279 (M+1); $^1$H NMR (CD$_3$OD) has very broad peaks.

(iv) Red-Al, 65 wt % solution of bis (2-methoxyethoxy) aluminum hydride in toluene (4.4 ml, 13.4 mmol) is added to a stirred solution of (1,3-dimethyl-1H-pyrazole-5-carbonyl) isobutyl-piperidin-4-amine (0.8 g, 2.9 mmol) and toluene (38 ml) at 0° C. The reaction is stirred for 15 min at 0° C. and then 1 hour at room temperature. The reaction is cooled at 0° C. and then quenched with 5N sodium hydroxide (25 ml). The crude product is extracted with ethyl acetate. The ethyl acetate is washed with brine and dried over sodium sulfate. The product is purified by flash chromatography on silica gel eluted with 15% ethanol/1.5% ammonium hydroxide/chloroform: mass spectrum (ion spray): m/z=265 and 279 (M+1); $^1$H NMR (CD$_3$OD) shows (1,3-dimethyl-1H-pyrazole-5-carbonyl) isobutyl-piperidin-4-amine impurity present. Red-Al (1.6 ml, 4.9 mmol) is added to the product obtained following the procedure described above. The reaction is stirred for 3 hours at room temperature and then 1 hour at 80° C. The product is purified by flash chromatography on silica gel eluted with 18% ethanol/1.8% ammonium hydroxide/chloroform to yield (0.42 g, 55%) of N-(2-methylpropyl)-N-[(1,3-dimethyl-1H-pyrazol-5-yl)methyl]piperidin-4-amine: mass spectrum (ion spray): m/z=265 (M+1); $^1$H NMR (CD$_3$OD) δ=5.91 (1H, s), 3.78 (3H, s), 3.62 (2H, s), 3.07 (2H, br d), 2.61-2.45 (3H, m), 2.24 (2H, d), 2.17 (3H, s), 1.74 (2H, br d), 1.58-1.47 (3H, m), 0.81 (6H, d).

(v) The title product is made in 88% yield by the method of example 9(iv) using N-(2-methylpropyl)-N-[(1,3-dimethyl-1H-pyrazol-5-yl)methyl]piperidin-4-amine: mass spectrum (ion spray): m/z=265 (M$^+$+1); $^1$H NMR (CD$_3$OD): δ=6.79 (2H, s), 5.99 (1H, s), 3.79 (3H, s), 3.66 (2H, s), 3.45 (2H, br d), 2.99-2.90 (2H, m), 2.86-2.77 (1H, m), 2.26 (2H, d), 2.17 (3H, s), 1.99 (2H, br d), 1.85-1.71 (2H, m), 1.65-1.56 (1H, m), 0.84 (6H, d).

EXAMPLE 24

N-(2-Methylpropyl)-N-[(3-chloro-1-benzothien-2-yl)methyl]piperidin-4-amine fumarate

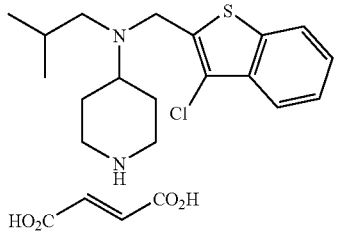

The title compound is prepared by the methods 19(i), 18(ii), and 18(iii), respectively, using 3-chloro-benzo[b]thiophene-2-carboxaldehyde: m/z=337 (M+); $^1$H NMR (CD$_3$OD): δ=7.82 (1H, d), 7.72 (1H, d), 7.45-7.36 (2H, m), 6.68 (2H, s), 4.04 (2H, s), 3.43 (2H, brd), 2.97-2.85 (3H, m), 2.38 (2H, d), 2.07 (2H, brd), 1.82-1.72 (3H, m), 0.97 (6H, d).

EXAMPLE 25

N-(2-Methylpropyl)-N-[(isoquinolin-1-yl)methyl]piperidin-4-amine fumarate

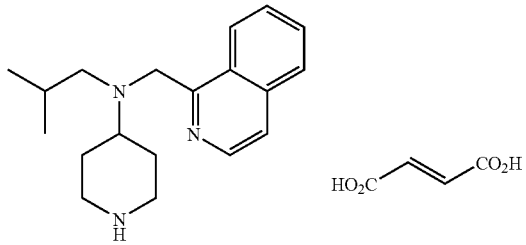

(i) Portions of 1,1'-carbonyldiimidazole (2.06 g, 12.7 mmol) are added to a stirred mixture of isoquinoline-1-carboxylic acid (2.00 g, 11.6 mmol) in dichloromethane (25 ml). N,O-dimethylhydroxylamine hydrochloride (1.24 g, 12.7 mmol) is added and the mixture is stirred at ambient temperature overnight. The reaction mixture is diluted with dichloromethane and then washed with saturated aqueous sodium bicarbonate followed by saturated aqueous sodium chloride. The organic solution is dried with sodium sulfate, filtered, and concentrated to give 2.5 g of N-methyl N-methoxy isoquinoline-1-carboxamide, which is used in the next step without further purification: mass spectrum (ion spray): m/z=217.0 (M+1).

(ii) A mixture of N-methyl N-methoxy isoquinoline-1-carboxamide (0.75 g, 3.47 mmol) in dry toluene (25 ml) is cooled to −37° C. and a solution of diisobutylaluminumhydride (DIBAL-H) in toluene (1M, 3.8 ml) is added. The reaction temperature is slowly increased to −4° C. over 4 h and a 20% aqueous solution of tartaric acid (10 ml) is added. The mixture is stirred for 10 min at ambient temperature, saturated aqueous sodium bicarbonate is added and the mixture extracted with dichloromethane. The combined organic layers are dried over sodium sulfate, filtered, and concentrated. The crude product and 4-(isobutylamino)-piperidine-1-carboxylic acid tert-butyl ester (0.89 g, 3.47 mmol), acetic acid (0.2 ml), and 1,2-dichloroethane (15 ml) are mixed and sodium triacetoxyborohydride (1.03 g, 4.86 mmol) is added. The reaction is stirred at ambient temperature over night. Aqueous sodium hydroxide (2M) is added and the mixture is extracted with diethyl ether. The combined organic layers are dried over sodium sulfate, filtered, and concentrated. The crude product is purified by column chromatography [silica, acetone/hexane (15:85)], followed by [silica, ethyl acetate/hexane (5:95), followed by ethyl acetate/hexane (1:3)] to give 0.23 g of 4-{(isobutyl)-[(isoquinolin-1-yl)-methyl]amino}-piperidine-1-carboxylic acid tert-butyl ester: mass spectrum (ion spray): m/z=398.1 (M+1). $^1$H NMR (CDCl$_3$): δ=8.60 (1H, d), 8.39 (1H, d), 7.79 (1H, d), 7.65 (1H, dd), 7.53-7.56 (2H, m), 4.10-4.30 (4H, m), 2.50-2.70 (3H, m), 2.25-2.35 (2H, m), 2.80-2.85 (2H, m), 1.45-1.60 (3H, m), 1.46 (9H, s), 0.68 (6H, d).

(iii) Using a method similar to example 9(iii), using 4-{(isobutyl)-[(isoquinolin-1-yl)-methyl]amino}-piperidine-1-carboxylic acid tert-butyl ester affords N-(2-methylpropyl)-N-[(isoquinolin-1-yl)methyl]piperidin-4-amine in 91% yield: mass spectrum (ion spray): m/z=298.2 (M+1); $^1$H NMR (CDCl$_3$): δ=8.66 (d, 1H), 8.40 (d, 1H), 7.79 (d, 1H), 7.67-7.63 (m, 1H), 7.57-7.52 (m, 2H), 4.25 (s, 2H), 3.15-3.12 (m, 2H), 2.62-2.49 (m, 3H), 2.31 (d, 2H), 1.88-1.40 (m, 6H), 0.64 (d, 6H).

(iv) Using a method similar to example 9(iv), with N-(2-methylpropyl)-N-[(isoquinolin-1-yl)methyl]piperidin-4-amine affords the title product in 54% yield: mass spectrum (ion spray): m/z=298.2 (M+1); $^1$H NMR (CD$_3$OD): δ=8.60-8.57 (m, 1H), 8.34 (d, 1H), 7.94 (d, 1H), 7.79-7.75 (m, 2H), 7.69-7.65 (m, 1H), 6.70 (s, 2H), 4.87 (s, 3H) 4,34 (s, 2H), 3.47-3.44 (m, 2H), 2.96-2.89 (m, 3H), 2.39 (d, 2H), 2.11-2.08 (m, 2H), 1.94-1.83 (m, 2H), 1.51-1.41 (m, 1H), 0.69 (d, 6H).

EXAMPLE 26

N-(2-Methylpropyl)-N-[(isoquinolin-3-yl)methyl]piperidin-4-amine fumarate

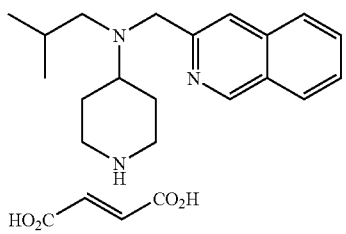

(i) To a cooled solution 0° C. of isoquinoline-3-carboxylic acid methyl ester (1.0 g, 5.34 mmol) in anhydrous tetrahydrofuran (100 ml), is added a solution of DIBAL-H (11.8 ml, 11.8 mmol). The reaction mixture is stirred at 0° C. for 2 hours and then quenched with saturated aqueous sodium potassium tartrate and stirred for 2 hours. The layers are separated and the aqueous layer is extracted with ethyl acetate. The combined organic extracts are washed with 1N HCl, 2N NaOH, and dried over anhydrous $Na_2SO_4$, filtered, and concentrated in vacuo. The crude reaction mixture is purified on silica gel eluting with 20% ethyl acetate/hexanes to give isoquinoline-3-carboxaldehyde (0.46 g, 54%). $^1$H NMR (CDCl$_3$): δ=10.24 (1H, brs), 9.32 (1H, brs), 8.35 (1H, brs), 8.02 (2H, brd), 7.77 (2H, brs).

(ii) The title compound is prepared by the methods 19(i), 18(ii), and 18(iii), respectively, using isoquinoline-3-carboxaldehyde: m/z=298 (M+1); $^1$H NMR (CD$_3$OD): δ=9.17 (1H, s), 8.08 (1H, d), 7.95 (1H, s), 7.89 (1H, s), 7.87-7.70 (1H, m), 7.68-7.59 (1H, m), 6.69 (2H, s), 3.98 (2H, s), 3.45 (2H, brd), 2.99-2.93 (3H, m), 2.41 (2H, d), 2.13 (2H, brd), 1.86-1.77 (2H, m), 1.72-1.66 (1H, m), 0.90 (6H, d).

EXAMPLE 27

N-(2-Methylpropyl)-N-[(1,3-dimethyl-1H-pyrazol-4-yl)methyl]piperidin-4-amine fumarate

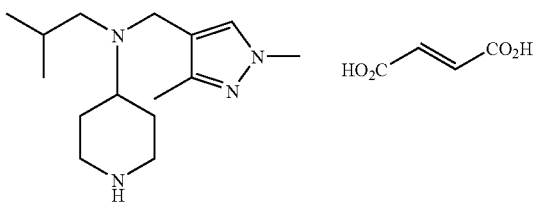

(i) To a cooled solution (0° C.) of 1,3-dimethyl-1H-pyrazole-4-carboxylic acid ethyl ester (5.0 g, 29.7 mmol) in anhydrous tetrahydrofuran (1000 ml), is added a solution of DIBAL-H (95.1 ml, 95.1 mmol). The reaction mixture is stirred at 0° C. for 2 hours and then quenched with saturated aqueous sodium potassium tartrate and stirred for 2 hours. The layers are separated and the aqueous layer is extracted with ethyl acetate. The combined organic extracts are dried over anhydrous $Na_2SO_4$, filtered, and concentrated in vacuo to give 1,3-dimethyl-1H-pyrazol-4-methanol (3.7 g, 100%) which is used without purification. $^1$H NMR (CDCl$_3$): δ=7.22 (1H, s), 4.46 (2H, s), 3.74 (3H, s), 2.20 (3H, s).

(ii) To a solution of 1,3-dimethyl-1H-pyrazol-4-methanol (0.33 g, 2.63 mmol), N-methyl morpholine N-oxide (0.37 g, 3.16 mmol), and crushed, dried, and activated 4 Å sieves (1.5 g) in anhydrous dichloromethane (20 ml), is added tetrapropyl ammonium peruthenate (0.09 g, 0.26 mmol). The reaction mixture is stirred for one hour at room temperature, then filtered through a silica gel plug and eluted with ethyl acetate. The filtrate is concentrated in vacuo to give 1,3-dimethyl-1H-pyrazole-4-carboxaldehyde (0.26 g, 81%) which is used without further purification. $^1$H NMR (CDCl$_3$): δ=9.83 (1H, s), 7.78 (1H, s), 3.86 (3H, s), 2.46 (3H, s).

(iii) N-(2-Methyl-propyl)-N-[(1,3-dimethyl-1H-pyrazol-4-yl)-methyl]-piperidin-4-amine fumarate is prepared by the methods 19(i), 18(ii), and 18(iii), respectively, using 1,3-dimethy-1H-pyrazole-4-carboxaldehyde: m/z=265 (M+1); $^1$H NMR (CD$_3$OD): δ=7.39 (1H, s), 6.69 (2H, s), 3.77 (3H, s), 3.51 (2H, s), 3.43 (2H, brd), 2.97-2.83 (3H, m), 2.25 (2H, d), 2.20 (3H, s), 1.96 (2H, brd), 1.82-1.68 (3H, m), 0.87 (6H, d).

EXAMPLE 28

N-(2-Methylpropyl)-N-[(1-methyl-3-(trifluoromethyl)-1H-pyrazol-4-yl)methyl]piperidin-4-amine fumarate

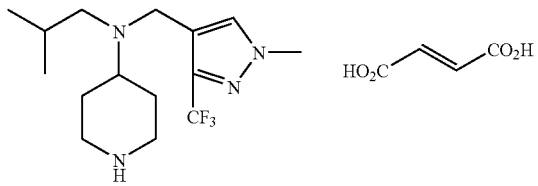

(i) To a cooled solution (0° C.) of 1-methyl-3-trifluoromethyl-1H-pyrazole-4-carboxylic acid ethyl ester (1.0 g, 4.5 mmol) in anhydrous tetrahydrofuran (50 ml), is added a solution of DIBAL-H (20.3 ml, 20.3 mmol). The reaction mixture is stirred at 0° C. for 2 hours and then quenched with saturated aqueous sodium potassium tartrate and stirred for 1 hr. The layers are separated and the aqueous layer is extracted 2 times with ethyl acetate. The combined organic extracts are dried over anhydrous $Na_2SO_4$, filtered, and concentrated in vacuo to give 1-methyl-3-trifluoromethyl-1H-pyrazol-4-methanol (1.0 g, 98%) which is used without purification. $^1$H NMR (CDCl$_3$): δ=7.43 (1H, s), 4.63 (2H, s), 3.90 (3H, s), 2.38 (1H, brs).

(ii) To a solution of 1-methyl-3-trifluoromethyl-1H-pyrazol-4-methanol (0.51 g, 2.83 mmol), N-methyl morpholine N-oxide (0.37 g, 3.16 mmol), and crushed, dried, and activated 4 Å sieves (1.5 g) in anhydrous dichloromethane (15 ml), is added tetrapropyl ammonium peruthenate (0.09 g, 0.26 mmol). The reaction mixture is stirred for one hour at room temperature, then filtered through a silica gel plug and eluted with ethyl acetate. The filtrate is concentrated in vacuo to give 1-methyl-3-trifluoromethyl-1H-pyrazole-4-carboxaldehyde (0.44 g, 88%), which is used without further purification. $^1$H NMR (CDCl$_3$): δ=9.92 (1H, s), 7.99 (1H, s), 4.00 (3H, s).

(iii) N-(2-Methylpropyl)-N-{[1-methyl-3-(trifluoromethyl)-1H-pyrazol-4-yl]-methyl}-piperidin-4-amine fumarate is prepared by the methods 19(i), 18(ii), and 18(iii), respectively, using 1-methyl-3-trifluoromethyl-1H-pyrazole-4-carboxaldehyde: m/z=319 (M+1); $^1$H NMR (CD$_3$OD): δ=7.66 (1H, s), 6.68 (2H, s), 3.91 (3H, s), 3.60 (2H, s), 3.43

(2H, brd), 2.97-2.89 (2H, m), 2.85-2.78 (1H, m), 2.25 (2H, d), 1.96 (2H, brd), 1.70-1.64 (3H, m), 0.87 (6H, d).

EXAMPLE 29

N-(2-Methylpropyl)-N-[(2-methylfuran-3-yl)methyl]piperidin-4-amine fumarate

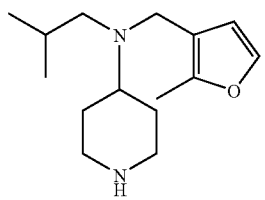 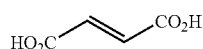

(i) To a cooled 0° C. solution of 2-methyl-furan-3-carboxylic acid methyl ester (1.0 g, 7.14 mmol) in anhydrous tetrahydrofuran (50 ml), is added a solution of DIBAL-H (5.6 ml, 8.6 mmol). The reaction mixture is stirred at 0° C. for 2.5 hours, quenched with 1N HCl and then is stirred for 20 minutes. The layers are separated and the aqueous layer is extracted with ethyl acetate. The combined organic extracts are dried over anhydrous $Na_2SO_4$, filtered, and concentrated in vacuo. The residue is diluted in 50 ml tetrahydrofuran, cooled to 0° C., and DIBAL-H added (22.8 ml, 22.8 mmol). The reaction mixture is stirred at 0° C. for 2.5 hours and then quenched with saturated aqueous sodium potassium tartrate and stirred until the appearance of two homogeneous layers. The layers are separated and the aqueous layer is extracted with ethyl acetate. The combined organic extracts are dried over anhydrous $Na_2SO_4$, filtered, and concentrated in vacuo to give 2-methyl-furan-3-methanol (0.81 g, >100%), which is used without purification. $^1$H NMR ($CDCl_3$): δ=7.26 (1H, s), 6.34 (1H, s), 4.45 (2H, s), 2.28 (3H, s), 1.85 (1H, brs).

(ii) To a solution 2-methyl-furan-3-methanol (0.47 g, 4.18 mmol), N-methyl morpholine N-oxide (0.58 g, 5.02 mmol), and crushed, dried, and activated 4 Å sieves (2.0 g) in anhydrous dichloromethane (15 ml) is added tetrapropyl ammonium peruthenate (0.14 g, 0.42 mmol). The reaction mixture is stirred for one hour at room temperature, then filtered through a silica gel plug and eluted with ethyl acetate. The filtrate is concentrated in vacuo to give 2-methyl-furan-3-carboxaldehyde (0.33 g, 72%) which is used without further purification. $^1$H NMR ($CDCl_3$): δ=9.88 (1H, s), 7.25 (1H, s), 6.63 (1H, s), 2.55 (3H, s).

(iii) N-(2-Methyl-propyl)-N-[(2-methylfuran-3-yl)-methyl]-piperidin-4-amine fumarate is prepared by the methods 19(i), 18(ii), and 18(iii), respectively, using 2-methyl-furan-3-carboxaldehyde: m/z=251 (M+1); $^1$H NMR ($CD_3OD$): δ=7.26 (1H, d), 6.68 (2H, s), 6.27 (1H, d), 3.44-3.40 (5H, m), 2.96-2.89 (2H, m), 2.85-2.77 (1H, m), 2.24-2.22 (5, m), 1.96 (2H, brd), 1.80-1.68 (3H, m), 0.88 (6H, d).

EXAMPLE 30

N-(2-Methylpropyl)-N-[(2,4-dimethyl-1,3-thiazol-5-yl)methyl]piperidin-4-amine tartrate

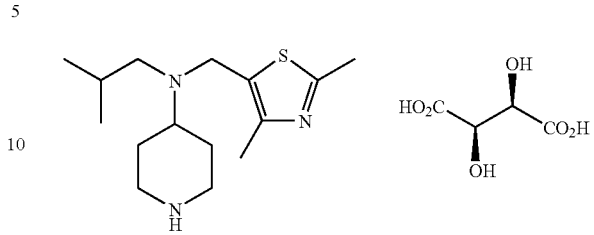

(i) Sodium triacetoxyborohydride (4.5 g, 21.23 mmol) is added to a stirred solution of 4-amino-piperidine-1-carboxylic acid tert-butyl ester (2.63 g, 13.13 mmol), 2,4-dimethyl-thiazole-5-carboxaldehyde (1.95 g, 13.81 mmol, Maybridge), acetic acid (0.80 ml, 13.98 mmol) and 1,2-dichloroethane (125 ml). The reaction is stirred overnight at room temperature under nitrogen. The reaction is poured into 2N NaOH (300 ml) and extracted with ethyl acetate (200 ml×3). The ethyl acetate is dried over sodium sulfate, filtered, and the filtrate concentrated. The crude product is purified by flash chromatography on silica gel eluting with 0.5% concentrated ammonium hydroxide/5% ethanol/chloroform to yield (2.93 g, 69%) of 4-{[(2,4-dimethyl-thiazol-5-yl)methyl]-amino}-piperidine-1-carboxylic acid tert-butyl ester: mass spectrum (ion spray): m/z=326.2 (M+1); $^1$H NMR ($CDCl_3$): δ=4.10 (2H, br m), 3.91 (2H, s), 2.88-2.79 (2H, brm), 2.73-2.66 (1H, m), 2.66 (3H, s), 2.34 (3H, s), 1.86 (2H, brd), 1.48 (9H, s), 1.36-1.24 (3H, m).

(ii) Sodium triacetoxyborohydride (1.13 g, 5.33 mmol) is added to a stirred solution of 4-{[(2,4-dimethyl-thiazol-5-yl)methyl]-amino}-piperidine-1-carboxylic acid tert-butyl ester (1.03 g, 3.18 mmol), isobutryaldehyde (0.32 ml, 3.52 mmol), acetic acid (0.20 ml, 3.49 mmol), and 1,2-dichloroethane (35 ml). The reaction is stirred for 25 h at room temperature under nitrogen. The reaction is poured into 2N NaOH (100 ml) and extracted with ethyl acetate (100 ml×3). The ethyl acetate is dried over sodium sulfate and then the sodium sulfate is filtered off. The crude product is concentrated on a rotary evaporator and purified by flash chromatography on silica gel eluting with 40% ethyl acetate/hexanes to yield (1.13 g, 93%) of 4-{[(2,4-dimethyl-thiazole-5-yl)methyl]-isobutyl-amino}-piperidine-1-carboxylic acid tert-butyl ester: mass spectrum (ion spray): m/z=382.3 (M+1); $^1$H NMR ($CDCl_3$): δ=4.19 (2H, brs), 3.66 (2H, s), 2.67-2.56 (6H, m), 2.32 (3H, s), 2.22 (2H, d), 1.74-1.64 (4H, m), 1.48 (9H, s), 1.45-1.37 (1H, m), 0.90 (6H, d).

(iii) 4-{(2,4-dimethyl-thiazole-5-yl)methyl]-isobutyl}-amino-piperidine-1-carboxylic acid tert-butyl ester (1.11 g, 2.92 mmol) is added to a stirred solution of dichloromethane (5 ml) and anisole (9.0 ml, 82.8 mmol). The reaction is cooled to 0° C. Trifluoroacetic acid (6.0 ml, 72.9 mmol) is then added. The reaction is stirred for 20 minutes at 0° C. and then for 3 h at room temperature. The reaction is loaded onto a pre-washed SCX-2 (10 g) column and washed with methanol (200 ml). The product is then eluted off with 2M ammonia in methanol (100 ml) and concentrated on a rotary evaporator to yield (0.70 g, 85%) of N-(2-methylpropyl)-N-[(2,4-dimethyl-1,3-thiazol-5-yl)methyl]piperidin-4-amine: mass spectrum (ion spray): m/z=282.2 (M+1); $^1$H NMR ($CDCl_3$): δ=3.67 (2H, s), 3.14 (2H, brd), 2.64 (3H, s), 2.56-2.50 (3H, m), 2.32 (3H, s), 2.25 (2H, d), 1.77-1.64 (4H, m), 1.50-1.38 (2H, m), 0.90 (6H, d).

(iv) N-(2-Methylpropyl)-N-[(2,4-dimethyl-1,3-thiazol-5-yl)methyl]piperidin-4-amine (0.70 g, 2.49 mmol) and L-tartaric acid (0.37 g, 2.49 mmol) are dissolved in methanol (25 ml). The solution is stirred for 1.5 h and concentrated. The solid is dried in a vacuum oven overnight to yield (1.05 g, 98%) N-(2-methylpropyl)-N-[(2,4-dimethyl-1,3-thiazol-5-yl)methyl]piperidin-4-amine tartrate: mass spectrum (ion spray): m/z=282.2 (M+1); $^1$H NMR (CD$_3$OD): δ=4.45 (2H, s), 3.77 (2H, s), 3.47 (2H, brd), 3.00-2.91 (2H, m), 2.88-2.79 (1H, m), 2.62 (3H, s), 2.34-2.30 (5H, m), 1.99 (2H, brd), 1.85-1.70 (3H, m), 0.93 (6H, d).

EXAMPLE 31

N-(2-Methylpropyl)-N-[(2-methoxy-4-chloro-1,3-thiazol-5-yl)methyl]piperidin-4-amine tartrate

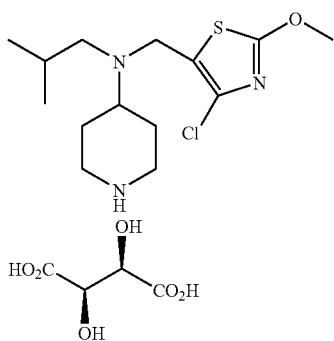

(i) Ethylene glycol (7.0 ml, 125.5 mmol) and p-toluenesulfonic acid monohydrate (0.56 g, 2.94 mmol) are added to a solution of 2,4-dichloro-thiazole-5-carboxaldehyde (7.88 g, 43.3 mmol) in toluene (100 ml). The reaction is heated at reflux and water removed via Dean-Stark for 4 h. The reaction is cooled, poured into 20% Na$_2$CO$_3$ (200 ml), and extracted with ethyl acetate (3×100 ml). The ethyl acetate is washed with aqueous saturated brine solution and dried over anhydrous Na$_2$SO$_4$. The solid is filtered off and the filtrate concentrated. The crude product is purified by flash chromatography on silica gel eluting with 10% ethyl acetate/hexanes to yield (9.42 g, 96%) of 2,4-dichloro-5-([1,3]dioxolan-2-yl)-thiazole: $^1$H NMR (CDCl$_3$): δ=6.07 (1H, s), 4.18-3.99 (4H, m).

(ii) Sodium methoxide (0.63 g, 11.66 mmol) is added to a solution of 2,4-dichloro-5-([1,3]dioxolan-2-yl)-thiazole (2.00 g, 8.85 mmol) in methanol (20 ml). The reaction is heated at reflux for 3.5 h, cooled, and concentrated. The residue is partitioned between aqueous saturated brine solution and ethyl acetate, separated, and the aqueous layer extracted with ethyl acetate. The ethyl acetate is dried over Na$_2$SO$_4$, filtered, and concentrated. The crude product is purified by flash chromatography on silica gel eluting with 12.5% ethyl acetate/hexanes to yield (1.12 g, 93%) of 4-chloro-5-([1,3]dioxolan-2-yl)-2-methoxy-thiazole: mass spectrum (ion spray): m/z=221.9 (M+1); $^1$H NMR (CDCl$_3$): δ=6.05 (1H, s), 4.15-3.97 (7H, m).

(iii) 5N HCl (10 ml) is added to a solution of 4-chloro-5-([1,3]dioxolan-2-yl)-2-methoxy-thiazole (1.80 g, 8.13 mmol) in tetrahydrofuran (50 ml). After 1 h, the reaction is poured into 2N NaOH (100 ml) and extracted with ethyl acetate (3×100 ml). The ethyl acetate is washed with aqueous saturated brine solution, dried with anhydrous Na$_2$SO$_4$, filtered, and concentrated. The crude product is purified by flash chromatography on silica gel eluting with 20% ethyl acetate/hexanes to yield (1.30 g, 90%) of 4-chloro-2-methoxy-thiazole-5-carboxaldehyde: mass spectrum (ion spray): m/z=178.0 (M+1); $^1$H NMR (CDCl$_3$): δ=9.95 (1H, s), 4.22 (3H, s).

(iv) 4-{[(4-chloro-2-methoxy-thiazol-5-yl)methyl]-amino}-piperidine-1-carboxylic acid tert-butyl ester is made in 70% yield by the method of example 30(i), using 4-chloro-2-methoxy-thiazole-5-carboxaldehyde: mass spectrum (ion spray): m/z=362.2 (M+1); $^1$H NMR (CDCl$_3$): δ=4.10-4.00 (5H, m), 3.89 (2H, s), 2.88-2.79 (2H, m), 2.73-2.64 (1H, m), 1.88 (2H, brd), 1.48 (9H, s), 1.33-1.23 (3H, m).

(v) 4-{[(4-Chloro-2-methoxy-thiazol-5-yl)methyl]-isobutyl-amino}-piperidine-1-carboxylic acid tert-butyl ester is made in 91% yield by the method of example 30(ii), using 4-{[(4-chloro-2-methoxy-thiazol-5-yl)methyl]-amino}-piperidine-1-carboxylic acid tert-butyl ester: mass spectrum (ion spray): m/z=418.3 (M+1); $^1$H NMR (CDCl$_3$): δ=4.20 (2H, brs), 4.11 (3H, s), 3.64 (2H, s), 2.70-2.57 (3H, m), 2.24 (2H, d), 1.73-1.64 (4H, m), 1.49 (9H, s), 1.43-1.38 (1H, m), 0.90 (6H, d).

(vi) N-(2-Methylpropyl)-N-[(2-methoxy-4-chloro-1,3-thiazol-5-yl)methyl]piperidin-4-amine is made in 97% yield by the method of example 30(iii), using 4-{[(4-chloro-2-methoxy-thiazol-5-yl)methyl]-isobuytyl}-amino-piperidine-1-carboxylic acid tert-butyl ester: mass spectrum (ion spray): m/z=318.2 (M+1); $^1$H NMR (CDCl$_3$): δ=4.07 (3H, s), 3.66 (2H, s), 3.18-3.11 (2H, m), 2.61-2.52 (3H, m), 2.27 (2H, d), 1.78-1.59 (4H, m), 1.47-1.36 (2H, m), 0.90 (6H, d).

(vii) N-(2-Methylpropyl)-N-[(2-methoxy-4-chloro-1,3-thiazol-5-yl)methyl]piperidin-4-amine tartrate is made in 98% yield by the method of example 30(iv), using N-(2-methylpropyl)-N-[(2-methoxy-4-chloro-1,3-thiazol-5-yl)methyl]piperidin-4-amine: mass spectrum (ion spray): m/z=318.2 (M+1); $^1$H NMR (CD$_3$OD): δ=4.44 (2H, s), 4.06 (3H, s), 3.75 (2H, s), 3.48 (2H, brd), 3.03-2.94 (2H, m), 2.91-2.82 (1H, m), 2.33 (2H, d), 2.00 (2H, brd), 1.84-1.71 (3H, m), 0.94 (6H, d).

EXAMPLE 32

N-(2-Methylpropyl)-N-[(2-methyl-4-chloro-1,3-thiazol-5-yl)methyl]piperidin-4-amine tartrate

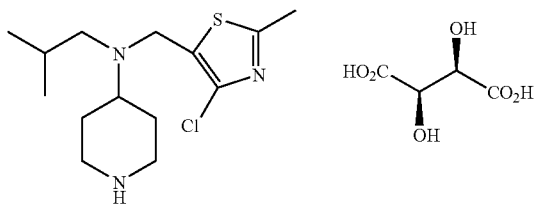

(i) Methyl lithium (10 ml, 16.0 mmol) is added to a cold (−78° C.) solution of 2,4-dichloro-5-[1,3]dioxolan-2-yl-thiazole (3.00 g, 13.27 mmol) in anhydrous tetrahydrofuran (100 ml). The reaction is stirred for 1 h, then iodomethane (2.48 ml, 39.8 mmol) is added and the reaction stirred for 45 minutes. The reaction is quenched with water and poured in aqueous saturated brine solution (200 ml) and extracted with ethyl acetate (3×100 ml).

The ethyl acetate is dried over anhydrous Na$_2$SO$_4$, filtered, and concentrated. The crude product is purified by flash chromatography on silica gel eluting with 20% ethyl acetate/hexanes to yield (2.52 g, 92%) of 4-chloro-5-([1,3]dioxolan- 2-yl)-2-methyl-thiazole: mass spectrum (ion spray): m/z=206.0 (M+1); $^1$H NMR (CDCl$_3$): δ=6.10 (1H, s), 4.18-4.01 (4H,m), 2.69 (3H, s).

(ii) 4-Chloro-2-methyl-thiazole-5-carboxaldehyde is made in 88% yield by the method of example 31(iii), using 4-chloro-5-([1,3]dioxolan-2-yl)-2-methyl-thiazole: mass spectrum (ion spray): m/z=160.0 (M−1); $^1$H NMR (CDCl$_3$): δ=10.04 (1H, s), 2.80 (3H, s).

(iii) The title compound is prepared by the methods in example 30(i), 30(ii), 30(iii) and 30(iv) using 4-chloro-2-methyl-thiazole-5-carboxaldehyde: mass spectrum (ion spray): m/z=302.2 (M+1); $^1$H NMR (CD$_3$OD): δ=4.44 (2H, s), 3.82 (2H, s), 3.48 (2H, brd), 3.02-2.92 (2H, m), 2.88-2.79 (1H, m), 2.66 (3H, s), 2.35 (2H, d), 2.00 (2H, brd), 1.85-1.69 (3H, m), 0.93 (6H, d).

EXAMPLE 33

N-(2-Methylpropyl)-N-[[(2,4-dichloro-1,3-thiazol-5-yl)methyl]piperidin-4-amine tartrate

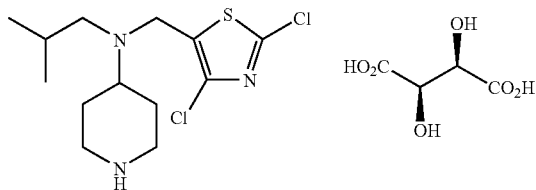

The title compound is prepared by the methods 30(i), 30(ii), 30(iii) and 30(iv) using 2,4-dichloro-thiazole-5-carboxaldehyde: mass spectrum (ion spray): m/z=322.1 (M+1); $^1$H NMR (CD$_3$OD): δ=4.02 (2H, s), 3.76 (2H, s), 3.30 (2H, brd), 2.90-2.74 (3H, m), 2.25 (2H, d), 1.81 (2H, brd), 1.73-1.61 (3H, m), 0.86 (6H, d).

EXAMPLE 34

N-(2-Methylpropyl)-N-[(2,4-dichloro-1,3-thiazol-5-yl)methyl]piperidin-4-amine tartrate hydrate

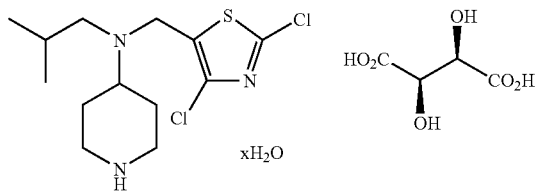

(i) To a solution of 2,4-dichlorothiazol-5-carboxaldehyde (159.3 g, 0.88 mol) in 2.5 L of 1,2-dichloroethane, are added 4-amino-piperidine-1-carboxylic acid t-butyl ester (178.7 g, 0.89 mol, 1.02 equiv. mol) and acetic acid (53.6 g, 0.89 mol, 1.02 equiv. mol); addition of acetic acid is exothermic, temperature increases from 21° C. to 26° C. The in-situ formation of imine is monitored by $^1$H NMR; after 1.5 h 90% of imine is formed. Then sodium triacetoxy borohydride is added (283 g, 1.3 mol, 1.5 equiv. mol) in three fractions over 10 minutes. An exothermic reaction takes place and the temperature reaches 27° C. After 4.3 h at room temperature the reaction mixture is then quenched with 1.3 L water and sodium hydroxide (460 ml); the addition of sodium hydroxide is exothermic (T=36° C.). The mixture is then extracted with 2.5 L of methyl t-butyl ether (MTBE). The yellow organic layer is washed with 2.2 L of 3% sodium hydroxide solution then with 2 L brine. The organic layer is concentrated under vacuum, then 1 L MTBE is added and concentrated to dryness again to remove remaining water. The crude product of 4-{[(2,4-dichloro-thiazol-5-yl)methyl]-amino}-piperidine-1-carboxylic acid t-butyl ester is then isolated as yellow oil 334 g (becoming crystalline overnight at room temperature) the crude yield is 100% (HPLC 90% area, KF=0.2% water). Mass spectrum (ion spray): m/z=366 (M+1); $^1$H NMR (250 MHz, CDCl$_3$): δ=3.87 (2H, brd), 3.80 (2H, s), 2.66 (2H, brs), 2.50 (1H, m), 1.72 (2H, brd), 1.31 (10H, s), 1.09 (2H, m), 13C NMR (62 MHz, CDCl3): δ=155.13, 150.58, 135,65, 132.83, 79.96, 57.00, 54.64, 42.59, 32.77, 28.81.

(ii) To a solution of 4-{[(2,4-dichloro-thiazol-5-yl)methyl]-amino}-piperidine-1-carboxylic acid t-butyl ester (330 g, 0.9 mol, 1 equiv. mol) in 3.5 L MTBE is added acetic acid (57.2 g, 0.95 mol, 1.06 equiv. mol), isobutyraldehyde (97.3 g, 1.35 mol, 1.5 equiv. mol) and sodium triacetoxy borohydride (305 g, 1.44 mol, 1.6 equiv. mol) suspension in 0.5 L of MTBE. A slight exotherm takes place temperature increases from 24 to 26° C. After 5 h at room temperature the reaction mixture is quenched with 1.3 L water and 30% sodium hydroxide (500 ml). The yellow organic upper phase is washed with 2 L water, then with 2 L of brine. The organic layer is then concentrated under vacuum. The crude product is isolated as yellow powder, 395 g (HPLC 92% area), contaminated by ~7% of (2,4-dichloro-thiazol-5-yl)-methanol. Purification is done by dissolution of the crude in 900 ml isopropanol/water 8/2 v/v, stirring at 80° C. until complete dissolution, then cool down to room temperature. Filtered at 0° C., the solid is washed with 150 ml of cold isopropanol. The cake is then dried under vacuum at 50° C., to afford 4-{[(2,4-dichloro-thiazol-5-yl)methyl]-isobutyl-amino}-piperidine-1-carboxylic acid t-butyl ester as a white crystalline powder, 293 g (78% yield for the two first steps). Mass spectrum (ion spray): m/z=422 (M+1); $^1$H NMR (250 MHz, CDCl$_3$): δ=4.35 (2H, brd), 3.87 (2H, s), 2.80 (3H, m), 2.42 (2H,d), 1.86 (3H, m), 1.61 (11H, m), 1.06 (6H, d); $^{13}$C NMR (62 MHz, CDCl$_3$): δ=155.02, 150.71, 137.29, 132.52, 79.95, 58.81, 58.44, 47.64, 43.93, 28.82, 28.03, 27.48, 21.03.

(iii) To a mixture of water (850 ml) and concentrated hydrochloric acid (240 ml) is added a solution of 4-{[(2,4-dichloro-thiazol-5-yl)methyl]-isobutyl-amino}-piperidine-1-carboxylic acid t-butyl ester (304.5 g, 0.72 mol) in THF (600 ml) dropwise at 65° C. The addition and reaction are complete in 40 minutes. THF is then stripped under vacuum; residual aqueous layer is extracted with 2 L MTBE (to remove remaining (2,4-dichloro-thiazol-5-yl)-methanol). Neutralized by addition of NaOH (30%, 200 ml) and extracted twice with MTBE (1.5 L). Combined organic layers are washed with brine (3 L) then clarified (to remove insoluble). The organic layer is then concentrated under vacuum to afford 220 g of N-(2-methylpropyl)-N-[(2,4-dichloro-1,3-thiazol-5-yl) methyl]piperidin-4-amine as a pink powder. Yield 95% (HPLC=99% area). Mass spectrum (ion spray): m/z=322 (M+1); $^1$H NMR (400 MHz, CDCl$_3$): δ=3.73 (2H, s), 3.17 (2H, m), 2.56 (3H, m). 2.31 (2H, d), 2.17 (1H, s, NH), 1.76 (2H, m), 1.68 (1H, m), 1.46 (2H, m), 0.92 (6H, d); $^{13}$C NMR (100 MHz, CDCl$_3$): δ=20.6, 27.09, 28.88, 46.39, 47.20, 58.10, 58.52, 131.88, 137.30, 150.13.

(iv) To a solution of N-(2-methylpropyl)-N-[(2,4-dichloro-1,3-thiazol-5-yl)methyl]piperidin-4-amine (193.6 g, 0.6 mol) in 2 L THF at 65° C. are added seed crystals and L-tartaric acid (90.15 g, 0.6 mol, 1 equiv.) solution in 100 ml water dropwise over 5 min (after 15 min the solution becomes turbid and the product begins to crystallize). After 3 h at 64° C., the mixture is cooled down to room temperature, and then stirred for an additional 20 h. The reaction mixture is then cooled down to 10° C. and filtered; the solid is washed with cold THF/water 95/5 and dried under vacuum to afford 245.8 g of N-(2-methylpropyl)-N-[(2,4-dichloro-1,3-thiazol-5-yl)methyl]piperidin-4-amine tartrate hemihydrate (87% yield). $^1$H NMR (250 MHz, DMSO d6): δ=3.97 (2H, s), 3.69 (2H, s), 3.24 (2H, brd), 2.77 (3H, m), 2.20 (2H, d), 1.63 (5H, m), 0.80 (6H, d); $^{13}$C NMR (62 MHz, DMSO d6): δ=175.09, 149.48, 138.32, 131.24, 72.39, 58.12, 55.08, 47.04, 43.29, 26.72, 24.60, 20.81.

(v) A suspension of hemihydrate salt (218.6 g, 0.46 mol) in 1.5 L THF and 75 ml of water is stirred at room temperature. After 20 h at room temperature 15 ml of water is then added and the mixture is stirred for an additional 2 h to achieve complete transformation. The mixture is then cooled down to 5° C. and filtered; the cake is dried at 50° C. under vacuum overnight to afford 202.8 g of the title product (yield 92%)

EXAMPLE 35

N-(Cyclopropylmethyl)-N-[[(2,4-dimethyl-1,3-thiazol-5-yl)methyl]piperidin-4-amine tartrate

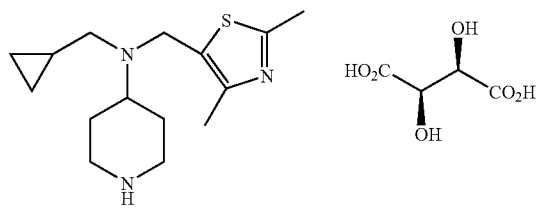

(i) Sodium triacetoxyborohydride (1.80 g, 8.49 mmol) is added to a stirred solution of 4-{[(2,4-dimethyl-thiazol-5-yl)methyl]-amino}-piperidine-1-carboxylic acid tert-butyl ester (1.71 g, 5.25 mmol), cyclopropanecarboxaldehyde (0.44 ml, 5.89 mmol), acetic acid (0.32 ml, 5.59 mmol), and 1,2-dichloroethane (35 ml). The reaction is stirred for 25 h at room temperature under nitrogen. The reaction is poured into 2N NaOH (100 ml) and extracted with ethyl acetate (100 ml×3). The ethyl acetate is dried over sodium sulfate and then the sodium sulfate is filtered off. The crude product is concentrated on a rotary evaporator and purified by flash chromatography on silica gel eluting with 40% ethyl acetate/hexanes to yield (1.98 g, 99%) of 4-{[cyclopropylmethyl-(2,4-dimethyl-thiazol-5-ylmethyl)]-amino}-piperidine-1-carboxylic acid tert-butyl ester: mass spectrum (ion spray): m/z=380.3 (M+1); $^1$H NMR (CDCl$_3$): δ=4.18 (2H, brs), 3.74 (2H, s), 2.86-2.78 (1H, m), 2.70-2.60 (5H, m), 2.41 (2H, d), 2.32 (3H, s), 1.81-1.70 (2H, m), 1.50-1.39 (11H, m), 0.87-0.80 (1H, m), 0.53-0.46 (2H, m), 0.12-0.06 (2H, m).

(ii) 4-{[Cyclopropylmethyl-(2,4-dimethyl-thiazol-5-ylmethyl)]-amino}-piperidine-1-carboxylic acid tert-butyl ester (1.96 g, 5.18 mmol) is added to a stirred solution of dichloromethane (5 ml) and anisole (9.0 ml, 82.8 mmol). The reaction is cooled to 0° C. Trifluoroacetic acid (6.0 ml, 72.9 mmol) is then added. The reaction is stirred for 20 minutes at 0° C. and then for 5 h at room temperature. The reaction is loaded onto a pre-washed SCX-2 (10 g) column and washed with methanol (200 ml). The product is then eluted off with 2M ammonia in methanol (100 ml) and concentrated on a rotary evaporator to yield (1.25 g, 87%) of N-(cyclopropylmethyl)-N-[(2,4-dimethyl-1,3-thiazol-5-yl)methyl]piperidin-4-amine: mass spectrum (ion spray): m/z=280.2 (M+1); $^1$H NMR (CDCl$_3$): δ=3.75 (2H, s), 3.19-3.11 (2H, m), 2.81-2.73 (1H, m), 2.65-2.52 (5H, m), 2.42 (2H, d), 2.32 (3H, s), 1.76 (3H, brd), 1.50-1.38 (2H, m), 0.89-0.80 (1H, m), 0.52-0.44 (2H, m), 0.11-0.05 (2H, m).

(iii) N-(Cyclopropylmethyl)-N-[(2,4-dimethyl-1,3-thiazol-5-yl)methyl]piperidin-4-amine (1.25 g, 4.46 mmol) and L-Tartaric acid (0.67 g, 4.46 mmol) are dissolved in methanol (25 ml). The solution is stirred for 1.5 h and concentrated. The solid is dried in a vacuum oven overnight to yield (1.86 g, 97%) N-(cyclopropylmethyl)-N-[(2,4-dimethyl-1,3-thiazol-5-yl)methyl]piperidin-4-amine tartrate: mass spectrum (ion spray): m/z=280.2 (M+1); $^1$H NMR (CD$_3$OD): δ=4.45 (2H, s), 3.87 (2H, s), 3.45 (2H, brs), 3.11-2.93 (3H, m), 2.62 (3H, s), 2.45 (2H, d), 2.32 (3H, s), 2.02 (2H, brd), 1.96-1.76 (2H, m), 0.95-0.85 (1H, m), 0.56-0.49 (2H, m), 0.17-0.10 (2H, m).

EXAMPLE 36

N-(2-Cyclopropylmethyl)-N-[(4-chloro-2-methyl-1,3-thiazol-5-yl)methyl]piperidin-4-amine tartrate

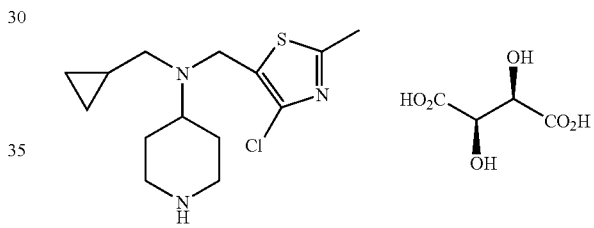

(i) 4-[(4-Chloro-2-methyl-thiazol-5-ylmethyl)-cyclopropylmethyl-amino]-piperidine-1-carboxylic acid tert-butyl ester is made in 70% yield by the method of example 35(i), using 4-[(4-chloro-2-methyl-thiazol-5-ylmethyl)-amino]-piperidine-1-carboxylic acid tert-butyl ester: mass spectrum (ion spray): m/z=400.2 (M+1); $^1$H NMR (CDCl$_3$): δ=4.19 (2H, brs), 3.81 (2H, s), 2.84-2.74 (1H, m), 2.70-2.64 (4H, m), 2.43 (2H, d), 1.74 (3H, brd), 1.51-1.38 (11H, m), 0.87-0.79 (1H, m), 0.52-0.46 (2H, m), 0.14-0.07 (2H, m).

(ii) N-(Cyclopropylmethyl)-N-[(4-chloro-2-methyl-1,3-thiazol-5-yl)methyl]piperidin-4-amine is made in 95% yield by the method of example 35(ii), using 4-[(4-chloro-2-methyl-thiazol-5-ylmethyl)-cyclopropylmethyl-amino]-piperidine-1-carboxylic acid tert-butyl ester: mass spectrum (ion spray): m/z=300.1 (M+1); $^1$H NMR (CDCl$_3$): δ=3.82 (2H, s), 3.16 (2H, brd), 2.79-2.69 (1H, m), 2.66 (3H, s), 2.62-2.54 (2H, m), 1.78 (2H, brd), 1.68 (1H, brs), 1.50-1.37 (2H, m), 0.89-0.79 (1H, m), 0.52-0.46 (2H, m), 0.14-0.08 (2H, m).

(iii) N-(Cyclopropylmethyl)-N-[(4-chloro-2-methyl-1,3-thiazol-5-yl)methyl]piperidin-4-amine tartrate is made in 91% yield by the method of example 35(iii): mass spectrum (ion spray): m/z=300.1 (M+1); $^1$H NMR (CD$_3$OD): δ=4.44 (2H, s), 3.91 (2H, s), 3.49 (2H, brd), 3.08-2.95 (3H, m), 2.65 (3H, s), 2.51 (2H, d), 2.03 (2H, brd), 1.86-1.74 (2H, m), 0.94-0.84 (1H, m), 0.56-0.49 (2H, m), 0.19-0.13 (2H, m).

EXAMPLE 37

N-(2-Cyclopropylmethyl)-N-[(4-chloro-2-methoxy-1,3-thiazol-5-yl)methyl]piperidin-4-amine tartrate

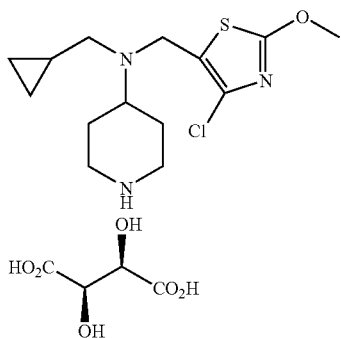

(i) 4-{[(4-Chloro-2-methoxy-thiazol-5-yl)methyl]-cyclopropylmethyl-amino}-piperidine-1-carboxylic acid tert-butyl ester is made in 94% yield by the method of example 35(i), using 4-{[(4-chloro-2-methoxy-thiazol-5-yl)methyl]-amino}-piperidine-1-carboxylic acid tert-butyl ester: mass spectrum (ion spray): m/z=416.2 (M+1); $^1$H NMR (CDCl$_3$): δ=4.19 (2H, brs), 4.06 (3H, s), 3.73 (2H, s), 2.86-2.76 (1H, m), 2.71-2.62 (2H, brm), 2.43 (2H, d), 1.74 (2H, brd), 1.51-1.37 (11H, m), 0.88-0.80 (1H, m), 0.54-0.48 (2H, m), 0.15-0.08 (2H, m).

(ii) N-(Cyclopropylmethyl)-N-[(4-chloro-2-methyoxy-1,3-thiazol-5-yl)methyl]piperidin-4-amine is made in 97% yield by the method of example 35(ii), using 4-{[(4-chloro-2-methoxy-thiazol-5-yl)methyl]-cyclopropylmethyl-amino}-piperidine-1-carboxylic acid tert-butyl ester: mass spectrum (ion spray): m/z=316.1 (M+1); $^1$H NMR (CDCl$_3$): δ=4.07 (3H, s), 3.75 (2H, s), 3.19-3.12 (2H, m), 2.80-2.71 (1H, m), 2.63-2.55 (2H, m), 2.45 (2H, d), 1.78 (2H, brd), 1.59 (1H, brs), 1.50-1.37 (2H, m), 0.89-0.80 (1H, m), 0.54-0.47 (2H, m), 0.15-0.09 (2H, m).

(iii) N-(Cyclopropylmethyl)-N-[(4-chloro-2-methyoxy-1,3-thiazol-5-yl)methyl]piperidin-4-amine tartrate is made in 98% yield by the method of example 35(iii): mass spectrum (ion spray): m/z=316.1 (M+1); $^1$H NMR (CD$_3$OD): δ=4.44 (2H, s), 4.05 (3H, s), 3.84 (2H, s), 3.45 (2H, brd), 3.10-2.97 (3H, m), 2.51 (2H, d), 2.03 (2H, brd), 1.85-1.74 (2H, m), 0.95-0.87 (1H, m), 0.58-0.52 (2H, m), 0.20-0.13 (2H, m).

EXAMPLE 38

N-(3-Methylbutyl)-N-[(benzofuran-2-yl)methyl]piperidin-4-amine dihydrochloride

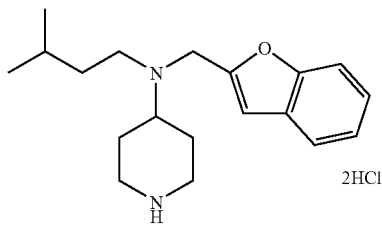

(i) Sodium triacetoxyborohydride (24.9 g, 117.48 mmol) is added to a stirred solution of 1-Boc-4-piperidone (15.6 g, 78.3 mmol), iso-amyl amine (10.0 ml, 86.15 mmol), and dichloromethane (400 ml). The reaction is stirred overnight at room temperature under nitrogen. The reaction is diluted with water and aqueous saturated NaHCO$_3$, and extracted with dichloromethane (150 ml×3). The dichloromethane is concentrated under vacuum, diluted with ethyl acetate and washed with aqueous saturated NaHCO$_3$, dried over Na$_2$SO$_4$, filtered, and concentrated to yield (19.99 g) of 4-(3-methyl-butylamino)-piperidine-1-carboxylic acid tert-butyl ester: mass spectrum (ion spray): m/z=271 (M+1); $^1$H NMR (CDCl$_3$): δ=4.05 (2H, brs), 2.84-2.73 (2H, brm), 2.67-2.55 (2H, m), 1.84 (2H, brd), 1.67-1.58 (1H, m), 1.51-1.44 (10H, m), 1.41-1.33 (2H, m), 1.30-1.18 (2H, m), 0.90 (6H, d).

(ii) Sodium triacetoxyborohydride (0.88 g, 4.16 mmol) is added to a stirred solution of 4-(3-methyl-butylamino)-piperidine-1-carboxylic acid tert-butyl ester (0.75 g, 2.77 mmol), benzofuran-2-carboxaldehyde (0.50 g, 3.46 mmol), and dichloromethane (14 ml). The reaction is stirred overnight at room temperature under nitrogen. The reaction is poured into aqueous saturated NaHCO$_3$ (50 ml) and extracted with dichloromethane (25 ml×3). The organic layer is washed with aqueous saturated NaHCO$_3$ and dried over Na$_2$SO$_4$, and filtered. The crude product is concentrated on a rotary evaporator and purified by flash chromatography on silica gel eluting with 0-30% (1:2 (10% NH$_4$OH in methanol):ethanol) to yield (1.17 g) of 4-{[(benzofuran-2-yl)methyl]-(3-methylbutyl)-amino}-piperidine-1-carboxylic acid tert-butyl ester: mass spectrum (ion spray): m/z=401 (M+1); $^1$H NMR (CDCl$_3$): δ=7.57-7.41 (2H, m), 7.30-7.16 (2H, m), 6.55 (1H, s), 4.15 (2H, brs), 3.81 (2H, s), 2.75-2.56 (6H, m), 1.80 (2H, brd), 1.63-1.53 (3H, m), 1.46 (9H, s), 1.42-1.33 (1H, m), 0.92-0.85 (6H, m).

(iii) Trifluoroacetic acid (15 ml, 195 mmol) is added to a solution of 4-{[(benzofuran-2-yl)methyl]-(3-methylbutyl)-amino}-piperidine-1-carboxylic acid tert-butyl ester (1.17 g, 2.92 mmol) in dichloromethane (15 ml). The reaction is stirred overnight at room temperature. The reaction is concentrated and water added to the residue. The solution is loaded onto a SCX-2 (10 g) column and washed with water (20 ml) and methanol (20 ml). The product is then eluted off with 2M ammonia in methanol (30 ml) and concentrated on a rotary evaporator to yield (0.77 g) of N-(3-methylbutyl)-N-[(benzofuran-2-yl)methyl]piperidin-4-amine: mass spectrum (ion spray): m/z=301 (M+1); $^1$H NMR (CDCl$_3$): δ=7.52-7.43 (2H, m), 7.25-7.16 (2H, m), 6.56 (1H, s), 3.81 (2H, s), 3.14 (2H, brd), 2.72-2.52 (5H, m), 1.86-1.75 (3H, brm), 1.64-1.34 (5H, m), 0.92-0.83 (6H, m).

(iv) N-(3-Methylbutyl)-N-[(benzofuran-2-yl)methyl]piperidin-4-amine (0.09 g, 0.28 mmol) is dissolved in methanol (2 ml). 2.0 M HCl in diethyl ether (0.29 ml, 0.57 mmol) is added and the reaction stirred for 2 hours. The reaction is concentrated and the solid dried in a vacuum (60° C.) overnight to yield (0.77 g) of N-(3-methylbutyl)-N-[(benzofuran-2-yl)methyl]piperidin-4-amine dihydrochloride: mass spectrum (ion spray): m/z=301 (M+1).

EXAMPLE 39

N-(3-Methylbutyl)-N-[(1,3-thiazol-2-yl)methyl]piperidin-4-amine dihydrochloride

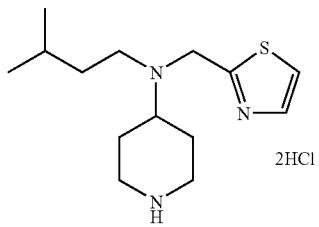

(i) Sodium triacetoxyborohydride (0:30 g, 1.42 mmol) is added to a stirred solution of 4-(3-methyl-butylamino)-piperidine-1-carboxylic acid tert-butyl ester (0.19 g, 0.71 mmol), 2-thiazolecarboxaldehyde (0.12 ml, 1.42 mmol), and dichloromethane (3.5 ml). The reaction is stirred overnight at room temperature under nitrogen. The reaction is diluted with ethyl acetate, washed with aqueous saturated NaHCO₃, dried over Na₂SO₄, filtered, and concentrated. Water is added to the residue, and the solution loaded onto a SCX-2 (10 g) column and washed with water (20 ml) and methanol (20 ml). The product is then eluted with 2M ammonia in methanol (30 ml). The filtrate is concentrated and the crude material purified on silica gel eluting with 0-50% ethyl acetate/hexanes to yield (0.20 g) of 4-{(3-methyl-butyl)-[(thiazol-2-yl)-methyl]-amino}-piperidine-1-carboxylic acid tert-butyl ester: mass spectrum (ion spray): m/z=368 (M+1); ¹H NMR (CDCl₃): δ=7.67 (1H, d), 7.23 (1H, d), 4.17 (2H, brs), 3.93 (2H, s), 2.72-2.54 (5H, m), 1.78 (2H, brd), 1.7-1.57 (2H, m), 1.45-1.41 (10H, m), 1.40-1.32 (2H, m), 0.87 (6H, d).

(iii) Trifluoroacetic acid (2.7 ml, 35 mmol) is added to a solution of 4-{(3-methyl-butyl)-[(thiazol-2-yl)-methyl]-amino}-piperidine-1-carboxylic acid tert-butyl ester (0.20 g, 0.55 mmol) in dichloromethane (2.7 ml). The reaction is stirred for 1 hour at room temperature. The reaction is concentrated, loaded onto a SCX-2 (5 g) column, and washed with water (50 ml) and methanol (50 ml). The product is then eluted off with 2M ammonia in methanol (100 ml) and concentrated on a rotary evaporator to yield (0.14 g) of N-(3-methylbutyl)-N-[(1,3-thiazol-2-yl)methyl]piperidin-4-amine: mass spectrum (ion spray): m/z=268 (M+1); ¹H NMR (CDCl₃): δ=7.67 (1H, d), 7.22 (1H, d), 3.95 (2H, s), 3.16-3.09 (2H, m), 2.67-2.49 (5H, m), 1.81 (2H, brd), 1.69-1.57 (2H, m), 1.50-1.32 (4H, m), 0.87 (6H, d).

(iv) N-(3-methylbutyl)-N-[(1,3-thiazol-2-yl)methyl]piperidin-4-amine (0.13 g, 0.48 mmol) is dissolved in acetonitrile (0.5 ml). 1.0 M HCl (1.93 ml, 1.93 mmol) is added and solution placed under lyophilization conditions to yield (0.166 g) of N-(3-methylbutyl)-N-[(1,3-thiazol-2-yl)methyl]piperidin-4-amine dihydrochloride: mass spectrum (ion spray): m/z=268 (M+1); ¹H NMR (DMSO-d₆): δ=9.49-9.41 (1H, brd), 9.28-9.19 (1H, brm), 7.94 (2H, dd), 6.42 (1H, brs), 4.77 (2H, s), 3.67-3.56 (1H, brm), 3.38 (2H, d), 3.17-3.09 (2H, brm), 2.94-2.82 (2H, brm), 2.95-2.81 (2H, m), 2.31 (2H, brs), 2.21-2.08 (2H, m), 1.68-1.46 (3H, m), 0.84 (6H, d).

EXAMPLE 40

N-(2-Methylpropyl)-N-[(4-chloro-1,3-thiazol-5-yl)methyl]piperidin-4-amine tartrate

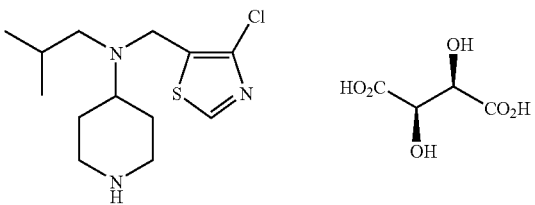

Method 1

(i) n-BuLi (1.6M in hexanes, 0.50 mL, 0.8 mmol) is added to a cold (−78° C.) solution of (2,4-dichloro-thiazol-5-ylmethyl)-isobutyl-piperdin-4-yl-amine (0.0995 g, 0.3 mmol) in anhydrous tetrahydrofuran. After stirring for 1 h at −78° C., aqueous saturated NaHCO₃ is added, then poured in 100 mL aqueous saturated NaHCO₃, extracted with ethyl acetate (3×100 mL). The layers are separated and the organic layer dried over Na₂SO₄, filtered, and concentrated. The crude material is purified on silica gel eluting with 1% NH₄OH/10% ethanol/chloroform to yield (0.069 g, 78%) N-(2-methylpropyl)-N-[(4-chloro-1,3-thiazol-5-yl)methyl]piperidin-4-amine: mass spectrum (ion spray): m/z=288.1 (M+1); ¹H NMR (CDCl₃): δ=8.64 (1H, s), 3.81 (2H, s), 3.16 (2 H, brd), 2.60-2.49 (3H, m), 2.32 (2H, d), 1.82-1.62 (4H, m), 1.53-1.39 (2H, m), 0.91 (6H, d).

(ii) N-(2-Methylpropyl)-N-[(4-chloro-1,3-thiazol-5-yl)methyl]piperidin-4-amine tartrate is made in 93% yield by the method of example 35(iii), using N-(2-methylpropyl)-N-[(4-chloro-1,3-thiazol-5-yl)methyl]piperidin-4-amine: mass spectrum (ion spray): m/z=288.1 (M+1); ¹H NMR (CD₃OD): δ=8.91 (1H, s), 4.44 (2H, s), 3.90 (2H, s), 3.48 (2H, brd), 3.03-2.93 (2H, m), 2.89-2.81 (1H, m), 2.37 (2H, d), 2.03 (2H, brd), 1.86-1.70 (3H, m), 0.94 (6H, d).

Method 2

(i) Add p-toluenesulfonic acid monohydrate (1.70 g, 8.94 mmol) to a stirred solution of 2,4-dichloro-thiazole-5-carbaldehyde (21.05 g, 116 mmol), ethylene glycol (20.0 mL, 359 mmol), and anhydrous toluene (300 mL). Add a Dean-Stark trap and heat the reaction to reflux under nitrogen for 7 h. Cool the reaction and pour it into 10% sodium carbonate (300 mL). Extract with ethyl acetate (3×150 mL) and wash with brine (150 mL). Dry the ethyl acetate over sodium sulfate and then filter off the sodium sulfate. Concentrate on a rotary evaporator and purify the crude product by flash chromatography on silica gel eluting with 10% ethyl acetate/hexanes to yield 24.77 g (95%) of 2,4-dichloro-5-[1,3]dioxolan-2-yl-thiazole: mass spectrum (ion spray): m/z=225.9 (M+1); ¹H NMR (CDCl₃): δ=6.08 (s, 1H), 4.19-4.03 (m, 4H).

(ii) Slowly add n-butyllithium (2.5 M in hexanes, 44.0 mL, 110 mmol) to a stirred solution of 2,4-dichloro-5-[1,3]dioxolan-2-yl-thiazole (19.33 g, 85.5 mmol) and anhydrous tetrahydrofuran (400 mL) at −78° C. under nitrogen. Stir for 1.5 h at −78° C. and then quench with water and pour the reaction into brine (300 mL). Extract with ethyl acetate (3×200 mL), dry over sodium sulfate, and filter off the sodium sulfate. Concentrate on a rotary evaporator and purify the crude product by flash chromatography on silica gel eluting with 25% ethyl acetate/hexanes to yield 15.27 g (93%) of 4-chloro-5-

[1,3]dioxolan-2-yl-thiazole: mass spectrum (ion spray): m/z=192.0 (M+1); $^1$H NMR (CDCl$_3$): δ=8.75 (s, 1H), 6.18 (s, 1H), 4.22-4.04 (m, 4H).

(iii) Add 5 N HCl (50 mL, 250 mmol) to a stirred solution of 4-chloro-5-[1,3]dioxolan-2-yl-thiazole (19.2482 g, 100 mmol) and tetrahydrofuran (250 mL). Stir the reaction for 1.5 h at room temperature. Pour the reaction into brine (300 mL) and extract with ethyl acetate (3×100 mL). Wash the ethyl acetate with saturated sodium bicarbonate (150 mL) and then with brine (100 mL). Dry the ethyl acetate over sodium sulfate and filter off the sodium sulfate. Concentrate on a rotary evaporator and purify the crude product by flash chromatography on silica gel eluting with 20% ethyl acetate/hexanes to yield 13.09 g (88%) of 4-chloro-thiazole-5-carbaldehyde: $^1$HNMR (CDCl$_3$): δ=10.13 (s, 1H), 9.04 (s, 1H).

(iv) Add sodium triacetoxyborohydride (30.50 g, 144 mmol) to a stirred solution of 4-amino-1-N-Boc-piperidine (18.00 g, 89.9 mmol), 4-chloro-thiazole-5-carbaldehyde (13.09 g, 88.7 mmol), acetic acid (5.5 mL, 96.1 mmol), and 1,2-dichloroethane (350 mL). Stir the reaction for 18 hours at room temperature under nitrogen. Pour the reaction into 2N NaOH (400 mL) and extract with ethyl acetate (3×150 mL). Wash the ethyl acetate with brine (2×150 mL). Dry the ethyl acetate over sodium sulfate and then filter off the sodium sulfate. Concentrate on a rotary evaporator and purify the crude product by flash chromatography on silica gel eluting with 75% ethyl acetate/hexanes then with 100% ethyl acetate to yield 21.78 g (74%) of 4-{[(4-chloro-thiazol-5-yl)methyl]-amino}-piperidine-1-carboxylic acid tert-butyl ester: mass spectrum (ion spray): m/z=332.1 (M+1); $^1$H NMR (CDCl$_3$): δ=8.67 (s, 1H), 4.10-4.02 (m, 4H), 2.88-2.82 (m, 2H), 2.74-2.67 (m, 1H), 1.92-1.89 (m, 2H), 1.49 (s, 9H), 1.37-1.28 (m, 3H).

(v) Add sodium triacetoxyborohydride (24.00 g, 113 mmol) to a stirred solution of 4-{[(4-chloro-thiazol-5-yl)methyl]-amino}-piperidine-1-carboxylic acid tert-butyl ester (21.78 g, 65.6 mmol), isobutyraldehyde (9.0 mL, 99.1 mmol), acetic acid (4.0 mL, 69.9 mmol), and 1,2-dichloroethane (260 mL). Stir the reaction for 18 hours at room temperature under nitrogen. Pour the reaction into 2N NaOH (300 mL) and extract with ethyl acetate (3×150 mL). Wash the ethyl acetate with brine (2×150 mL). Dry the ethyl acetate over sodium sulfate and then filter off the sodium sulfate. Concentrate on a rotary evaporator and purify the crude product by flash chromatography on silica gel eluting with 25% ethyl acetate/hexanes to yield 24.67 g (97%) of 4-{[(4-chloro-thiazol-5-yl)methyl]-isobutyl-amino}-piperidine-1-carboxylic acid tert-butyl ester: mass spectrum (ion spray): m/z=388.2 (M+1); $^1$H NMR (CDCl$_3$): δ=8.65 (s, 1H), 4.21 (br s, 2H), 3.80 (s, 2H), 2.63-2.56 (m, 3H), 2.29 (d, 2H), 1.77-1.65 (m, 3H), 1.50-1.41 (m, 11H), 0.92 (d, 6H).

(vi) Add 4-{[(4-chloro-thiazol-5-yl)methyl]-isobutyl-amino}-piperidine-1-carboxylic acid tert-butyl ester (23.49 g, 60.6 mmol) to dichloromethane (140 mL) and cool to 0° C. Slowly add trifluoroacetic acid (47.0 mL, 610 mmol) and stir for 15 minutes at 0° C. and three hours at room temperature. Cool the reaction to 0° C. and slowly add chilled 2 N NaOH (400 mL). Extract with ethyl acetate (3×200 mL), wash with 2 N NaOH (100 mL) and then with brine (100 mL). Dry the ethyl acetate over sodium sulfate and then filter off the sodium sulfate. Concentrate on a rotary evaporator and purify the crude product by flash chromatography on silica gel eluting with 1.2% concentrated ammonium hydroxide/12% ethanol/chloroform then with 2% concentrated ammonium hydroxide/20% ethanol/chloroform to yield 15.59 g (89%) of [(4-chloro-thiazol-5-yl)methyl]-isobutyl-piperidin-4-yl-amine: mass spectrum (ion spray): m/z=288.1 (M+1); $^1$H NMR (CDCl$_3$): δ=8.63 (s, 1H), 3.80 (s, 2H), 3.17-3.14 (m, 2H), 2.59-2.47 (m, 3H), 2.32 (d, 2H), 1.79-1.65 (m, 4H), 1.50-1.40 (m, 2H), 0.91 (d, 6H).

(vii) Add L-tartaric acid (8.08 g, 53.8 mmol) to absolute ethanol (300 mL) and heat until the L-tartaric acid goes into solution. Add this warm solution of L-tartaric acid to [(4-chloro-thiazol-5-yl)methyl]-isobutyl-piperidin-4-yl-amine (15.50 g, 53.9 mmol) in absolute ethanol (200 mL) at room temperature. Stir for 18 hours under nitrogen at room temperature. Cool the reaction to 0° C. and filter off the solid. Wash the solid with cold absolute ethanol and dry in a vacuum oven at 50° C. to yield 22.16 g (94%) of [(4-chloro-thiazol-5-yl)methyl]-isobutyl-piperidin-4-yl-amine L-tartrate: mass spectrum (ion spray): m/z=288.1 (M+1); $^1$H NMR (CDCl$_3$): δ=8.91 (s, 1H), 4.44 (s, 2H), 3.89 (s, 2H), 3.50-3.47 (m, 2H), 3.01-2.93 (m, 2H), 2.89-2.81 (m, 1H), 2.37 (d, 2H), 2.03-2.00 (m, 2H), 1.87-1.70 (m, 3H), 0.94 (d, 6H); LC/MS (90/5/5 to 0/95/5 water/acetonitrile/5% formic acid in water) XTerra MS C$_{18}$ 2.1 mm×50 mm×3.5 micron: Rt 0.96 minutes, Purity: 100%.

EXAMPLE 41

N-(2-Hydroxy-2-methylpropyl)-N-[(2,4-dichloro-1,3-thiazol-5-yl)methyl]piperidin-4-amine tartrate

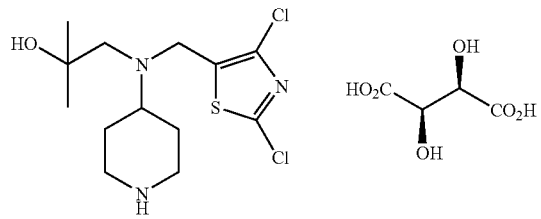

(i) Add sodium triacetoxyborohydride (1.70 g, 8.02 mmol) to a stirred solution of 4-amino-piperidine-1-carboxylic acid tert-butyl ester (1.0124 g, 5.06 mmol), 2,4-dichloro-thiazole-5-carbaldehyde (1.0113 g, 5.56 mmol), glacial acetic acid (0.31 mL, 5.42 mmol), and 1,2-dichloroethane (40 mL). Stir for 18 hours under nitrogen at room temperature. Pour the reaction into 2N NaOH (100 mL) and extract with ethyl acetate (3×100 mL). Dry the ethyl acetate over sodium sulfate and then filter off the sodium sulfate. Concentrate on a rotary evaporator and purify the crude product by flash chromatography on silica gel eluting with 35% ethyl acetate/hexanes then with 100% ethyl acetate to yield 1.1547 g (62%) of 4-{[(2,4-dichloro-thiazol-5-yl)methyl]-amino}-piperidine-1-carboxylic acid tert-butyl ester: mass spectrum (ion spray): m/z=366.1 (M+1); $^1$H NMR (CDCl$_3$): δ=4.04 (br s, 2H), 3.96 (s, 2H), 2.87-2.81 (m, 2H), 2.72-2.65 (m, 1H), 1.90-1.86 (m, 2H), 1.48-1.39 (m, 10H), 1.33-1.23 (m, 2H).

(ii) Add 2,2-dimethyl-oxirane (3.0 mL, 33.3 mmol) to a stirred suspension of lithium perchlorate (3.39 g, 31.9 mmol) in anhydrous acetonitrile (40 mL). Stir for one hour under nitrogen at room temperature. Add 4-{[(2,4-dichloro-thiazol-5-yl)methyl]-amino}-piperidine-1-carboxylic acid tert-butyl ester (1.1337 g, 3.10 mmol) in anhydrous acetonitrile (15 mL). Heat the reaction at reflux for 72 hours under nitrogen. Pour the reaction into saturated sodium bicarbonate (100 mL) and extract with ethyl acetate (3×100 mL). Dry the ethyl acetate over sodium sulfate and then filter off the sodium sulfate. Concentrate on a rotary evaporator and purify the crude product by flash chromatography on silica gel eluting with 30% ethyl acetate/hexanes to yield 0.4527 g (33%) of 4-{[(2,4-dichloro-thiazol-5-yl)methyl]-(2-hydroxy-2-methyl-propyl)-amino}-piperidine-1-carboxylic acid tert-butyl ester: mass spectrum (ion spray): m/z=438.2 (M+1); $^1$H NMR (CDCl$_3$): δ=4.22 (br s, 2H), 3.97 (s, 2H), 2.67-2.59 (m, 3H), 2.50 (s, 2H), 1.77-1.74 (m, 2H), 1.60 (s, 2H), 1.49 (s, 9H), 1.47-1.35 (m, 1H), 1.23 (s, 6H).

(iii) Add 4-{[(2,4-dichloro-thiazol-5-yl)methyl]-(2-hydroxy-2-methyl-propyl)-amino}-piperidine-1-carboxylic acid tert-butyl ester (0.4487 g, 1.02 mmol) to a stirred solution of dichloromethane (60 mL) and anisole (9.0 mL, 82.8 mmol). Cool the reaction to 0° C. Add the trifluoroacetic acid (6.0 mL, 72.9 mmol). Stir the reaction for 10 minutes at 0° C. and then for 2 hours at room temperature. The reaction is loaded directly onto a 10 g prepacked SCX-2 cartridge and washed with methanol (200 mL). The product is then eluted off with 2M ammonia in methanol (100 mL) and concentrated on a rotary evaporator to yield 0.3448 g (99%) of N-(2-hydroxy-2-methylpropyl)-N-[(2,4-dichloro-1,3-thiazol-5-yl)methyl]piperidin-4-amine: mass spectrum (ion spray): m/z=338.1 (M+1); $^1$H NMR (CDCl$_3$): δ=3.97 (s, 2H), 3.18-3.15 (m, 2H), 2.59-2.53 (m, 5H), 1.80-1.70 (m, 4H), 1.49-1.39 (m, 2H), 1.22 (s, 6H).

(iv) Add L-tartaric acid (0.1504 g, 1.00 mmol) to a stirred solution of methanol (12 mL), and N-(2-hydroxy-2-methyl-propyl)-N-[(2,4-dichloro-1,3-thiazol-5-yl)methyl]piperidin-4-amine (0.3386 g, 1.00 mmol). Stir the reaction for 2 hours at room temperature. Concentrate on a rotary evaporator to yield 0.4775 g (97%) of the title product: mass spectrum (ion spray): m/z=338.1 (M+1); LC/MS (90/5/5 to 0/95/5 water/acetonitrile/5% formic acid in water) XTerra MS C$_{18}$ 2.1 mm×50 mm×3.5 micron: Rt 1.64 minutes, Purity: >99%; $^1$H NMR (CD$_3$OD): δ=4.44 (s, 2H), 4.04 (s, 2H), 3.49-3.46 (m, 2H), 2.99-2.86 (m, 3H), 2.55 (s, 2H), 2.05-2.02 (m, 2H), 1.80-1.71 (m, 2H), 1.24 (s, 6H).

The compounds of the present invention are inhibitors of the uptake of one or more monoamines selected from serotonin, norepinephrine and dopamine. They work by selectively inhibiting one or more of the biogenic amine (serotonin, norepinephrine and dopamine) transporter proteins. Their selectivity profiles may be determined using the assays described below (see also J. Gobel, D. L. Saussy and A. Goetz, J. Pharmacol. Toxicolo. (1999), 42, 237-244). Compounds of formula (I) and their pharmaceutically acceptable salts preferably exhibit a K$_i$ value less than 500 nM at one or more of these monoamine transporter proteins as determined using the scintillation proximity assay as described below. The compounds of formula (I) exemplified above and their pharmaceutically acceptable salts exhibit a K$_i$ value less than 100 nM at one or more of these monoamine transporter proteins as determined using the assays described below. Preferred compounds of formula (I) and their pharmaceutically acceptable salts exhibit a K$_i$ value less than 50 nM at one or more of these monoamine transporter proteins. Especially preferred compounds of formula (I) and their pharmaceutically acceptable salts exhibit a K$_i$ value less than 20 nM at one or more of these monoamine transporter proteins. Preferably, compounds of the present invention which selectively inhibit one of the three biogenic amine transporters do so relative to the other two transporters by a factor of at least five, more preferably by a factor of at least ten. Preferably, compounds of the present invention which selectively inhibit two of the three biogenic amine transporters do so relative to the other transporter by a factor of at least five, more preferably by a factor of at least ten.

Biogenic amine transporters control the amount of neurotransmitters in the synaptic cleft. Inhibition of the respective transporter leads to a rise in that neurotransmitter. Inhibition of the individual transporters can be studied by a simple competitive binding assay using selective radioligands for the individual expressed human transporter site. Compounds may be compared for selectivity and potency on the human norepinephrine transporter (hNET), the h-serotonin transporter (hSERT) and the h-dopamine transporter (hDAT) using membranes prepared from HEK293 cells expressing the respective transporter site.

Advantageously, the compounds of the present invention also have a reduced interaction (both as substrate and inhibitor) with the liver enzyme Cytochrome P450 (CYP2D6). That is to say, they preferably exhibit less than 75% metabolism via the CYP2D6 pathway according to the CYP2D6 substrate assay described below and they preferably exhibit an IC50 of >6 μM according to the CYP2D6 inhibitor assay described below.

Generation of Stable Cell-lines Expressing the Human Dopamine, Norepinephrine and Serotonin Transporters Standard molecular cloning techniques are used to generate stable cell-lines expressing the human dopamine, norepinephrine and serotonin transporters. The polymerase chain reaction (PCR) is used in order to isolate and amplify each of the three full-length cDNAs from an appropriate cDNA library. Primers for PCR are designed using the following published sequence data:

Human dopamine transporter: GenBank M95167. Reference: Vandenbergh D J, Persico A M and Uhl G R. *A human dopamine transporter cDNA predicts reduced glycosylation, displays a novel repetitive element and provides racially-dimorphic TaqI RFLPs*. Molecular Brain Research (1992) volume 15, pages 161-166.

Human norepinephrine transporter: GenBank M65105. Reference: Pacholczyk T, Blakely, R D and Amara S G. *Expression cloning of a cocaine- and antidepressant-sensitive human noradrenaline transporter*. Nature (1991) volume 350, pages 350-354.

Human serotonin transporter: GenBank L05568. Reference: Ramamoorthy S, Bauman A L, Moore K R, Han H, Yang-Feng T, Chang A S, Ganapathy V and Blakely R D. *Antidepressant- and cocaine-sensitive human serotonin transporter: Molecular cloning, expression, and chromosomal localization*. Proceedings of the National Academy of Sciences of the USA (1993) volume 90, pages 2542-2546.

The PCR products are cloned into a mammalian expression vector (eg pcDNA3.1 (Invitrogen)) using standard ligation techniques. The constructs are then used to stably transfect HEK293 cells using a commercially available lipofection reagent (Lipofectamine™—Invitrogen) following the manufacture's protocol.

Norepinephrine Binding Assay

The ability of compounds to compete with [$^3$H]-Nisoxetine for its binding sites on cloned human norepinephrine membranes is used as a measure of its ability to block norepinephrine uptake via its specific transporter.

Membrane Preparation:

Cell pastes from large scale production of HEK-293 cells expressing cloned human noradrenaline transporters are homogenised in 4 volumes 50 mM Tris.HCl containing 300 mM NaCl and 5 mM KCl, pH 7.4. The homogenate is centrifuged twice (40,000 g, 10 min, 4° C.) with pellet re-suspension in 4 volumes Tris.HCl buffer after the first spin and 8 volumes after the second spin. The suspended homogenate is centrifuged (100 g, 10 min, 4° C.) and the supernatant kept and re-centrifuged (40,000 g, 20 min, 4° C.). The pellet is resuspended in Tris.HCl buffer containing the above reagents along with 10% w/v sucrose and 0.1 mM phenylmethylsulfonyl fluoride (PMSF). The membrane preparation is stored in aliquots (1 ml) at −80° C. until required. The protein concentration of the membrane preparation is determined using a bicinchoninic acid (BCA) protein assay reagent kit (available from Pierce).

[$^3$H]-Nisoxetine Binding Assay:

Each well of a 96well microtitre plate is set up to contain the following:

50 μl 2 nM [N-methyl-$^3$H]-Nisoxetine hydrochloride (70-87 Ci/mmol, from NEN Life Science Products)

75 μl Assay buffer (50 mM Tris.HCl pH 7.4 containing 300 mM NaCl and 5 mM KCl)

25 μl Test compound, assay buffer (total binding) or 10 μM Desipramine HCl (non-specific binding)

50 μl Wheatgerm agglutinin coated poly(vinyltoluene) (WGA PVT) SPA Beads (Amersham Biosciences RPNQ0001) (10 mg/ml)

50 μl Membrane (0.2 mg protein per ml.)

The microtitre plates are incubated at room temperature for 10 hours prior to reading in a Trilux scintillation counter. The results are analysed using an automatic spline fitting programme (Multicalc, Packard, Milton Keynes, UK) to provide Ki values for each of the test compounds.

Serotonin Binding Assay

The ability of a test compound to compete with [$^3$H]-citalopram from its binding sites on cloned human serotonin membranes is used as a measure of its ability to block serotonin uptake via its specific transporter (Ramamoorthy, S., Giovanetti, E., Qian, Y., Blakely, R., (1998) J. Biol. Chem. 273,2458).

Membrane Preparation:

The preparation of membrane is essentially similar to that for the norepinephrine transporter containing membrane described above. The membrane preparation is stored in aliquots (1 ml) at −70° C. until required. The protein concentration of the membrane preparation is determined using BCA protein assay reagent kit.

[$^3$H]-Citalopram Binding Assay:

Each well of a 96 well microtitre plate is set up to contain the following:

50 μl 2 nM [$^3$H]-Citalopram (60-86 Ci/mmol, Amersham Biosciences)

75 μl Assay buffer (50 mM Tris.HCl pH 7.4 containing 150 mM NaCl and 5 mM KCl)

25 μl Diluted compound, assay buffer (total binding) or 100 M Fluoxetine (non-specific binding)

50 WGA PVT SPA Beads (40 mg/ml)

50 μl Membrane preparation (0.4 mg protein per ml)

The microtitre plates are incubated at room temperature for 10 hours prior to reading in a Trilux scintillation counter. The results are analysed using an automatic spline fitting programme (Multicalc, Packard, Milton Keynes, UK) to provide Ki (nM) values for each of the test compounds.

Dopamine Binding Assay

The ability to compete with [$^3$H]-WIN35,428 for its binding sites on human cell membranes containing cloned human dopamine transporter is used as a measure of its ability to block dopamine uptake via its specific transporter (Ramamoorthy et al 1998 supra).

Membrane Preparation:

Is essentially the same as for membranes containing cloned human serotonin transporter as described above.

[$^3$H]-WIN35,428 Binding Assay:

Each well of a 96 well microtitre plate is set up to contain the following:

50 μl 4 nM [$^3$H]-WIN35,428428 (84-87 Ci/mmol, from NEN Life Science Products)

75 μl Assay buffer (50 mM Tris.HCl pH 7.4 containing 150 mM NaCl and 5 mM KCl)

25 μl Diluted compound, assay buffer (total binding) or 100 μM Nomifensine (non-specific binding)

50 μl WGA PVT SPA Beads (10 mg/ml)

50μl Membrane preparation (0.2 mg protein per ml.)

The microtitre plates are incubated at room temperature for 120 minutes prior to reading in a Trilux scintillation counter. The results are analysed using an automatic spline fitting programme (Multicalc, Packard, Milton Keynes, UK) to provide Ki values for each of the test compounds.

CYP2D6 Assays

Cytochrome P450 2D6 (CYP2D6) is a mammalian enzyme which is commonly associated with the metabolism of around 30% of pharmaceutical compounds. Moreover, this enzyme exhibits genetic polymorphism, resulting in the presence of both normal and poor metabolizers in the population. A low involvement of CYP2D6 in the metabolism of compounds (i.e. the compound being a poor substrate of CYP2D6) is desirable in order to reduce any variability from subject to subject in the pharmacokinetics of the compound. Also, compounds with a low inhibitor potential for CYP2D6 are desirable in order to avoid drug-drug interactions with co-administered drugs that are substrates of CYP2D6. Compounds may be tested both as substrates and as inhibitors of this enzyme by means of the following assays.

CYP2D6 Substrate Assay

Principle:

This assay determines the extent of the CYP2D6 enzyme involvement in the total oxidative metabolism of a compound in microsomes. Preferred compounds of the present invention exhibit less than 75% total metabolism via the CYP2D6 pathway.

For this in vitro assay, the extent of oxidative metabolism in human liver microsomes (HLM) is determined after a 30 minute incubation in the absence and presence of Quinidine, a specific chemical inhibitor of CYP2D6. The difference in the extent of metabolism in absence and presence of the inhibitor indicates the involvement of CYP2D6 in the metabolism of the compound.

Materials and Methods:

Human liver microsomes (mixture of 20 different donors, mixed gender) are acquired from Human Biologics (Scottsdale, Ariz., USA). Quinidine and β-NADPH (β-Nicotinamide Adenine Dinucleotide Phosphate, reduced form, tetrasodium salt) are purchased from Sigma (St Louis, Mo., USA). All the other reagents and solvents are of analytical grade. A stock solution of the new chemical entity (NCE) is prepared in a mixture of Acetonitrile/Water to reach a final concentration of acetonitrile in the incubation below 0.5%.

The microsomal incubation mixture (total volume 0.1 mL) contains the NCE (4 μM), β-NADPH (1 mM ), microsomal proteins (0.5 mg/mL), and Quinidine (0 or 2 μM) in 100 mM sodium phosphate buffer pH 7.4. The mixture is incubated for 30 minutes at 37° C. in a shaking waterbath. The reaction is terminated by the addition of acetonitrile (75 μL). The samples are vortexed and the denaturated proteins are removed by centrifugation. The amount of NCE in the supernatant is analyzed by liquid chromatography/mass spectrometry (LC/MS) after addition of an internal standard. A sample is also taken at the start of the incubation (t=0), and analysed similarly.

Analysis of the NCE is performed by liquid chromatography/mass spectrometry. Ten μL of diluted samples (20 fold dilution in the mobile phase) are injected onto a Spherisorb CN Column, 5 μM and 2.1 mm×100 mm (Waters corp. Milford, Mass., USA). The mobile phase consisting of a mixture of Solvent A/Solvent B, 30/70 (v/v) is pumped (Alliance 2795, Waters corp. Milford, Mass., USA) through the column at a flow rate of 0.2 ml/minute. Solvent A and Solvent B are a mixture of ammonium formate $5.10^{-3}$ M pH 4.5/methanol in the proportions 95/5 (v/v) and 10/90 (v/v), for solvent A and solvent B, respectively. The NCE and the internal standard are quantified by monitoring their molecular ion using a mass spectrometer ZMD or ZQ (Waters-Micromass corp, Manchester, UK) operated in a positive electrospray ionisation.

The extent of CYP2D6 involvement (% of CYP2D6 involvement) is calculated comparing the extent of metabolism in absence and in presence of quinidine in the incubation.

The extent of metabolism without inhibitor (%) is calculated as follows:

$$\frac{(NCE \text{ response in samples without inhibitor})\text{time } 0 - (NCE \text{ response in samples without inhibitor})\text{time } 30}{(NCE \text{ response in samples without inhibitor})\text{time } 0} \times 100$$

The extent of metabolism with inhibitor (%) is calculated as follows:

$$\frac{(NCE \text{ response in samples without inhibitor})\text{time } 0 - (NCE \text{ response in samples with inhibitor})\text{time } 30}{(NCE \text{ response in samples without inhibitor})\text{time } 0} \times 100$$

where the NCE response is the area of the NCE divided by the area of the internal standard in the LC/MS analysis chromatogram, time0 and time30 correspond to the 0 and 30 minutes incubation time.

The % of CYP2D6 involvement is calculated as follows:

$$\frac{(\% \text{ extent of metabolism without inhibitor}) - (\% \text{ extent of metabolism with inhibitor})}{\% \text{ extent of metabolism without inhibitor}} \times 100$$

CYP2D6 Inhibitor Assay

Principle:

The CYP2D6 inhibitor assay evaluates the potential for a compound to inhibit CYP2D6. This is performed by the measurement of the inhibition of the bufuralol 1'-hydroxylase activity by the compound compared to a control. The 1'-hydroxylation of bufuralol is a metabolic reaction specific to CYP2D6. Preferred compounds of the present invention exhibit an $IC_{50}$ higher than 6 μM for CYP2D6 activity, the $IC_{50}$ being the concentration of the compound that gives 50% of inhibition of the CYP2D6 activity.

Material and Methods:

Human liver microsomes (mixture of 20 different donors, mixed gender) are acquired from Human Biologics (Scottsdale, AZ). β-NADPH is purchased from Sigma (St Louis, Mo.). Bufuralol is purchased from Ultrafine (Manchester, UK). All the other reagents and solvents are of analytical grade.

Microsomal incubation mixture (total volume 0.1 mL) contains bufuralol 10 μM, β-NADPH (2 mM), microsomal proteins (0.5 mg/mL), and the new chemical entity (NCE) (0, 5, and 25 μM) in 100 mM sodium phosphate buffer pH 7.4. The mixture is incubated in a shaking waterbath at 37° C. for 5 minutes. The reaction is terminated by the addition of methanol (75 μL). The samples are vortexed and the denaturated proteins are removed by centrifugation. The supernatant is analyzed by liquid chromatography connected to a fluorescence detector. The formation of the 1'-hydroxybufuralol is monitored in control samples (0 μM NCE) and in the samples incubated in presence of the NCE. The stock solution of NCE is prepared in a mixture of Acetonitrile/Water to reach a final concentration of acetonitrile in the incubation below 1.0%.

The determination of 1'hydroxybufuralol in the samples is performed by liquid chromatograhy with fluorimetric detection as described below. Twenty five μL samples are injected onto a Chromolith Performance RP-18e column (100 mm×4.6 mm) (Merck KGaA, Darmstadt, Germany). The mobile phase, consisting of a mixture of solvent A and solvent B whose the proportions changed according the following linear gradient, is pumped through the column, at a flow rate of 1 ml/min:

| Time (minutes) | Solvent A (%) | Solvent B (%) |
|---|---|---|
| 0 | 65 | 35 |
| 2.0 | 65 | 35 |
| 2.5 | 0 | 100 |
| 5.5 | 0 | 100 |
| 6.0 | 65 | 35 |

Solvent A and Solvent B consist of a mixture of 0.02 M potassium dihydrogenophosphate buffer pH3/methanol in the proportion 90/10 (v/v) for solvent A and 10/90 (v/v) for solvent B. The run time is 7.5 minutes. Formation of 1'-hydroxybufuralol is monitored by fluorimetric detection with extinction at λ252 nm and emission at λ302 nm.

The $IC_{50}$ of the NCE for CYP2D6 is calculated by the measurement of the percent of inhibition of the formation of the 1'-hydroxybufuralol in presence of the NCE compared to control samples (no NCE) at a known concentration of the NCE.

The percent of inhibition of the formation of the 1'-hydroxybufuralol is calculated as follows:

$$\frac{(1' - \text{hydroxybufuralol formed without inhibitor}) - (1' - \text{hydroxybufuralol formed with inhibitor})}{(1' - \text{hydroxybufuralol area formed without inhibitor})} \times 100$$

The $IC_{50}$ is calculated from the percent inhibition of the formation of the 1'-hydroxybufuralol as follows (assuming competitive inhibition):

$$\frac{NCE \text{ Concentration} \times (100 - \text{Percent of inhibition})}{\text{Percent of inhibition}}$$

The $IC_{50}$ estimation is assumed valid if inhibition is between 20% and 80% (Moody G C, Griffin S J, Mather A N, McGinnity D F, Riley R J. 1999. Fully automated analysis of activities catalyzed by the major human liver cytochrome P450 (CYP) enzymes: assessment of human CYP inhibition potential. Xenobiotica, 29(1): 53-75).

The inventioin claimed is:

1. A compound of formula I(a):

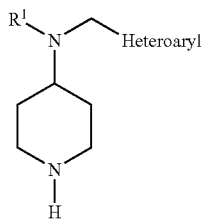

I(a)

where:

R1 is cyclopropylmethyl or $C_3$-$C_5$ alkyl optionally substituted with hydroxy;

Heteroaryl is thienyl, benzothienyl, thiazolyl, or benzothiazolyl each optionally substituted with one or two substituents independently selected from methyl and halo; or a pharmaceutically acceptable salt thereof.

2. A pharmaceutical composition comprising a compound of claim 1 together with a pharmaceutically acceptable diluent, excipient or carrier.

* * * * *